US010246695B2

(12) United States Patent
Gray et al.

(10) Patent No.: US 10,246,695 B2

(45) Date of Patent: Apr. 2, 2019

(54) METHYL BUTENOL SYNTHASE

(71) Applicant: Board of Trustees of Michigan State University, East Lansing, MI (US)

(72) Inventors: Dennis Gray, Bay City, MI (US); Thomas D Sharkey, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 15/797,632

(22) Filed: Oct. 30, 2017

(65) Prior Publication Data

US 2018/0148706 A1 May 31, 2018

Related U.S. Application Data

(62) Division of application No. 15/058,746, filed on Mar. 2, 2016, now Pat. No. 9,803,186, which is a division of application No. 14/174,694, filed on Feb. 6, 2014, now Pat. No. 9,284,578, which is a division of application No. 13/321,458, filed as application No. PCT/US2010/035820 on May 21, 2010, now Pat. No. 8,679,802.

(60) Provisional application No. 61/180,757, filed on May 22, 2009.

(51) Int. Cl.

| | |
|---|---|
| ***C12N 9/88*** | (2006.01) |
| ***C12P 7/04*** | (2006.01) |
| ***C12P 7/16*** | (2006.01) |

(52) U.S. Cl.

CPC .................. *C12N 9/88* (2013.01); *C12P 7/04* (2013.01); *C12P 7/16* (2013.01); *Y02E 50/10* (2013.01)

(58) Field of Classification Search

None

See application file for complete search history.

(56) References Cited

U.S. PATENT DOCUMENTS

| | | | |
|---|---|---|---|
| 6,593,299 | B1 | 7/2003 | Bennett et al. |
| 8,679,802 | B2 | 3/2014 | Gray et al. |
| 9,284,578 | B2 | 3/2016 | Gray et al. |
| 9,803,186 | B2 | 10/2017 | Gray et al. |
| 2008/0038805 | A1 | 2/2008 | Melis |
| 2008/0274523 | A1 | 11/2008 | Renninger et al. |
| 2008/0274525 | A1 | 11/2008 | Bramucci et al. |
| 2008/0318292 | A1 | 12/2008 | Keasling et al. |
| 2009/0269816 | A1 | 10/2009 | Mendez et al. |
| 2012/0156745 | A1 | 6/2012 | Gray et al. |
| 2014/0248675 | A1 | 9/2014 | Gray et al. |
| 2016/0326509 | A1 | 11/2016 | Gray et al. |

FOREIGN PATENT DOCUMENTS

| | | | |
|---|---|---|---|
| WO | WO-2010135674 | A2 | 11/2010 |
| WO | WO-2010135674 | A3 | 11/2010 |

OTHER PUBLICATIONS

00195274, Picea sitchensis (−)-linalool-like synthase mRNA, complete cds. NCBI Nucleotide, Mar. 14, 2006 [online]. [Retrieved on Mar. 11, 2010]., Retrieved from the internet: <URL: http://www.ncbi.nlm.nih.gov/nuccorel77454874>, (2006), 2 pgs.

"U.S. Appl. No. 12/657,748, Response filed Mar. 22, 2014 to Restriction Requirement dated Feb. 21, 2013", 6 pgs.

"U.S. Appl. No. 13/321,458 , Response filed Sep. 3, 2013 to Non Final Office Action dated May 31, 2013", 7 pgs.

"U.S. Appl. No. 13/321,458, Non Final Office Action dated May 31, 2013", 7 pgs.

"U.S. Appl. No. 13/321,458, Notice of Allowance dated Nov. 5, 2013", 12 pgs.

"U.S. Appl. No. 13/321,458, Restriction Requirement dated Feb. 21, 2013", 7 pgs.

"U.S. Appl. No. 14/174,694, Non Final Office Action dated May 7, 2015", 7 pgs.

"U.S. Appl. No. 14/174,694, Notice of Allowance dated Nov. 4, 2015", 10 pgs.

"U.S. Appl. No. 14/174,694, Preliminary Amendment filed Feb. 7, 2014", 4 pgs.

"U.S. Appl. No. 14/174,694, Response filed Mar. 30, 2015 to Restriction Requirement dated Jan. 30, 2015", 6 pgs.

"U.S. Appl. No. 14/174,694, Response filed Sep. 8, 2015 to Non Final Office Action dated May 7, 2015", 7 pgs.

"U.S. Appl. No. 14/174,694, Restriction Requirement dated Jan. 30, 2015", 7 pgs.

"U.S. Appl. No. 15/058,746, Notice of Allowance dated Jun. 27, 2017", 12 pgs.

"U.S. Appl. No. 15/058,746, Preliminary Amendment Filed May 16, 2016", 6 pgs.

"U.S. Appl. No. 15/058,746, Response filed Mar. 31, 2017 to Restriction Requirement dated Jan. 31, 2017", 6 pgs.

"U.S. Appl. No. 15/058,746, Restriction Requirement dated Jan. 31, 2017", 7 pgs.

"International Application Serial No. PCT/US2010/035820, International Preliminary Report of Patentability dated Dec. 1, 2011", 7 pgs.

"International Application Serial No. PCT/US2010/35820, Invitation to Pay Additional Fee dated Sep. 20, 2010", 4 pgs.

"International Application Serial No. PCT/US2010/35820, Search Report dated Mar. 7, 2011", 5 pgs.

"International Application Serial No. PCT/US2010/35820, Written Opinion dated Mar. 7, 2011", 5 pgs.

Byun-McKay, A., et al., "Wound-Induced Terpene Synthase Gene Expression in Sitka Spruce That Exhibits Resistance or Susceptibility to Attack by the White Pine Weevil", Plant Physiology, 140(3), (Mar. 2006), 1009-1021.

(Continued)

*Primary Examiner* — Iqbal H Chowdhury

(74) *Attorney, Agent, or Firm* — Schwegman Lundberg & Woessner, P.A.

(57) ABSTRACT

The present invention provides novels genes encoding methyl butenol (MBO) synthase, methyl butenol synthases and their use in methyl butenol production.

14 Claims, 20 Drawing Sheets

Specification includes a Sequence Listing.

(56) References Cited

OTHER PUBLICATIONS

Demain, A. L, "The Business of Biotechnology", Indust, Biotechnol.; vol. 3 (3), (Fall 2007), 269-283.
Martin, D. M., et al., "Functional Characterization of Nine Norway Spruce TPS Genes and Evolution of Gymnosperm Terpene Synthases of the TPS-d Subfamily", Plant Physiology, 135, (2004), 1908-1927.

P._pseudostrobus_estevezii
TCTAGCAAGGTTAAGGTTGTCCGCAGAACGATCTCAACTTCCATCCGCATG
TGTCGGATAACCACTGTATCCGGTGAAGGCGTACAGAGACGCATAGCAAA
TCATCATTCCAACCTCTGGGACGATAATTTCATACAGTCCCTCTCAACCCC
TTATGGGGCAATTTCGTACCATGAAAGTGCTCAGAAACTTATTGGAGAAG
TAAAAGAGATAATCAATTCAATCTCGGTTAAAGATGGAGAATTAATCACC
CCCTCCAATGATCTCCTTATGCGGCTCTCTATAGTCGATAGCATTGAACGT
TTGGGAATTGATAGGCATTTCAAAAGTGAAATAAAATCAGCTCTGGATTA
CGTTTACAGTTATTGGAACGAAAAAGGCATTGGGTGGGGAAGAGATAGTG
TTGTTGCCGATCTCAACTCAACTGCCTTGGGGCTTCGAACTCTACGACTAC
ACGGATACCCGGTGTCTTCAGATGTGTTACAACACTTCAAAGAACAAAAA
GGGCAGTTTGCATGTTCGGCCATTCAAACAGAGGGAGAGATAAGAAGTGT
TCTCAACTTATTTCGGGCTTCCCAAATTGCCTTTCCGGGAGAGAAAGTTAT
GGAAGAGGCAGAAGTCTTCTCTACAATATATTTAAAAGAAGCCATACTAA
AGCTTCCGGTCTGCGGTCTTTCACGAGAGATATCGTACGTTCTGGAATATG
GTTGGCATATAAATTTGCCAAGATTGGAAGCAAGGAACTACATCGACGTA
TTTGGACAGGACCCCATTTATTTGACGCCAAATATGAAGACCCAAAAACT
TCTAGAACTTGCAAAGTTGGAGTTCAATATGTTTCACTCTTTACAACAGCA
AGAGCTAAAGCTTCTCTCCAGATGGTGGAAAGATTCGGGTTTCTCTCAAAT
GACCTTCCCTCGGCATCGTCACGTGGAATATTACACTTTGGCATCTTGCAT
TGATAGTGAACCTCAACATTCTTCGTTCAGACTTGGATTTGCCAAAATCTT
TCATCTTGCCACGGTTCTTGACGATATTTACGACACCTTTGGCACGATGGA
TGAGCTAGAACTCTTCACGGCGGCAGTTAAGAGGTGGCATCCGTCTGCGA
CGGAGTGGCTTCCAGAATATATGAAAGGAGTATATATGGTGCTTTACGAA
ACCGTTAACGAAATGGCAGGAGAAGCAGAAAAGTCTCAAGGCCGAGACA
CGCTCAACTATGCCCGAAATGCTTTGGAGGCTTATATTGATGCTTCTATGA
AAGAAGCGAAGTGGATTTTCAGTGGTTTTTTGCCAACATTTGAGGAGTAC
CTGGATAACGGGAAAGTTAGTTTCGGTTATAGCATTGGCACATTGCAACC
CATTCTGACGTTGGGCATTCCCTTTCCTCATCACATCCTACAAGAAATAGA
CTTTCCTTCCAGGCTCAATGATGTGGCATGTTCCATTCTCCGACTAAAAGG
CGACATTCACACTTACCAGGCTGAGAGGAGCCGTGGAGAAAAATCTTCGT
GTATATCATGTTATATGGAAGAGAATCCCGAGTCAACAGAGGAAGATGCA
ATCAATCATGTCAACTCCATGGTCGACAAATTACTCAAGGAACTAAATTG
GGAGTATCTGAGACCTGATAGCAATGTTCCAATCACTTCCAAGAAACATG
CATTTGACATTCTGAGAGCTTTCTACCATCTCTACAAATACCGAGATGGCT
TCAGCGTTGCGAACTATGAAATAAAGAATTTGGTCATGACAACCGTCATT
GAGCCTGTGCCTTTATAA- (SEQ ID NO:1)

P_cooperi_ornelasi_MBO
TCTAGCAAGGTTAAGGTTGTCCGCAGAACGATCTCAACTTCCATCCGCATG
TGTCGGATAACCACTGTATCCGGTGAAGGCGTACAGAGACGCATAGCAAA
TCATCATTCCAACCTCTGGGACGATAATTTCATACAGTCCCTCTCAACGCC
TTATGGGGCAATTTCGTACCATGAAAGTGCTCAGAAACTTATTGGAGAAG
TAAAAGAGATGATCAATTCAATCTCGGTTAAAGATGGAGAATTAATCACC
CCCTCCAATGATCTCCTTATGCGGCTCTCTATAGTCGATAGCATTGAACGT
TTGGGAATCGATAGGCATTTCAAAAGTGAAATAAAATCAGCTCTGGATTA
TGTTTACAGTTATTGGAACGAAAAAGGCATTGGGTGGGGAAGAGATAGTG
TTGTTGCCGATCTCAACTCAACTGCCTTGGGGCTTCGAACTCTACGACTAC

FIG.1A

ACGGATACCCGGTGTCTTCAGATGTGTTACAACACTTCAAAGAACAAAAA
GGGCAGTTTGCATGTTCGGCCATTCAAACAGAGGGAGAGATAAGAAGTGT
TCTCAACTTATTTCGGGCTTCCCAAATTGCCTTTCCGGGAGAGAAAGTTAT
GGAAGAGGCAGAAGTCTTCTCTACAATATATTTAAAAGAAGCCATACTAA
AGCTTCCGGTCTGCGGTCTTTCACGAGAGATATCGTACGTTCTGGAATATG
GTTGGCATATAAATTTGCCAAGATTGGAAGCAAGGAACTACATCGACGTA
TTTGGACAGGACCCCATTTATTTGACGCCAAATATGAAGACCCAAAAACT
TCTAGAACTTGCAAAGTTGGAGTTCAATATGTTTCACTCTTTACAACAGCA
AGAGCTAAAGCTTCTCTCCAGATGGTGGAAAGATTCGGGTTTCTCTCAAAT
GACCTTCCCTCGGCATCGTCACGTGGAATATTACACTTTGGCATCTTGCAT
TGATAGTGAACCTCAACATTCTTCGTTCAGACTTGGATTTGCCAAAATCTT
TCATCTTGCCACGGTTCTTGACGATATTTACGACACCTTTGGCACGATGGA
TGAGCTAGAACTCTTCACGGCGGCAGTTAAGAGGTGGCATCCGTCTGCGA
CGGAGTGGCTTCCAGAATATATGAAAGGAGTATATATGGTGCTTTACGAA
ACCGTTAACGAAATGGCAGGAGAAGCAGAAAAGTCTCAAGGCCGAGACA
CGCTCAACTATGCCCGAAATGCTTTGGAGGCTTATATTGATGCTTCTATGA
AAGAAGCGAAGTGGATTTTCAGTGGTTTTTTGCCAACATTTGAGGAGTAC
CTGGATAACGGGAAAGTTAGTTTCGGTTATAGCATTGGCACATTGCAACC
CATTCTGACGTTGGGCATTCCCTTTCCTCATCACATCCTACAAGAAATAGA
CTTTCCTTCCAGGCTCAATGATGTGGCATGTTCCATTCTCCGACTAAAAGG
CGACATTCACACTTACCAGGCTGAGAGGAGCCGTGGAGAAAAATCTTCGT
GTATATCATGTTATATGGAAGAGAATCCCGAGTCAACAGAGGAAGATGCA
ATCAATCATATCAACTCCATGGTCGACAAATTACTCAAGGAACTAAATTG
GGAGTATCTGAGACCTGATAGCAATGTTCCAATCACTTCCAAGAAACATG
CATTTGACATTCTGACAGCTTTCTACCATCTCTACAAATACCGAGATGGCT
TCAGCGTTGCGAACTATGAAATAAAGAATTTGGTCATGACAACCGTCATT
GAGCCTGTGCCTTTATAA-(SEQ ID NO:2)

P._hartwegii_MBO
TCTAGCAAGGTTAAGGTTGTCCGCAGAACGATCTCAACTTCCATCCGCATG
TGTCGGATAACCACTGTATCCGGTGAAGGCGTACAGAGACGCATAGCAAA
TCATCATTCCAACCTCTGGGACGATAATTTCATACAGTCCCTCTCAACGCC
TTATGGGGCAATTTCGTACCATGAAAGTGCTCAGAAACTTATTGGAGAAG
TAAAAGAGATGATCAATTCAATCTCGGTTAAAGATGGAGAATTAATCACC
CCCTCCAATGATCTCCTTATGCGGCTCTCTATAGTCGATAGCATTGAACGT
TTGGGAATCGATAGGCATTTCAAAAGTGAAATAAAATCAGCTCTGGATTA
TGTTTACAGTTATTGGAACGAAAAAGGCATTGGGTGGGGAAGAGATAGTG
TTGTTGCCGATCTCAACTCAACTGCCTTGGGGCTTCGAACTCTACGACTAC
ACGGATACCCGGTGTCTTCAGATGTGTTACAACACTTCAAAGAACAAAAA
GGGCAGTTTGCATGTTCGGCCATTCAAACAGAGGGAGAGATAAGAAGTGT
TCTCAACTTATTTCGGGCTTCCCAAATTGCCTTTCCGGGAGAGAAAGTTAT
GGAAGAGGCAGAAGTCTTCTCTACAATATATTTAAAAGAAGCCATACTAA
AGCTTCCGGTCTGCGGTCTTTCACGAGAGATATCGTACGTTCTGGAATATG
GTTGGCATATAAATTTGCCAAGATTGGAAGCAAGGAACTACATCGACGTA
TTTGGACAGGACCCCATTTATTTGACGCCAAATATGAAGACCCAAAAACT
TCTAGAACTTGCAAAGTTGGAGTTCAATATGTTTCACTCTTTACAACAGCA
AGAGCTAAAGCTTCTCTCCAGATGGTGGAAAGATTCGGGTTTCTCTCAAAT
GACCTTCCCTCGGCATCGTCACGTGGAATATTACACTTTGGCATCTTGCAT
TGATAGTGAACCTCAATATTCTTCGTTCAGACTTGGATTTGCCAAAATCTT
TCATCTTGCCACGGTTCTTGACGATATTTACGACACCTTTGGCACGATGGA

FIG. 1B

TGAGCTAGAACTCTTCACGGCGGCAGTTAAGAGGTGGCATCCGTCTGCGA
CGGAGTGGCTTCCAGAATATATGAAAGGAGTATATATGGTGCTTTACGAA
ACCGTTAACGAAATGGCAGGAGAAGCAGAAAAGTCTCAAGGCCGAGACA
CGCTCAACTATGCCCGAAATGCTTTGGAGGCTTATATTGATGCTTCTATGA
AAGAAGCGAAGTGGATTTTCAGTGGTTTTTTGCCAACATTTGAGGAGTAC
CTGGATAACGGGAAAGTTAGTTTCGGTTATAGCATTGGCACATTGCAACC
CATTCTGACGTTGGGCATTCCCTTTCCTCATCACATCCTACAAGAAATAGA
CTTTCCTTCCAGGCTCAATGATGTGGCATGTTCCATTCTCCGACTAAAAGG
CGACATTCACACTTACCAGGCTGAGAGGAGCCGTGGAGAAAAATCTTCGT
GTATATCATGTTATATGGAAGAGAATCCCGAGTCAACAGAGGAAGATGCA
ATCAATCATATCAACTCCATGGTCGACAAATTACTCAAGGAACTAAATTG
GGAGTATCTGAGACCTGATAGCAATGTTCCAATCACTTCCAAGAAACATG
CATTTGACATTCTGAGAGCTTTCTACCATCTCTACAAATACCGAGATGGCT
TCAGCGTTGCGAACTATGAAATAAAGAATTTGGTCATGACAACCGTCATT
GAGCCTGTGCCTTTATAA-(SEQ ID NO:3)

P._ponderosa_MBO1
TCTAGCAAGGTTAAGGTTGTCCGCAGAACGATCTCAACTTCCATCCGCATG
TGTCGGATAACCACTGAATCCGGTGAAGGCGTACAGAGACGCATAGCAAA
TCATCATTCCAACCTCTGGGACGATAATTTCATACAGTCCCTCTCAACGCC
TTATGGGGCAATTTCGTACCATGAAAGTGCTCAGAAACTTATTGGAGAAG
TAAAAGAGATGATCAATTCAATCTCGCTTAAAGATGGAGAATTAATCACC
CCCTCCAATGATCTCCTTATGCGGCTCTCTATAGTTGATAGCATTGAACGT
TTGGGAATCGATAGGCATTTCAAAAGTGAAATAAAATCAGCTCTGGATTA
TGTTTACAGTTATTGGAACGAAAAAGGCATTGGGTGGGGAAGAGATAGTG
TTGTTGCCGATCTCAACTCAACTGCCTTGGGGCTTCGAACTCTACGACTAC
ACGGATACCCGGTGTCTTCAGATGTGTTACAACACTTCAAAGAACAAAAA
GGGCAGTTTGCATGTTCGGCCATTCAAACAGAGGGAGAGATAAGAAGTGT
TCTCAACTTATTTCGGGCTTCCCAAATTGCCTTTCCGGGAGAGAAAGTTAT
GGAAGAGGCAGAAGTCTTCTCTACAATATATTTAAAAGAAGCCATACTAA
AGCTTCCGGTCTGCGGTCTTTCACGAGAGATATCGTACGTTCTGGAATATG
GTTGGCATATAAATTTGCCAAGATTGGAAGCAAGGAACTACATCGACGTA
TTTGGACAGGACCCCATTTATTTGACGCCAAATATGAAGACCCAAAAACT
TCTAGAACTTGCAAAGTTGGAGTTCAATATGTTTCACTCTTTACAACAGCA
AGAGCTAAAGCTTCTCTCCAGATGGTGGAAAGATTCGGGTTTCTCTCAAAT
GACCTTCCCTCGGCATCGTCACGTGGAATATTACACTTTGGCATCTTGCAT
TGATAGTGAACCTCAACATTCTTCGTTCAGACTTGGATTTGCCAAAATCTT
TCATCTTGCCACGGTTCTTGACGATATTTACGACACCTTTGGCACGATGGA
TGAGCTAGAACTCTTCACGGCGGCAGTTAAGAGGTGGCATCCGTCTGCGA
CGGAGTGGCTTCCAGAATATATGAAAGGAGTATATATGGTGCTTTACGAA
ACCGTTAACGAAATGGCGAGAGAAGCAGAAAAGTCTCAAGGCCGAGACA
CGCTCAACTATGCCCGAAATGCTTTGGAGGCTTATATTGATGCTTCTATGA
AAGAAGCGAAGTGGATTTTCAGTGGTTTTTTGCCAACATTTGAGGAGTAC
CTGGATAACGGGAAAGTTAGTTTCGGTTATAGCATTGGCACATTGCAACC
CATTCTGACGTTGGGCATTCCCTTTCCTCATCACATCCTACAAGAAATAGA
CTTTCCTTCCAGGCTCAATGATGTGGCATGTTCCATTCTCCGACTAAAAGG
CGACATTCACACTTACCAGGCTGAGAGGAGCCGTGGAGAAAAATCTTCGT
GTATATCATGTTATATGGAAGAGAATCCCGAGTCAACAGAGGAAGATGCA
ATCAATCATATCAACTCCATGGTCGACAAATTACTCAAGGAACTAAATTG
GGAGTATCTGAGACCTGATAGCAATGTTCCAATCACTTCCAAGAAACATG

FIG. 1C

CATTTGACATTCTGAGAACTTTCTACCATCTCTACAAATACCGAGATGGCT
TCAGCGTTGCGAACTATGAAATAAAGAATTTGGTCATGACAACCGTCATT
GAGCCTGTGCCTTTATAA-(SEQ ID NO:4)

P._ponderosa_MBO2
TCTAGCAAGGTTAAGGTTGTCCGCAGAACGATCTCAACTTCCATCCGCATG
TGTCGGATAACCACTGAATCCGGTGAAGGCGTACAGAGACGCATAGCAAA
TCATCATTCCAACCTCTGGGACGATAATTTCATACAGTCCCTCTCAACGCC
TTATGGGGCAATTTCGTACCATGAAAGTGCTCAGAAACTTATTGGAGAAG
TAAAAGAGATGATCAATTCAATCTCGCTTAAAGATGGAGAATTAATCACC
CCCTCCAATGATCTCCTTATGCGGCTCTCTATAGTTGATAGCATTGAACGT
TTGGGAATCGATAGGCATTTCAAAAGTGAAATAAAATCAGCTCTGGATTA
TGTTTACAGTTATTGGAACGAAAAAGGCATTGGGTGGGAAGAGATAGTG
TTGTTGCCGATCTCAACTCAACTGCCTTGGGGCTTCGAACTCTACGACTAC
ACGGATACCCGGTGTCTTCAGATGTGTTACAACACTTCAAAGAACAAAAA
GGGCAGTTTGCATGTTCGGCCATTCAAACAGAGGGAGAGATAAGAAGTGT
TCTCAACTTATTTCGGGCTTCCCAAATTGCCTTTCCGGGAGAGAAAGTTAT
GGAAGAGGCAGAAGTCTTCTCTACAATATATTTAAAAGAAGCCATACTAA
AGCTTCCGGTCTGCGGTCTTTCACGAGAGATATCGTACGTTCTGGAATATG
GTTGGCATATAAATTTGCCAAGATTGGAAGCAAGGAACTACATCGACGTA
TTTGGACAGGACCCCATTTATTTGACGCCAAATATGAAGACCCAAAAATT
TCTAGAACTTGCAAAGTTGGAGTTCAATATGTTTCACTCTTTACAACAGCA
AGAGCTAAAGCTTCTCTCCAGATGGTGGAAAGATTCGGGTTTCTCTCAAAT
GACCTTCCCTCGGCATCGTCACGTGGAATATTACACTTTGGCATCTTGCAT
TGATAGTGAACCTCAACATTCTTCGTTCAGACTTGGATTTGCCAAAATCTT
TCATCTTGCCACGGTTCTTGACGATATTTACGACACCTTTGGCACGATGGA
TGAGCTAGAACTCTTCACGGCGGCAGTTAAGAGGTGGCATCCGTCTGCGA
CGGAGTGGCTTCCAGAATATATGAAAGGAGTATATATGGTGCTTTACGAA
ACCGTTAACGAAATGGCGAGAGAAGCAGAAAAGTCTCAAGGCCGAGACA
CGCTCAACTATGCCCGAAATGCTTTGGAGGCTTATATTGATGCTTCTATGA
AAGAAGCGAAGTGGATTTTCAGTGGTTTTTTGCCAACATTTGAGGAGTAC
CTGTATAACGGGAAAGTTAGTTTCGGTTATAGCATTGGCACATTGCAACCC
ATTCTGACGTTGGGCATTCCCTTTCCTCATCACATCCTACAAGAAATAGAC
TTTCCTTCCAGGCTCAATGATGTGGCATGTTCCATTCTCCGACTAAAAGGC
GACATTCACACTTACCAGGCTGAGAGGAGCCGTGGAGAAAAATCTTCGTG
TATATCATGTTATATGGAAGAGAATCCCGAGTCAACAGAGGAAGATGCAA
TCAATCATATCAACTCCATGGTCGACAAATTACTCAAGGAACTAAATTGG
GAGTATCTGAGACCTGATAGCAATGTTCCAATCACTTCCAAGAAACATGC
ATTTGACATTCTGAGAACTTTCTACCATCTCTACAAATACCGAGATGGCTT
CAGCGTTGCGAACTATGAAATAAAGAATTTGGTCATGACAACCGTCATTG
AGCCTGTGCCTTTATAA-(SEQ ID NO:5)

P._jeffreyi_MBO
TCTAGCAAGGTTAAGGTTGTCCGCAGAACGATCTCAACTTCCATCCGCATG
TGTCGGATAACCACTGAATCCGGTGAAGGCGTACAGAGACGCATAGCAAA
TCATCATTCCAACCTCTGGGACGATAATTTCATACAGTCCCTCTCAACGCC
TTATGGGGCAATTTCGTACCATGAAAGTGCTCAGAAACTTATTGGAGAAG
TAAAAGAGATGATCAATTCAATCTCGCTTAAAGATGGAGAATTAATCACC
CCCTCCAATGATCTCCTTATGCGGCTCTCTATAGTTGATAGCATTGAACGT
TTGGGAATCGATAGGCATTTCAAAAGTGAAATAAAATCAGCTCTGGATTA

FIG. 1D

TGTTTACAGTTATTGGAACGAAAAAGGCATTGGGTGGGGAAGAGATAGTG
TTGTTGCCGATCTCAACTCAACTGCCTTGGGGCTTCGAACTCTACGACTAC
ACGGATACCCGGTGTCTTCAGATGTGTTACAACACTTCAAAGAACAAAAA
GGGCAGTTTGCATGTTCGGCCATTCAAACAGAGGGAGAGATAAGAAGTGT
TCTCAACTTATTTCGGGCTTCCCAAATTGCCTTTCCGGGAGAGAAAGTTAT
GGAAGAGGCAGAAGTCTTCTCTACAATATATTTAAAAGAAGCCATACTAA
AGCTTCCGGTCTGCGGTCTTTCACGAGAGATATCGTACGTTCTGGAATATG
GTTGGCATATAAATTTGCCAAGATTGGAAGCAAGGAACTACATCGACGTA
TTTGGACAGGACCCCATTTATTTGACGCCAAATATGAAGACCCAAAAACT
TCTAGAACTTGCAAAGTTGGAGTTCAATATGTTTCACTCTTTACAACAGCA
AGAGCTAAAGCTTCTCTCCAGATGGTGGAAAGATTCGGGTTTCTCTCAAAT
GACCTTCCCTCGGCATCGTCACGTGGAATATTACACTTTGGCATCTTGCAT
TGATAGTGAACCTCAACATTCTTCGTTCAGACTTGGATTTGCCAAAATCTT
TCATCTTGCCACGGTTCTTGACGATATTTACGACACCTTTGGCACGATGGA
TGAGCTAGAACTCTTCACGGCGGCAGTTAAGAGGTGGCATCCGTCTGCGA
CGGAGTGGCTTCCAGAATATATGAAAGGAGTATATATGGTGCTTTACGAA
ACCGTTAACGAAATGGCAGGAGAAGCAGAAAAGTCTCAAGGCCGAGACA
CGCTCAACTATGCCCGAAATGCTTCGGAGGCTTATATTGATGCTTCTATGA
AAGAAGCGAAGTGGATTTTCAGTGGTTTTTTGCCAACATTTGAGGAGTAC
CTGGATAACGGGAAAGTTAGTTTCGGTTATAGCATTGGCACATTGCAACC
CATTCTGACGTTGGGCATTCCCTTTCCTCATCACATCCTACAAGAAATAGA
CTTTCCTTCCAGGCTCAATGATGTGGCATGTTCCATTCTCCGACTAAAAGG
CGACATTCACACTTACCAGGCTGAGAGGAGCCGTGGAGAAAAATCTTCGT
GTATATCATGTTATATGGAAGAGAATCCCGAGTCAACAGAGGAAGATGCA
ATCAATCATATCAACTCCATGGTCGACAAATTACTCAAGGAACTAAATTG
GGAGTATCTGAGACCTGATAGCAATGTTCCAATCACTTCCAAGAAACATG
CATTTGACATTCTGAGAGCTTTCTACCATCTCTACAAATACCGAGATGGCT
TCAGCGTTGCGAACTATGAAATAAAGAATTTGGTCATGACAACCGTCATT
GAGCCTGTGCCTTTATAA-(SEQ ID NO:6)

P._sabiniana_MBO1
TCTAGCAAGGTTAAGGTTGTCCGCAGAACGATCTCAACTTCCATCCGCATG
TGTCGGATAACCACTGAATCCGGTGAAGGCGTACAGAGACGCATAGCAAA
TCATCATTCCAACCTCTGGGACGATAATTTCATACAGTCCCTCTCAACGCC
TTATGGGGCAATTTCGTACCATGAAAGTGCTCAGAAACTTATTGGAGAAG
TAAAAGAGATGATCAATTCAATCTCGGTTAAAGATGGAGAATTAATCACC
CCCTCCAATGATCTCCTTATGCGGCTCTCTATAGTTGATAGCATTGAACGT
TTAGGAATCGATAGGCATTTCAAAAGTGAAATAAAATCAGCTCTGGATTA
TGTTTACAGTTATTGGAACGAAAAAGGCATTGGGTGGGGAAGAGATAGTG
TTGTTGCCGATCTCAACTCAACTGCCTTGGGGCTTCGAACTCTACGACTAC
ACGGATACCCGGTGTCTTCAGATGTGTTACAACACTTCAAAGAACAAAAA
GGGCAGTTTGCATGTTCGGCCATTCAAACAGAGGGAGAGATAAGAAGTGT
TCTCAACTTATTTCGGGCTTCCCAAATTGCCTTTCCGGGAGAGAAAGTTAT
GGAAGAGGCAGAAGTCTTCTCTACAATATATTTAAAAGAAGCCATACTAA
AGCTTCCGGTCTGCGGTCTTTCACGAGAGATATCGTACGTTCTGGAATATG
GTTGGCATATAAATTTGCCAAGATTGGAAGCAAGGAACTACATCGACGTA
TTTGGAGAGGACCCCATTTATTTGACGCCAAATATGAAGACCCAAAAACT
TCTAGAACTTGCAAAGTTGGAGTTCAATATGTTTCACTCTTTACAACAGCA
AGAGCTAAAGCTTCTCTCCAGATGGTGGAAAGATTCGGGTTTCTCTCAAAT
GACCTTCCCTCGGCATCGTCACGTGGAATATTACACTTTGGCATCTTGCAT

FIG. 1E

TGATAGTGAACCTCAACATTCTTCGTTCAGACTTGGATTTGCCAAAATCTT
TCATCTTGCCACGGTTCTTGACGATATTTACGACACCTTTGGCACGATGGA
TGAGCTAGAACTCTTCACGGCGGCAGTTAAGAGGTGGCATCCGTCTGCGA
CGGAGTGGCTTCCAGAATATATGAAAGGAGTATATATGGTGCTTTACGAA
ACCGTTAACGAAATGGCAGGAGAAGCAGAAAAGTCTCAAGGCCGAGACA
CGCTCAACTATGGCCGAAATGCTTTGGAGGCTTATATTGATGCTTCTATGG
AAGAAGCGAAGTGGATTTTCAGTGGTTTTTTGCCAACATTTGAGGAGTAC
CTGGATAACGGGAAAGTTAGTTTCGGTTATGGCATTGGCACATTGCAACC
CATTCTGACGTTGGGCATTCCCTTTCCTCATCACATCCTACAAGAAATAGA
CTTTCCTTCCAGGCTCAATGATGTGGCATCTTCCATTCTCCGACTAAAAGG
CGACATTCACACTTACCAGGCTGAGAGGAGCCGTGGAGAAAAATCTTCGT
GTATATCATGTTATATGGAAGAGAATCCCGAGTCAACAGAGGAAGATGCA
ATCAATCATATCAACTCCATGGTCGACAAATTACTCAAGGAACTAAATTG
GGAGTATCTGAGACCTGATAGCAATGTTCCAATCACTTCCAAGAAACATG
CATTTGACATTCTGAGAGCTTTCTACCATCTCTACAAATACCGAGATGGCT
TCAGCGTTGCGAACTATGAAATAAAGAATTTGGTCATGACAACCGTCATT
GAGCCTG------------(SEQ ID NO:7)

P._sabiniana_MBO2
TCTAGCAAGGTTAAGGTTGTCCGCAGAACGATCTCAACTTCCATCCGCATG
TGTCGGATAACCACTGAATCCGGTGAAGGCGTACAGAGACGCATAGCAAA
TCATCATTCCAACCTCTGGGACGATAATTTCATACAGTCCCTCTCAACGCC
TTATGGGGCAATTTCGTACCATGAAAGTGCTCAGAAACTTATTGGAGAAG
TAAAAGAGATGATCAATTCAATCTCGCTTAAAGATGGAGAATTAATCACC
CCCTCCAATGATCTCCTTATGCGGCTCTCTATAGTCGATAGCATTGAACGT
TTGGGAATCGATAGGCATTTCAAAAGTGAAATAAAATCAGCTCTGGATTA
TGTTTACAGTTATTGGAACGAAAAAGGCATTGGGTGGGGAAGAGATAGTG
TTGTTGCCGATCTCAACTCAACTGCCTTGGGGCTTCGAACTCTACGACTAC
ACGGATACCCGGTGTCTTCAGATGTGTTACAACACTTCAAAGAACAAAAA
GGGCAGTTTGCATGTTCGGCCATTCAAACAGAGGGAGAGATAAGAAGTGT
TCTCAACTTATTTCGGGCTTCCCAAATTGCCTTTCCGGGAGAGAAAGTTAT
GGAAGAGGCAGAAGTCTTCTCTACAATATATTTAAAAGAAGCCATACTAA
AGCTTCCGGTCTGCGGTCTTTCACGAGAGATATCGTACGTTCTGGAATATG
GTTGGCATATAAATTTGCCAAGATTGGAAGCAAGGAACTACATCGACGTA
TTTGGAGAGGACCCCATTTATTTGACGCCAAATATGAAGACCCAAAAACT
TCTAGAACTTGCAAAGTTGGAGTTCAATATGTTTCACTCTTTACAACAGCA
AGAGCTAAAGCTTCTCTCCAGATGGTGGAAAGATTCGGGTTTCTCTCAAAT
GACCTTCCCTCGGCATCGTCACGTGGAATATTACACTTTGGCATCTTGCAT
TGATAGTGAACCTCAACATTCTTCGTTCAGACTTGGATTTGCCAAAATCTT
TCATCTTGCCACGGTTCTTGACGATATTTACGACACCTTTGGCACGATGGA
TGAGCTAGAACTCTTCACGGCGGCAGTTAAGAGGTGGCATCCGTCTGCGA
CGGAGTGGCTTCCAGAATATATGAAAGGAGTATATATGGTGCTTTACGAA
ACCGTTAACGAAATGGCAGGAGAAGCAGAAAAGTCTCAAGGCCGAGACA
CGCTCAACTATGGCCGAAATGCTTTGGAGGCTTATATTGATGCTTCTATGG
AAGAAGCGAAGTGGATTTTCAGTGGTTTTTTGCCAACATTTGAGGAGTAC
CTGGATAACGGGAAAGTTAGTTTCGGTTATGGCATTGGCACATTGCAACC
CATTCTGACGTTGGGCATTCCCTTTCCTCATCACATCCTACAAGAAATAGA
CTTTCCTTCCAGGCTCAATGATGTGGCATCTTCCATTCTCCGACTAAAAGG
CGACATTCACACTTACCAGGCTGAGAGGAGCCGTGGAGAAAAATCTTCGT
GTATATCATGTTATATGGAAGAGAATCCCGAGTCAACAGAGGAAGATGCA

FIG. 1F

ATCAATCATATCAACTCCATGGTCGACAAATTACTCAAGGAACTAAATTG
GGAGTATCTGAGACCTGATAGCAATGTTCCAATCACTTCCAAGAAACATG
CATTTGACATTCTGAGAGCTTTCTACCATCTCTACAAATACCGAGATGGCT
TCAGCGTTGCGAACTATGAAATAAAGAATTTGGTCATGACAACCGTCATT
GAGCCTGTGCCTTTATAAA (SEQ ID NO:8)

P._patula_MBO
TCTAGCAAGGTTAAGGTTGTCCGCAGAACGATCTCAACTTCCATCCGCATG
TGTCGGATAACTACTGTATCCGGTGAAGGCGTACAGAGACGCATAGCAAA
TCATCATTCCAACCTCTGGGACGATAATTTCATACAGTCCCTCTCAACGCC
TTATGGGGCAATTTCGTACCATGAAAGTGCTCAGAAACTTATTGGAGAAG
TAAAAGAGATGATCAATTCAATCTCGGTTAAAGATGGAGAATTAATCACC
CCCTCCAATGATCTCCTTATGCGGCTCTCTATAGTCGATAGCATTGAACGT
TTGGGAATCGATAGGCATTTCAAAAGTGAAATAAAATCAGCTCTGGATTA
TGTTTACAGTTATTGGAACGAAAAAGGCATTGGGTGGGGAAGAGATAGTG
TTGTTGCCGATCTCAACTCAACTGCCTTGGGGCTTCGAACTCTACGACTAC
ACGGATACCCGGTGTCTTCAGATGTGTTACAACACTTCAAAGAACAAAAA
GGGCAGTTTGCATGTTCGGCCATTCAAACAGAGGGAGAGATAAGAAGTGT
TCTCAACTTATTTCGGGCTTCCCAAATTGCCTTTCCGGGAGAGAAAGTTAT
GGAAGAGGCAGAAGTCTTCTCTACAATATATTTAAAAGAAGCCATACTAA
AGCTTCCGGTCTGCGGTCTTTCACGAGAGATATCGTACGTTCTGGAATATG
GTTGGCATATAAATTTGCCAAGATTGGAAGCAAGGAACTACATCGACGTA
TTTGGACAGGACCCCATTTATTTGACGCCAAATATGAAGACCCAAAAACT
TCTAGAACTTGCAAAGTTGGAGTTCAATATGTTTCACTCTTTACAACAGCA
AGAGCTAAAGCTTCTCTCCAGATGGTGGAAAGATTCGGGTTTCTCTCAAAT
GACCTTCCCTCGGCATCGTCACGTGGAATATTACACTTTGGCATCTTGCAT
TGATAGTGAACCTCAACATTCTTCGTTCAGACTTGGATTTGCCAAAATATT
TCATCTTGCCACGGTTCTTGACGATATTTACGACACCTTTGGCACGATGGA
TGAGCTAGAACTCTTCACAGCGGCAGTTGAGAGGTGGCATCCGTCTGCGA
CGGAGTGGCTTCCAGAATATATGAAAGGAGTATATATGGTGCTTTACGAA
ACCGTTAACGAAATGGCAGGAGAAGCAGAAAAGTCTCAAGGCCGAGACA
CGCTCAACTATGCCCGAAATGCTTTGGAGGCTTATATTGATGCTTCTATGA
AAGAAGCGAAGTGGATTTTCAGTGGTTTTTTGCCAACATTTGAGGAGTAC
CTGGATAACGGGAAAGTTAGTTTCGGTTATAGCATTGGCACATTGCAACC
CATTCTGACGTTGGGCATTCCCTTTCCTCATCACATCCTACAAGAAATAGA
CTTTCCTTCCAGGCTCAATGATGTGGCATGTTCCATTCTCCGACTAAAGG
CGACATTCACACTTACCAGGCTGAGAGGAGCCGTGGAGAAAATCTTCGT
GTATATCATGTTATATGGAAGAGAATCCCGAGTCAACAGAGGAAGATGCA
ATCGATCATATCAACTCCATGGTCGACAAATTACTCAAGGAACTAAATCG
GGAGTATCTGAGACCTGATAGCAATGTTCCAATCACTTCCAAGAAACATG
CATTTGACATTCTGAGAGCTTTCTACCATCTCTACAAATACCGAGATGGCT
TCAGCGTTGCGAACTATGAAATAAAGAATTTGGTCATGACAACCGTCATT
GAGCCTGTGCCTTTATAA-(SEQ ID NO:9)

P._montezumae_MBO
TCTAGCAAGGTTAAGGTTGTCCGCAGAACGATCTCAACTTCCATCCGCATG
TGTCGGATAACCACTGTATCCGGTGAAGGCGTACAGAGACGCATAGCAAA
TCATCATTCCAACCTCTGGGACGATAATTTCATACAGTCCCTCTCAACGCC
TTATGGGGCAATTTCGTACCATGAAAGTGCTCAGAAACTTATTGGAGAAG
TAAAAGAGATGATCAATTCAATCTCGGTTAAAGATGGAGAATTAATCACC

FIG.1G

CCCTCCAATGATCTCCTTATGCGGCTCTCTATAGTCGATAGCATTGAACGT
TTGGGAATCGATAGGCATTTCAAAAGTGAAATAAAATCAGCTCTGGATTA
TGTTTACAGTTATTGGAACGAAAAAGGCATTGGGTGGGGAAGAGATAGTG
TTGTTGCCGATCTCAACTCAACTGCCTTGGGGCTTCGAACTCTACGACTAC
ACGGATACCCGGTGTCTTCAGATGTGTTACAGCACTTCAAAGAACAAAAA
GGGCAGTTTGCATGTTCGGCCATTCAAACAGAGGGAGAGATAAGAAGTGT
TCTCAACTTATTTCGGGCTTCCCAAATTGCCTTTCCGGGAGAGAAAGTTAT
GGAAGAGGCAGAAGTCTTCTCTACAATATATTTAAAAGAAGCCATACTAA
AGCTTCCGGTCTGCGGTCTTTCACGAGAGATATCGTACGTTCTGGAATATG
GTTGGCATATAAATTTGCCAAGATTGGAAGCAAGGAACTACATCGACGTA
TTTGGACAGGACCCCATTTATTTGACGCCAAATATGAAGACCCAAAAACT
TCTAGAACTTGCAAAGTTGGAGTTCAATATGTTTCACTCTTTACAACAGCA
AGAGCTAAAGCTTCTCTCCAGATGGTGGAAAGATTCGGGTTTCTCTCAAAT
GACCTTCCCTCGGCATCGTCACGTGGAATATTACACTTTGGCATCTTGCAT
TGATAGTGAACCTCAACATTCTTCGTTCAGACTTGGATTTGCCAAAATGTT
TCATCTTGCCACGGTTCTTGACGATATTTACGACACCTTTGGCACGATGGA
TGAGCTAGAACTCTTCACGGCGGCAGTTAAGAGGTGGCATCCGTCTGCGA
CGGAGTGGCTTCCAGAATATATGAAAGGAGTATATATGGTGCTTTACGAA
ACCGTTAACGAAATGGCAGGAGAAGCAGAAAAGTCTCAAGGCCGAGACA
CGCTCAACTATGCCCGAAATGCTTTGGAGGCTTATATTGATGCTTCTATGA
AAGAAGCGAAGTGGATTTTCAGTGGTTTTTTGCCAACATTTGAGGAGTAC
CTGGATAACGGGAAAGTTAGTTTCGGTTATAGCATTGGCACATTGCAACC
CATTCTGACGTTGGGCATTCCCTTTCCTCATCACATCCTACAAGAAATAGA
CTTTCCTTCCAGGCTCAATGATGTGGCATGTTCCATTCTCCGACTAAAAGG
CGACATTCACACTTACGAGGCTGAGAGGAGCCGTGGAGAAAAATCTTCGT
GTATATCATGTTATATGGAAGAGAATCCCGAGTCAACAGAGGAAGATGCA
ATCAATCATATCAACTCCATGGTCGACAAATTACTCAAGGAACTAAATTG
GGAGTATCTGAGACCTGATAGCAATGTTCCAATCACTTCCAAGAAACATG
CATTTGACATTCTGAGAGCTTTCTACCATCTCTACAAATACCGAGATGGCT
TCAGCGTTGCGAACTATGAAATAAAGAATTTGGTCATGACAACCGTCATT
GAGCCTGTGCCTTTATAA-(SEQ ID NO:10)

P._pseudostrobus_MBO-----------------------------------------------------------------
AGACGCAKAGSTGRTYWYCATTCCAACCTYTGGGACGATAATTTCATACA
GTCCCTCTCAACGCCTTATGGGGCAATTTCGTACCATGAAAGTGCTCAGAA
ACTTATTGGAGAAGTAAAAGAGATGATCAATTCAATCTCGGTTAAAGATG
GAGAATTAATCACCCCCTCCAATGATCTCCTTATGCGGCTCTCTATAGTCG
ATAGCATTGAACGTTTGGGAATCGATAGGCATTTCAAAAGTGAAATAAAA
TCAGCTCTGGATTATGTTTACAGTTATTGGAACGAAAAAGGCATTGGGTG
GGGAAGAGATAGTGTTGTTGCCGATCTCAACTCAACTGCCTTGGGGCTTC
GAACTCTACGACTACACGGATACCCGGTGTCTTCAGATGTGTTACAGCACT
TCAAAGAACAAAAAGGGCAGTTTGCATGTTCGGCCATTCAAACAGAGGGA
GAGATAAGAAGTGTTCTCAACTTATTTCGGGCTTCCCAAATTGCCTTTCCG
GGAGAGAAAGTTATGGAAGAGGCAGAAGTCTTCTCTACAATATATTTAAA
AGAAGCCATACTAAAGCTTCCGGTCTGCGGTCTTTCACGAGAGATATCGT
ACGTTCTGGAATATGGTTGGCATATAAATTTGCCAAGATTGGAAGCAAGG
AACTACATCGACGTATTTGGACAGGACCCCATTTATTTGACGCCAAATATG
AAGACCCAAAAACTTCTAGAACTTGCAAAGTTGGAGTTCAATATGTTTCA
CTCTTTACAACAGCAAGAGCTAAAGCTTCTCTCCAGATGGTGGAAAGATT
CGGGTTTCTCTCAAATGACCTTCCCTCGGCATCGTCACGTGGAATATTACA

FIG.1H

CTTTGGCATCTTGCATTGATAGTGAACCTCAACATTCTTCGTTCAGACTTG
GATTTGCCAAAATGTTTCATCTTGCCACGGTTCTTGACGATATTTACGACA
CCTTTGGCACGATGGATGAGCTAGAACTCTTCACGGCGGCAGTTAAGAGG
TGGCATCCGTCTGCGACGGAGTGGCTTCCAGAATATATGAAAGGAGTATA
TATGGTGCTTTACGAAACCGTTAACGAAATGGCAGGAGAAGCAGAAAAGT
CTCAAGGCCGAGACACGCTCAACTATGCCCGAAATGCTTTGGAGGCTTAT
ATTGATGCTTCTATGAAAGAAGCGAAGTGGATTTTCAGTGGTTTTTGCCA
ACATTTGAGGAGTACCTGGATAACGGGAAAGTTAGTTTCGGTTATAGCAT
TGGCACATTGCAACCCATTCTGACGTTGGGCATTCCCTTTCCTCATCACAT
CCTACAAGAAATAGACTTTCCTTCCAGGCTCAATGATGTGGCATGTTCCAT
TCTCCGACTAAAAGGCGACATTCACACTTACGAGGCTGAGAGGAGCCGTG
GAGAAAAATCTTCGTGTATATCATGTTATATGGAAGAGAATCCCGAGTCA
ACAGAGGAAGATGCAATCAATCATATCAACTCCATGGTCGACAAATTACT
CAAGGAACTAAATTGGGAGTATCTGAGACCTGATAGCAATGTTCCAATCA
CTTCCAAGAAACATGCATTTGACATTCTGAGAGCTTTCTACCATCTCTACA
AATACCGAGATGGCTTCAGCGTTGCGAACTATGAAATAAAGAATTTGGTC
ATGACAACCGTCATTGAGCCTGTGCCTTTATAA- (SEQ ID NO:11)

P._coulteri_MBO--------------------------------------------------------------------------------
AGACGCATAGCTGGTCATCATTCCAACCTYTGGGACGATRATTTSATACAG
TCCCTYTCAACGCCTTATGGGGCAATTTCGTACCATGAAAGTGCTCAGAA
ACTTATTGGAGAAGTAAAAGAGATGATCAATTCAATCTCGGTTAAAGATG
GAGAATTAATCACCCCCTCCAATGATCTCCTTATGCGGCTCTCTATAGTTG
ATAGCATTGAACGTTTGGGAATCGATAGGCATTTCAAAAGTGAAATAAAA
TCAGCTCTGGATTATGTTTACAGTTATTGGAACGAAAAAGGCATTGGGTG
GGGAAGAGATAGTGTTGTTGCCGATCTCAACTCAACTGCCTTGGGGCTTC
GAACTCTACGACTACACGGATACCCGGTGTCTTCAGATGTGTTACAACACT
TCAAAGAACAAAAAGGGCAGTTTGCATGTTCGGCCATTCAAACAGAGGGA
GAGATAAGAAGTGTTCTCAACTTATTTCGGGCTTCCCAAATTGCCTTTCCG
GGAGAGAAAGTTATGGAAGAGGCAGAAGTCTTCTCTACAATATATTTAAA
AGAAGCCATACTAAAGCTTCCGGTCTGCGGTCTTTCACGAGAGATATCGT
ACGTTCTGGAATATGGTTGGCATATAAATTTGCCAAGATTGGAAGCAAGG
AACTACATCGACGTATTTGGAGAGGACCCCATTTATTTGACGCCAAATAT
GAAGACCCAAAAACTTCTAGAACTTGCAAAGTTGGAGTTCAATATGTTTC
ACTCTTTACAACAGCAAGAGCTAAAGCTTCTCTCCAGATGGTGGAAAGAT
TCGGGTTTCTCTCAAATGACCTTCCCTCGGCATCGTCACGTGGAATATTAC
ACTTTGGCATCTTGCATTGATAGTGAACCTCAACATTCTTCGTTCAGACTT
GGATTTGCCAAAATCTTTCATCTTGCCACGGTTCTTGACGATATTTACGAC
ACCTTTGGCACGATGGATGAGCTAGAACTCTTCACGGCGGCAGTTAAGAG
GTGGCATCCGTCTGCGACGGAGTGGCTTCCAGAATATATGAAAGGAGTAT
ATATGGTGCTTTACGAAACCGTTAACGAAATGGCAGGAGAAGCAGAAAA
GTCTCAAGGCCGAGACACGCTCAACTATGGCCGAAATGCTTTGGAGGCTT
ATATTGATGCTTCTATGGAAGAAGCGAAGTGGATTTTCAGTGGTTTTTGC
CAACATTTGAGGAGTACCTGGATAACGGGAAAGTTAGTTTCGGTTATGGC
ATTGGCACATTGCAACCCATTCTGACGTTGGGCATTCCCTTTCCTCATCAC
ATCCTACAAGAAATAGACTTTCCTTCCAGGCTCAATGATGTGGCATCTTCC
ATTCTCCGACTAAAAGGCGACATTCACACTTACCAGGCTGAGAGGAGCCG
TGGAGAAAAATCTTCGTGTATATCATGTTATATGGAAGAGAATCCCGAGT
CAACAGAGGAAGATGCAATCAATCATATCAACTCCATGGTCGACAAATTA
CTCAAGGAACTAAATTGGGAGTATCTGAGACCTGATAGCAATGTTCCAAT

FIG. 1I

CACTTCCAAGAAACATGCATTTGACATTCTGAGAGCTTTCTACCATCTCTA
CAAATACCGAGATGGCTTCAGCGTTGCGAACTATGAAATAAAGAATTTGG
TCATGACAACCGTCATTGAGCCTGTGCCTTTATAA- (SEQ ID NO:12)

P._torreyana_MBO-----------------------------------------------------------------------------------
AACCTCTGGGACGATGATTTGATACAGTCCCTTTCAACGCCTTATGGGGCA
ATTTCGTACCATGAAAGTGCTCAGAAACTTATTGGAGAAGTAAAAGAGAT
GATCAATTCAATCTCGGTTAAAGATGGAGAATTAATCACCCCCTCCAATG
ATCTCCTTATGCGGCTCTCTATAGTTGATAGCATTGAACGTTTGGGAATCG
ATAGGCATTTCAAAAGTGAAATAAAATCAGCTCTGGATTATGTTTACAGTT
ATTGGAACGAAAAAGGCATTGGGTGGGGAAGAGATAGTGTTGTTGCCGAT
CTCAACTCAACTGCCTTGGGGCTTCGAACTCTACGACTACACGGATACCCG
GTGTCTTCAGATGTGTTACAACACTTCAAAGAACAAAAAGGGCAGTTTGC
ATGTTCGGCCATTCAAACAGAGGGAGAGATAAGAAGTGTTCTCAACTTAT
TTCGGGCTTCCCAAATTGCCTTTCCGGGAGAGAAAGTTATGGAAGAGGCA
GAAGTCTTCTCTACAATGTATTTAAAAGAAGCCATACTAAAGCTTCCGGTC
TGCGGTCTTTCACGAGAGATATCGTACGTTCTGGAATATGGTTGGCATATA
AATTTGCCAAGATTGGAAGCAAGGAACTACATCGACGTATTTGGACAGGA
CCCCATTTATTTGACGCCAAATATGAAGACCCAAAAACTTCTAGAACTTGC
AAAGTTGGAGTTCAATATGTTTCACTCTTTACAACAGCAAGAGCTAAAGC
TTCTCTCCAGATGGTGGAAAGATTCGGGTTTCTCTCAAATGACCTTCCCTC
GGCATCGTCACGTGGAATATTACACTTTGGCATCTTGCATTGATAGTGAAC
CTCAACATTCTTCGTTCAGACTTGGATTTGCCAAAATCTTTCATCTTGCCAC
GGTTCTTGACGATATTTACGACACCTTTGGCACGATGGATGAGCTAGAACT
CTTCACGGCGGCAGTTAAGAGGTGGCATCCGTCTGCGACGGAGTGGCTTC
CAGAATATATGAAAGGAGTATATATGGTGCTTTACGAAACCGTTAACGAA
ATGGCAGGAGAAGCAGAAAAGTCTCAAGGCCGAGACACGCTCAACTATG
CCCGAAATGCTTTGGAGGCTTATATTGATGCTTCTATGGAAGAAGCGAAG
TGGATTTTCAGTGGTTTTTTGCCAACATTTGAGGAGTACCTGGATAACGGG
AAAGTTAGTTTCGGTTATGGCATTGGCACATTGCAACCCATTCTGACGTTG
GGCATTCCCTTTCCTCATCACATCCTACAAGAAATAGACTTTCCTTCCAGG
CTCAATGATGTGGCATCTTCCATTCTCCGACTAAAAGGCGACATTCACACT
TACCAGGCTGAGAGGAGCCGTGGAGAAAAATCTTCGTGTATATCATGTTA
TATGGAAGAGAATCCCGAGTCAACAGAGGAAGATGCAATCAATCATATCA
ACTCCATGGTCGACAAATTACTCAAGGAACTAAATTGGGAGTATCTGAGA
CCTGATAGCAATGTTCCAATCACTTCCAAGAAACATGCATTTGACATTCTG
AGAGCTTTCTACCATCTCTACAAATACCGAGATGGCTTCAGCGTTGCGAAC
TATGAAATAAAGAATTTGGTCATGACAACCGTCATTGAGCCTGTGCCTTTA
TAA- (SEQ ID NO:13)

P._attenuata_MBO----------------------------------------------------------------------------------
AGACGCAGAGGTGATTTCCATTCCAACCTCTGGGACGATAATTTCATACA
GTCCCTCTCAACGCCTTATGGGGCAATTTCGTACCATGAAAGTGCTCAGAA
ACTTATTGGAGAAGTAAAAGAGATGATCAATTCAATCTCGGATAAAGATG
GAGAATTAATCACCCCCTCCAATGATCTCCTTATGCTGCTCTCTATAGTCG
ATAGCATTGAACGTTTGGGAATCGATAGGCATTTCAAAAGTGAAATAAAA
TCAGCTCTGGATTATGTTTACAGTTATTGGAACGAAAAAGGCATTGGGTG
GGGAAGAGATAGTGTTGTTGCCGATCTCAACTCAACTGCCTTGGGGCTTC
GAACTCTACGACTACACGGATACCCGGTGTCTTCAGACGTGTTACAACAC
TTCAAAGAACAAAATGGGCAGTTTGCATGTTCGGCCATTCAAACAGAGGG

FIG. 1J

AGAGATAAGAAGTGTTCTCAACTTATTTCGGGCTTCCCAAATTGCCTTTCC
GGGAGAGAAAGTTATGGAAGAGGCAGAAGTCTTCTCTACAAAATATTTAA
AAGAAGCCATACTAAAGCTTCCGGTCTGCGGTCTTTCACGAGAGATATCG
TACGTTCTGGAATATGGTTGGCATATGAATTTGCCAAGATTGGAAGCAAG
GAACTACATCGACGTATTTGGACAGGACCCCATTTATTTGACGCCAAATAT
GAAGACCCAAAAACTTCTAGAACTTGCAAAGTTGGAGTTCAATATGTTTC
ACTCTTTACAACAGCAAGAGCTAAAGCTTCTCTCCAGATGGTGGAAAGAT
TCGGGTTTCTCTCAAATGACCTTCCCTCGGCATCGTCACGTGGAATATTAC
ACTTTGGCATCTTGCATTGATAGTGAACCTCAACATTCTTCGTTCAGACTT
GGATTTGCCAAAATATTTCATCTTGCCACGGTTCTTGACGATATTTACGAC
ACCTTTGGCACGATGGATGAGCTAGAACTCTTCACAGCGGCAGTTAAGAG
GTGGCATCCGTCTGCGACGGAGTGGCTTCCAGAATATATGAAAGGAGTAT
ATATGGTGCTTTACGAAACCGTTAACGAAATGGCAGGAGAAGCAGAAAA
GTCTCAAGGCCGAGACACGCTCAACTATGCCCGAAATGCTTTGGAGGCTT
ATATTGATGCTTCTATGGAAGAAGCGAAGTGGATTTTCAGTGGTTTTTGC
CAACATTTGAGGAGTACCTGGATAACGGGAAAGTTAGTTTCGGTTATACC
ATTGGCACATTGCAACCCATTCTGACGTTGGGCATTCCCTTTCCTCATCAC
ATCCTACAAGAAATAGACTTTCCTTCCAGGCTCAATGATGTGGCATGTTCC
ATTCTCCGACTAAAAGGCGACGTTCACACTTACCAGCCTGAGAGGAGCCG
TGGAGAAGAATCTTCGTGTATATCATGTTATATTGAAGAGAATCCCGAGT
CAACAGAGGAAGATGCAATCAATCATATCAACTCCATGGTCGACAAATTA
CTCAAGGAACTAAATTGGGAGTATCTGAGACCTGATAGCAATGTTCCAAT
CACTTCCAAGAAACATGCATTTGACATTCTGAGAGCTTTGTACCATCTCTA
CAAATACCGAGATGGCTACAGCGTTGCGAACTATGAAATAAAGAATTTGG
TCATGACAACCGTCATTGAGCCTGTGCCTTTATAA- (SEQ ID NO:14)

P._radiata_MBO-----------------------------------------------------------------------

AACCTCTGGGACGATGATTTGATACAGTCCCTTTCAACGCCTTATGGGGCA
ATTTCGTACCATGAAAGTGCTCAGAAACTTATTGGAGAAGTAAAAGAGAT
GATCAATTCAATCTCGGATAAAAATGGAGAATTAATCACCCCCTCCAATG
ATCTCCTTATGCGGCTCTCTATAGTCGATAGCATTGAACGTTTGGGAATCG
ATAGGCATTTCAAAAGTGAAATAAAATCAGCTCTGGATTATGTTTACAGTT
ATTGGAACGAAAAAGGCATTGGGTGGGGAAGAGATAGTGTTGTTGCCGAT
CTCAACTCAACTGCCTTGGGGCTTCGAACTCTACGACTACACGGATACCCG
GTGTCTTCAGACGTGTTACAACACTTCAAAGAACAAAATGGGCAGTTTGC
ATGTTCGGCCATTCAAACAGAGGGAGAGATAAGAAGTGTTCTCAACTTAT
TTCGGGCTTCCCAAATTGCCTTTCCGGGAGAGAAAGTTATGGAAGAGGCA
GAAGTCTTCTCTACAAAATATTTAAAAGAAGCCATACTAAAGCTTCCGGT
CTGCGGTCTTTCACGAGAGATATCGTACGTTCTGGAATATGGTTGGCATAT
GAATTTGCCAAGATTGGAAGCAAGGAACTACATCGACGTATTTGGACAGG
ACCCCATTTATTTGACGCCAAATATGAAGACCCAAAAACTTCTAGAACTT
GCAAAGTTGGAGTTCAATATGTTTCACTCTTTACAACAGCAAGAGCTAAA
GCTTCTCTCCAGATGGTGGAAAGATTCGGGTTTCTCTCAAATGACCTTCCC
TCGGCATCGTCACGTGGAATATTACACTTTGGCATCTTGCATTGATAGTGA
ACCTCAACATTCTTCGTTCAGACTTGGATTTGCCAAAATATTTCATCTTGC
CACGGTTCTTGACGATATTTACGACACCTTTGGCACGATGGATGAGCTAG
AACTCTTCACAGCGGCAGTTAAGAGGTGGCATCCGTCTGCGACGGAGTGG
CTTCCAGAATATATGAAAGGAGTATATATGGTGCTTTACGAAACCGTTAA
CGAAATGGCAGGAGAAGCAGAAAAGTCTCAAGGCCGAGACACGCTCAAC
TATGCCCGAAATGCTTTGGAGGCTTATATTGATGCTTCTATGGAAGAAGCG

FIG. 1K

AAGTGGATTTTCAGTGGTTTTTTGCCAACATTTGAGGAGTACCTGGATAAC
GGGAAAGTTAGTTTCGGTTATACCATTGGCACATTGCAACCCATTCTGACG
TTGGGCATTCCCTTTCCTCATCACATCCTACAAGAAATAGACTTTCCTTCC
AGGCTCAATGATGTGGCATGTTCCATTCTCCGACTAAAAGGCGACGTTCA
CACTTACCAGCCTGAGAGGAGCCGTGGAGAAGAATCTTCGTGTATATCAT
GTTATATGGAAGAGAATCCCGAGTCAACAGAGGAAGATGCAATCAATCAT
ATCAACTCCATGGTCGACAAATTACTCAAGGAACTAAATTGGGAGTATCT
GAGACCTGATAGCAATGTTCCAATCACTTCCAAGAAACATGCATTTGACA
TTCTGAGAGCTTTGTACCATCTCTACAAATACCGAGATGGCTACAGCGTTG
CGAACTATGAAATAAAGAATTTGGTCATGACAACTGTCATTGAGCCTGTG
CCTTTATAA- (SEQ ID NO:15)

P._contorta_MBO1
TCTAGCAAGGTTAAGGTTGTCCGCAGAACGATGTCAACTTCCATCCGCAT
GTGTCAGATAACCACTGTATCCGGTGAAGGCGTACAGAGACGCATAGCAA
ATCATCATTCCAACCTCTGGGACGATAATTTCATACAGTCCCTCTCAACGC
CTTATGGGGCAATTTCGTACCATGAAAGTGCTCAGAAACTTATTGGAGAA
GTAAAAGAGATGATCAATTCAATCTCGGTTAAAGATGGAGAATTAATCAC
CCCCTCCAATGATCTCCTTATGCGGCTCTCTATAGTCGATAGCATTGAACG
TTTGGGAATCGATAGGCATTTCAAAAGTGAAATAAAATCAGCTCTGGATT
ATGTTTACAGTTATTGGAACGAAAAAGGCATTGGGTGGGGAAGAGATAGT
GTTGTTGCCGATCTCAACTCAACTGCCTTGGGGCTTCGAACTCTACGACTA
CACGGATACCCGGTGTCTTCAGACGTGTTACAACACTTCAAAGAACAAAA
AGGGCAGTTTGCATGTTCGGCCATTCAAACAGAGGGAGAGATAAGAAGTG
TTCTCAACTTATTTCGGGCTTCCCAAATTGCCTTTCCGGGAGAGAAAGTTA
TGGAAGAGGCAGAAGTCTTCTCTACAAAATATTTAAAAGAAGCCATACTA
AAGCTTCCGGTCTGCGGTCTTTCACGAGAGATATCGTACGTTCTGGAATAT
GGTTGGCATATGAATTTGCCAAGATTGGAAGCAAGGAACTACATCGACGT
ATTTGGACAGGACCCCATTTATTTGACGCCAAATATGAAGACCCAAAAAC
TTCTAGAACTTGCTAAGTTGGAGTTCAATATGTTTCACTCTTTACAACAGC
AAGAGCTAAAGCTTCTCTCCAGATGGTGGAAAGATTCGGGTTTCTCTCAA
ATGACCTTCCCTCGGCATCGTCACGTGGAATATTACACTTTGGCATCTTGC
ATTGATAGTGAACCTCAACATTCTTCGTTCAGACTTGGATTTGCCAAAATA
TTTCATCTTGCCACGGTTCTTGACGATATTTACGACACCTTTGGCACGATG
GATGAGCTAGAACTCTTCACAGCGGCAGTTAAGAGGTGGCATCCGTCTGC
GACGGAGTGGCTTCCAGAATATATGAAAGGAGTATATATGGTGCTTTACG
AAACCGTTAACGAAATGGCAGGAGAAGCAGAAAAGTCTCAAGGCCGAGA
CACGCTCAACTATGCCCGAAATGCTTTGGAGGCTTATATTGATGCTTCTAT
GGAAGAAGCGAAGTGGATTTTCAGTGGTTTTTTGCCAACATTTGAGGAGT
ACCTGGATAACGGGAAAGTTAGTTTCGGTTATACCATTGGCACATTGCAA
CCCATTCTGACGTTGGGCATTCCCTTTCCTCATCACATCCTACAAGAAATA
GACTTTCCTTCCAGGCTCAATGATGTGGCATGTTCCATTCTCCGACTAAAA
GGCGACATTCACACTTACCAGCCTGAGAGGAGCCGTGGAGAAGAATCTTC
GTGTATATCATGTTATATGGAAGATAATCCCGAGTCAACAGAGGAAGATG
CAATCAATCATATCAACTCCATGGTCGACAAATTACTCAAGGAACTAAAT
TGGGAGTATCTGAGACCTGATAGCAATGTTCCAATCACTTCCAAGAAACA
TGCATTTGACATTCTGAGAGCTTTCTACCATCTCTACAAATACCGAGATGG
CTACAGCGTTGCGAACTATGAAATAAAGAATTTGGTCATGACAACTGTCA
TTGAGCCTGTGCCTTTATAA- (SEQ ID NO:16)

FIG.1L

P._contorta_MBO2
TCTAGCAAGGTTAAGGTTGTCCGCAGAACGATGTCAACTTCCATCCGCAT
GTGTCAGATAACCACTGTATCCGGTGAAGGCGTACAGAGACGCATAGCAA
ATCATCATTCCAACCTCTGGGACGATAATTTCATACAGTCCCTCTCAACGC
CTTATGGGGCAATTTCGTACCATGAAAGTGCTCAGAAACTTATTGGAGAA
GTAAAAGAGATGATCAATTCAATCTCGGTTAAAGATGGAGAATTAATCAC
CCCGTCCAATGATCTCCTTATGCGGCTCTCTATAGTCGATAGCATTGAACG
TTTGGGAATCGATAGGCATTTCAAAAGTGAAATAAAATCAGCTCTGGATT
ATGTTTACAGTTATTGGAACGAAAAAGGCATTGGGTGGGGAAGAGATAGT
GTTGTTGCCGATCTCAACTCAACTGCCTTGGGGCTTCGAACTCTACGACTA
CACGGATACCCGGTGTCTTCAGACGTGTTACAACACTTCAAAGAACAAAA
AGGGCAGTTTGCATGTTCGGCCATTCAAACAGAGGGAGAGATAAGAAGTG
TTCTCAACTTATTTCGGGCTTCCCAAATTGCCTTTCCGGGAGAGAAAGTTA
TGGAAGAGGCAGAAGTCTTCTCTACAAAATATTTAAAAGAAGCCATACTA
AAGCTTCCGGTCTGCGGTCTTTCACGAGAGATATCGTACGTTCTGGAATAT
GGTTGGCATATAAATTTGCCAAGATTGGAAGCAAGGAACTACATCGACGT
ATTTGGACAGGACCCCATTTATTTGACGCCAAATATGAAGACCCAAAAAC
TTCTAGAACTTGCAAAGTTGGAGTTCAATATGTTTCACTCTTTACAACAGC
AAGAGCTAAAGCTTCTCTCCAGATGGTGGAAAGATTCGGGTTTCTCTCAA
ATGACCTTCCCTCGGCATCGTCACGTGGAATATTACACTTTGGCATCTTGC
ATTGATAGTGAACCTCAACATTCTTCGTTCAGACTTGGATTTGCCAAAATA
TTTCATCTTGCCACGGTTCTTGACGATATTTACGACACCTTTGGCACGATG
GATGAGCTAGAACTCTTCACAGCGGCAGTTAAGAGGTGGCATCCGTCTGC
GACGGAGTGGCTTCCAGAATATATGAAAGGAGTATATATGGTGCTTTACG
AAACCGTTAACGAAATGGCAGGAGAAGCAGAAAAGTCTCAAGGCCGAGA
CACGCTCAACTATGCCCGAAATGCTTTGGAGGCTTATATTGATGCTTCTAT
GGAAGAAGCGAAGTGGATTTTCAGTGGTTTTTTGCCAACATTTGAGGAGT
ACCTGGATAACGGGAAAGTTAGTTTCGGTTATACCATTGGCACATTGCAA
CCCATTCTGACGTTGGGCATTCCCTTTCCTCATCACATCCTACAAGAAATA
GACTTTCCTTCCAGGCTCAATGATGTGGCATGTTCCATTCTCCGACTAAAA
GGCGACGTTCACACTTACCAGGCTGAGAGGAGCCGTGGAGAAGAATCTTC
GTGTATATCATGTTATATGGAAGATAATCCCGAGTCAACAGAGGAAGATG
CAATCAATCATATCAACTCCATGGTCGACAAATTACTCAAGGAACTAAAT
TGGGAGTATCTGAGACCTGATAGCAATGTTCCAATCACTTCCAAGAAACA
TGCATTTGACATTCTGAGAGCTTTCTACCATCTCTACAAATACCGAGATGG
CTACAGCGTTGCGAACTATGAAATAAAGAATTTGGTCATGACAACTGTCA
TTGAGCCTGTGCCTTTATAA-(SEQ ID NO:17)

FIG. 1M

P._patula_MBO_translation_frame_+1
SSKVKVVRRTISTSIRMCRITTVSGEGVQRRIANHHSNLWDDNFIQSLSTPYGA
ISYHESAQKLIGEVKEMINSISVKDGELITPSNDLLMRLSIVDSIERLGIDRHFKS
EIKSALDYVYSYWNEKGIGWGRDSVVADLNSTALGLRTLRLHGYPVSSDVL
QHFKEQKGQFACSAIQTEGEIRSVLNLFRASQIAFPGEKVMEEAEVFSTIYLKE
AILKLPVCGLSREISYVLEYGWHINLPRLEARNYIDVFGQDPIYLTPNMKTQKL
LELAKLEFNMFHSLQQQELKLLSRWWKDSGFSQMTFPRHRHVEYYTLASCID
SEPQHSSFRLGFAKIFHLATVLDDIYDTFGTMDELELFTAAVERWHPSATEWL
PEYMKGVYMVLYETVNEMAGEAEKSQGRDTLNYARNALEAYIDASMKEAK
WIFSGFLPTFEEYLDNGKVSFGYSIGTLQPILTLGIPFPHHILQEIDFPSRLNDVA
CSILRLKGDIHTYQAERSRGEKSSCISCYMEENPESTEEDAIDHINSMVDKLLK
ELNREYLRPDSNVPITSKKHAFDILRAFYHLYKYRDGFSVANYEIKNLVMTTV
IEPVPL(SEQ ID NO:18)

P._pseudostrobus_estevezii_translation_frame_+1
SSKVKVVRRTISTSIRMCRITTVSGEGVQRRIANHHSNLWDDNFIQSLSTPYGA
ISYHESAQKLIGEVKEIINSISVKDGELITPSNDLLMRLSIVDSIERLGIDRHFKSE
IKSALDYVYSYWNEKGIGWGRDSVVADLNSTALGLRTLRLHGYPVSSDVLQ
HFKEQKGQFACSAIQTEGEIRSVLNLFRASQIAFPGEKVMEEAEVFSTIYLKEA
ILKLPVCGLSREISYVLEYGWHINLPRLEARNYIDVFGQDPIYLTPNMKTQKLL
ELAKLEFNMFHSLQQQELKLLSRWWKDSGFSQMTFPRHRHVEYYTLASCIDS
EPQHSSFRLGFAKIFHLATVLDDIYDTFGTMDELELFTAAVKRWHPSATEWLP
EYMKGVYMVLYETVNEMAGEAEKSQGRDTLNYARNALEAYIDASMKEAK
WIFSGFLPTFEEYLDNGKVSFGYSIGTLQPILTLGIPFPHHILQEIDFPSRLNDVA
CSILRLKGDIHTYQAERSRGEKSSCISCYMEENPESTEEDAINHVNSMVDKLL
KELNWEYLRPDSNVPITSKKHAFDILRAFYHLYKYRDGFSVANYEIKNLVMT
TVIEPVPL (SEQ ID NO:19)

P_cooperi_ornelasi_MBO_translation_frame_+1
SSKVKVVRRTISTSIRMCRITTVSGEGVQRRIANHHSNLWDDNFIQSLSTPYGA
ISYHESAQKLIGEVKEMINSISVKDGELITPSNDLLMRLSIVDSIERLGIDRHFKS
EIKSALDYVYSYWNEKGIGWGRDSVVADLNSTALGLRTLRLHGYPVSSDVL
QHFKEQKGQFACSAIQTEGEIRSVLNLFRASQIAFPGEKVMEEAEVFSTIYLKE
AILKLPVCGLSREISYVLEYGWHINLPRLEARNYIDVFGQDPIYLTPNMKTQKL
LELAKLEFNMFHSLQQQELKLLSRWWKDSGFSQMTFPRHRHVEYYTLASCID
SEPQHSSFRLGFAKIFHLATVLDDIYDTFGTMDELELFTAAVKRWHPSATEWL
PEYMKGVYMVLYETVNEMAGEAEKSQGRDTLNYARNALEAYIDASMKEAK
WIFSGFLPTFEEYLDNGKVSFGYSIGTLQPILTLGIPFPHHILQEIDFPSRLNDVA
CSILRLKGDIHTYQAERSRGEKSSCISCYMEENPESTEEDAINHINSMVDKLLK
ELNWEYLRPDSNVPITSKKHAFDILTAFYHLYKYRDGFSVANYEIKNLVMTT
VIEPVPL (SEQ ID NO:20)

P._hartwegii_MBO_translation_frame_+1
SSKVKVVRRTISTSIRMCRITTVSGEGVQRRIANHHSNLWDDNFIQSLSTPYGA
ISYHESAQKLIGEVKEMINSISVKDGELITPSNDLLMRLSIVDSIERLGIDRHFKS
EIKSALDYVYSYWNEKGIGWGRDSVVADLNSTALGLRTLRLHGYPVSSDVL
QHFKEQKGQFACSAIQTEGEIRSVLNLFRASQIAFPGEKVMEEAEVFSTIYLKE

FIG. 2A

AILKLPVCGLSREISYVLEYGWHINLPRLEARNYIDVFGQDPIYLTPNMKTQKL
LELAKLEFNMFHSLQQQELKLLSRWWKDSGFSQMTFPRHRHVEYYTLASCID
SEPQYSSFRLGFAKIFHILATVLDDIYDTFGTMDELELFTAAVKRWHPSATEWL
PEYMKGVYMVLYETVNEMAGEAEKSQGRDTLNYARNALEAYIDASMKEAK
WIFSGFLPTFEEYLDNGKVSFGYSIGTLQPILTLGIPFPHHILQEIDFPSRLNDVA
CSILRLKGDIHTYQAERSRGEKSSCISCYMEENPESTEEDAINHINSMVDKLLK
ELNWEYLRPDSNVPITSKKHAFDILRAFYHLYKYRDGFSVANYEIKNLVMTT
VIEPVPL (SEQ ID NO:21)

P._ponderosa_MBO1_translation_frame_+1
SSKVKVVRRTISTSIRMCRITTESGEGVQRRIANHHSNLWDDNFIQSLSTPYGA
ISYHESAQKLIGEVKEMINSISLKDGELITPSNDLLMRLSIVDSIERLGIDRHFKS
EIKSALDYVYSYWNEKGIGWGRDSVVADLNSTALGLRTLRLHGYPVSSDVL
QHFKEQKGQFACSAIQTEGEIRSVLNLFRASQIAFPGEKVMEEAEVFSTIYLKE
AILKLPVCGLSREISYVLEYGWHINLPRLEARNYIDVFGQDPIYLTPNMKTQKL
LELAKLEFNMFHSLQQQELKLLSRWWKDSGFSQMTFPRHRHVEYYTLASCID
SEPQHSSFRLGFAKIFHLATVLDDIYDTFGTMDELELFTAAVKRWHPSATEWL
PEYMKGVYMVLYETVNEMAREAEKSQGRDTLNYARNALEAYIDASMKEAK
WIFSGFLPTFEEYLDNGKVSFGYSIGTLQPILTLGIPFPHHILQEIDFPSRLNDVA
CSILRLKGDIHTYQAERSRGEKSSCISCYMEENPESTEEDAINHINSMVDKLLK
ELNWEYLRPDSNVPITSKKHAFDILRTFYHLYKYRDGFSVANYEIKNLVMTT
VIEPVPL (SEQ ID NO:22)

P._ponderosa_MBO2_translation_frame_+1
SSKVKVVRRTISTSIRMCRITTESGEGVQRRIANHHSNLWDDNFIQSLSTPYGA
ISYHESAQKLIGEVKEMINSISLKDGELITPSNDLLMRLSIVDSIERLGIDRHFKS
EIKSALDYVYSYWNEKGIGWGRDSVVADLNSTALGLRTLRLHGYPVSSDVL
QHFKEQKGQFACSAIQTEGEIRSVLNLFRASQIAFPGEKVMEEAEVFSTIYLKE
AILKLPVCGLSREISYVLEYGWHINLPRLEARNYIDVFGQDPIYLTPNMKTQKF
LELAKLEFNMFHSLQQQELKLLSRWWKDSGFSQMTFPRHRHVEYYTLASCID
SEPQHSSFRLGFAKIFHLATVLDDIYDTFGTMDELELFTAAVKRWHPSATEWL
PEYMKGVYMVLYETVNEMAREAEKSQGRDTLNYARNALEAYIDASMKEAK
WIFSGFLPTFEEYLYNGKVSFGYSIGTLQPILTLGIPFPHHILQEIDFPSRLNDVA
CSILRLKGDIHTYQAERSRGEKSSCISCYMEENPESTEEDAINHINSMVDKLLK
ELNWEYLRPDSNVPITSKKHAFDILRTFYHLYKYRDGFSVANYEIKNLVMTT
VIEPVPL (SEQ ID NO:23)

P._jeffreyi_MBO_translation_frame_+1
SSKVKVVRRTISTSIRMCRITTESGEGVQRRIANHHSNLWDDNFIQSLSTPYGA
ISYHESAQKLIGEVKEMINSISLKDGELITPSNDLLMRLSIVDSIERLGIDRHFKS
EIKSALDYVYSYWNEKGIGWGRDSVVADLNSTALGLRTLRLHGYPVSSDVL
QHFKEQKGQFACSAIQTEGEIRSVLNLFRASQIAFPGEKVMEEAEVFSTIYLKE
AILKLPVCGLSREISYVLEYGWHINLPRLEARNYIDVFGQDPIYLTPNMKTQKL
LELAKLEFNMFHSLQQQELKLLSRWWKDSGFSQMTFPRHRHVEYYTLASCID
SEPQHSSFRLGFAKIFHLATVLDDIYDTFGTMDELELFTAAVKRWHPSATEWL
PEYMKGVYMVLYETVNEMAGEAEKSQGRDTLNYARNASEAYIDASMKEAK
WIFSGFLPTFEEYLDNGKVSFGYSIGTLQPILTLGIPFPHHILQEIDFPSRLNDVA
CSILRLKGDIHTYQAERSRGEKSSCISCYMEENPESTEEDAINHINSMVDKLLK
ELNWEYLRPDSNVPITSKKHAFDILRAFYHLYKYRDGFSVANYEIKNLVMTT
VIEPVPL (SEQ ID NO:24)

FIG.2B

P._montezumae_MBO_translation_frame_+1
SSKVKVVRRTISTSIRMCRITTVSGEGVQRRIANHHSNLWDDNFIQSLSTPYGA
ISYHESAQKLIGEVKEMINSISVKDGELITPSNDLLMRLSIVDSIERLGIDRHFKS
EIKSALDYVYSYWNEKGIGWGRDSVVADLNSTALGLRTLRLHGYPVSSDVL
QHFKEQKGQFACSAIQTEGEIRSVLNLFRASQIAFPGEKVMEEAEVFSTIYLKE
AILKLPVCGLSREISYVLEYGWHINLPRLEARNYIDVFGQDPIYLTPNMKTQKL
LELAKLEFNMFHSLQQQELKLLSRWWKDSGFSQMTFPRHRHVEYYTLASCID
SEPQHSSFRLGFAKMFHLATVLDDIYDTFGTMDELELFTAAVKRWHPSATEW
LPEYMKGVYMVLYETVNEMAGEAEKSQGRDTLNYARNALEAYIDASMKEA
KWIFSGFLPTFEEYLDNGKVSFGYSIGTLQPILTLGIPFPHHILQEIDFPSRLNDV
ACSILRLKGDIHTYEAERSRGEKSSCISCYMEENPESTEEDAINHINSMVDKLL
KELNWEYLRPDSNVPITSKKHAFDILRAFYHLYKYRDGFSVANYEIKNLVMT
TVIEPVPL (SEQ ID NO:25)

P._pseudostrobus_MBO_translation_frame_+1 --------------------------------
RRXXXXHSNLWDDNFIQSLSTPYGAISYHESAQKLIGEVKEMINSISVKDGELI
TPSNDLLMRLSIVDSIERLGIDRHFKSEIKSALDYVYSYWNEKGIGWGRDSVV
ADLNSTALGLRTLRLHGYPVSSDVLQHFKEQKGQFACSAIQTEGEIRSVLNLF
RASQIAFPGEKVMEEAEVFSTIYLKEAILKLPVCGLSREISYVLEYGWHINLPR
LEARNYIDVFGQDPIYLTPNMKTQKLLELAKLEFNMFHSLQQQELKLLSRWW
KDSGFSQMTFPRHRHVEYYTLASCIDSEPQHSSFRLGFAKMFHLATVLDDIYD
TFGTMDELELFTAAVKRWHPSATEWLPEYMKGVYMVLYETVNEMAGEAEK
SQGRDTLNYARNALEAYIDASMKEAKWIFSGFLPTFEEYLDNGKVSFGYSIGT
LQPILTLGIPFPHHILQEIDFPSRLNDVACSILRLKGDIHTYEAERSRGEKSSCISC
YMEENPESTEEDAINHINSMVDKLLKELNWEYLRPDSNVPITSKKHAFDILRA
FYHLYKYRDGFSVANYEIKNLVMTTVIEPVPL (SEQ ID NO:26)

P._sabiniana_MBO1_translation_frame_+1
SSKVKVVRRTISTSIRMCRITTESGEGVQRRIANHHSNLWDDNFIQSLSTPYGA
ISYHESAQKLIGEVKEMINSISVKDGELITPSNDLLMRLSIVDSIERLGIDRHFKS
EIKSALDYVYSYWNEKGIGWGRDSVVADLNSTALGLRTLRLHGYPVSSDVL
QHFKEQKGQFACSAIQTEGEIRSVLNLFRASQIAFPGEKVMEEAEVFSTIYLKE
AILKLPVCGLSREISYVLEYGWHINLPRLEARNYIDVFGEDPIYLTPNMKTQKL
LELAKLEFNMFHSLQQQELKLLSRWWKDSGFSQMTFPRHRHVEYYTLASCID
SEPQHSSFRLGFAKIFHLATVLDDIYDTFGTMDELELFTAAVKRWHPSATEWL
PEYMKGVYMVLYETVNEMAGEAEKSQGRDTLNYGRNALEAYIDASMEEAK
WIFSGFLPTFEEYLDNGKVSFGYGIGTLQPILTLGIPFPHHILQEIDFPSRLNDVA
SSILRLKGDIHTYQAERSRGEKSSCISCYMEENPESTEEDAINHINSMVDKLLK
ELNWEYLRPDSNVPITSKKHAFDILRAFYHLYKYRDGFSVANYEIKNLVMTT
VIEP--- (SEQ ID NO:27)

P._sabiniana_MBO2_translation_frame_+1
SSKVKVVRRTISTSIRMCRITTESGEGVQRRIANHHSNLWDDNFIQSLSTPYGA
ISYHESAQKLIGEVKEMINSISLKDGELITPSNDLLMRLSIVDSIERLGIDRHFKS
EIKSALDYVYSYWNEKGIGWGRDSVVADLNSTALGLRTLRLHGYPVSSDVL
QHFKEQKGQFACSAIQTEGEIRSVLNLFRASQIAFPGEKVMEEAEVFSTIYLKE
AILKLPVCGLSREISYVLEYGWHINLPRLEARNYIDVFGEDPIYLTPNMKTQKL
LELAKLEFNMFHSLQQQELKLLSRWWKDSGFSQMTFPRHRHVEYYTLASCID
SEPQHSSFRLGFAKIFHLATVLDDIYDTFGTMDELELFTAAVKRWHPSATEWL

FIG. 2C

PEYMKGVYMVLYETVNEMAGEAEKSQGRDTLNYGRNALEAYIDASMEEAK
WIFSGFLPTFEEYLDNGKVSFGYGIGTLQPILTLGIPFPHHILQEIDFPSRLNDVA
SSILRLKGDIHTYQAERSRGEKSSCISCYMEENPESTEEDAINHINSMVDKLLK
ELNWEYLRPDSNVPITSKKHAFDILRAFYHLYKYRDGFSVANYEIKNLVMTT
VIEPVPL (SEQ ID NO:28)

P._coulteri_MBO_translation_frame_+1 ------------------------------
RRIAGHHSNLWDDBXIQSLSTPYGAISYHESAQKLIGEVKEMINSISVKDGELI
TPSNDLLMRLSIVDSIERLGIDRHFKSEIKSALDYVYSYWNEKGIGWGRDSVV
ADLNSTALGLRTLRLHGYPVSSDVLQHFKEQKGQFACSAIQTEGEIRSVLNLF
RASQIAFPGEKVMEEAEVFSTIYLKEAILKLPVCGLSREISYVLEYGWHINLPR
LEARNYIDVFGEDPIYLTPNMKTQKLLELAKLEFNMFHSLQQQELKLLSRWW
KDSGFSQMTFPRHRHVEYYTLASCIDSEPQHSSFRLGFAKIFHLATVLDDIYDT
FGTMDELELFTAAVKRWHPSATEWLPEYMKGVYMVLYETVNEMAGEAEKS
QGRDTLNYGRNALEAYIDASMEEAKWIFSGFLPTFEEYLDNGKVSFGYGIGTL
QPILTLGIPFPHHILQEIDFPSRLNDVASSILRLKGDIHTYQAERSRGEKSSCISC
YMEENPESTEEDAINHINSMVDKLLKELNWEYLRPDSNVPITSKKHAFDILRA
FYHLYKYRDGFSVANYEIKNLVMTTVIEPVPL (SEQ ID NO:29)

P._torreyana_MBO_translation_frame_+1 --------------------------------------
NLWDDDLIQSLSTPYGAISYHESAQKLIGEVKEMINSISVKDGELITPSNDLLM
RLSIVDSIERLGIDRHFKSEIKSALDYVYSYWNEKGIGWGRDSVVADLNSTAL
GLRTLRLHGYPVSSDVLQHFKEQKGQFACSAIQTEGEIRSVLNLFRASQIAFPG
EKVMEEAEVFSTMYLKEAILKLPVCGLSREISYVLEYGWHINLPRLEARNYID
VFGQDPIYLTPNMKTQKLLELAKLEFNMFHSLQQQELKLLSRWWKDSGFSQ
MTFPRHRHVEYYTLASCIDSEPQHSSFRLGFAKIFHLATVLDDIYDTFGTMDE
LELFTAAVKRWHPSATEWLPEYMKGVYMVLYETVNEMAGEAEKSQGRDTL
NYARNALEAYIDASMEEAKWIFSGFLPTFEEYLDNGKVSFGYGIGTLQPILTL
GIPFPHHILQEIDFPSRLNDVASSILRLKGDIHTYQAERSRGEKSSCISCYMEEN
PESTEEDAINHINSMVDKLLKELNWEYLRPDSNVPITSKKHAFDILRAFYHLY
KYRDGFSVANYEIKNLVMTTVIEPVPL (SEQ ID NO:30)

P._attenuata_MBO_translation_frame_+1 ------------------------------
RRRGDFHSNLWDDNFIQSLSTPYGAISYHESAQKLIGEVKEMINSISDKDGELI
TPSNDLLMLLSIVDSIERLGIDRHFKSEIKSALDYVYSYWNEKGIGWGRDSVV
ADLNSTALGLRTLRLHGYPVSSDVLQHFKEQNGQFACSAIQTEGEIRSVLNLF
RASQIAFPGEKVMEEAEVFSTKYLKEAILKLPVCGLSREISYVLEYGWHMNLP
RLEARNYIDVFGQDPIYLTPNMKTQKLLELAKLEFNMFHSLQQQELKLLSRW
WKDSGFSQMTFPRHRHVEYYTLASCIDSEPQHSSFRLGFAKIFHLATVLDDIY
DTFGTMDELELFTAAVKRWHPSATEWLPEYMKGVYMVLYETVNEMAGEAE
KSQGRDTLNYARNALEAYIDASMEEAKWIFSGFLPTFEEYLDNGKVSFGYTIG
TLQPILTLGIPFPHHILQEIDFPSRLNDVACSILRLKGDVHTYQPERSRGEESSCI
SCYIEENPESTEEDAINHINSMVDKLLKELNWEYLRPDSNVPITSKKHAFDILR
ALYHLYKYRDGYSVANYEIKNLVMTTVIEPVPL (SEQ ID NO:31)

P._radiata_MBO_translation_frame_+1 --------------------------------------
NLWDDDLIQSLSTPYGAISYHESAQKLIGEVKEMINSISDKNGELITPSNDLLM
RLSIVDSIERLGIDRHFKSEIKSALDYVYSYWNEKGIGWGRDSVVADLNSTAL
GLRTLRLHGYPVSSDVLQHFKEQNGQFACSAIQTEGEIRSVLNLFRASQIAFPG
EKVMEEAEVFSTKYLKEAILKLPVCGLSREISYVLEYGWHMNLPRLEARNYI

FIG. 2D

DVFGQDPIYLTPNMKTQKLLELAKLEFNMFHSLQQQELKLLSRWWKDSGFS
QMTFPRHRHVEYYTLASCIDSEPQHSSFRLGFAKIFHLATVLDDIYDTFGTMD
ELELFTAAVKRWHPSATEWLPEYMKGVYMVLYETVNEMAGEAEKSQGRDT
LNYARNALEAYIDASMEEAKWIFSGFLPTFEEYLDNGKVSFGYTIGTLQPILTL
GIPFPHHILQEIDFPSRLNDVACSILRLKGDVHTYQPERSRGEESSCISCYMEEN
PESTEEDAINHINSMVDKLLKELNWEYLRPDSNVPITSKKHAFDILRALYHLY
KYRDGYSVANYEIKNLVMTTVIEPVPL (SEQ ID NO:32)

P._contorta_MBO1_translation_frame_+1
SSKVKVVRRTMSTSIRMCQITTVSGEGVQRRIANHHSNLWDDNFIQSLSTPYG
AISYHESAQKLIGEVKEMINSISVKDGELITPSNDLLMRLSIVDSIERLGIDRHF
KSEIKSALDYVYSYWNEKGIGWGRDSVVADLNSTALGLRTLRLHGYPVSSDV
LQHFKEQKGQFACSAIQTEGEIRSVLNLFRASQIAFPGEKVMEEAEVFSTKYL
KEAILKLPVCGLSREISYVLEYGWHMNLPRLEARNYIDVFGQDPIYLTPNMKT
QKLLELAKLEFNMFHSLQQQELKLLSRWWKDSGFSQMTFPRHRHVEYYTLA
SCIDSEPQHSSFRLGFAKIFHLATVLDDIYDTFGTMDELELFTAAVKRWHPSAT
EWLPEYMKGVYMVLYETVNEMAGEAEKSQGRDTLNYARNALEAYIDASME
EAKWIFSGFLPTFEEYLDNGKVSFGYTIGTLQPILTLGIPFPHHILQEIDFPSRLN
DVACSILRLKGDIHTYQPERSRGEESSCISCYMEDNPESTEEDAINHINSMVDK
LLKELNWEYLRPDSNVPITSKKHAFDILRAFYHLYKYRDGYSVANYEIKNLV
MTTVIEPVPL (SEQ ID NO:33)

P._contorta_MBO2_translation_frame_+1
SSKVKVVRRTMSTSIRMCQITTVSGEGVQRRIANHHSNLWDDNFIQSLSTPYG
AISYHESAQKLIGEVKEMINSISVKDGELITPSNDLLMRLSIVDSIERLGIDRHF
KSEIKSALDYVYSYWNEKGIGWGRDSVVADLNSTALGLRTLRLHGYPVSSDV
LQHFKEQKGQFACSAIQTEGEIRSVLNLFRASQIAFPGEKVMEEAEVFSTKYL
KEAILKLPVCGLSREISYVLEYGWHINLPRLEARNYIDVFGQDPIYLTPNMKTQ
KLLELAKLEFNMFHSLQQQELKLLSRWWKDSGFSQMTFPRHRHVEYYTLAS
CIDSEPQHSSFRLGFAKIFHLATVLDDIYDTFGTMDELELFTAAVKRWHPSAT
EWLPEYMKGVYMVLYETVNEMAGEAEKSQGRDTLNYARNALEAYIDASME
EAKWIFSGFLPTFEEYLDNGKVSFGYTIGTLQPILTLGIPFPHHILQEIDFPSRLN
DVACSILRLKGDVHTYQAERSRGEESSCISCYMEDNPESTEEDAINHINSMVD
KLLKELNWEYLRPDSNVPITSKKHAFDILRAFYHLYKYRDGYSVANYEIKNL
VMTTVIEPVPL (SEQ ID NO:34)

FIG.2E

SEQUENCE LISTING

```
<160> NUMBER OF SEQ ID NOS: 34

<210> SEQ ID NO 1
<211> LENGTH: 1782
<212> TYPE: DNA
<213> ORGANISM: Pinus pseudostrobus

<400> SEQUENCE: 1

tctagcaagg ttaaggttgt ccgcagaacg atctcaactt ccatccgcat gtgtcggata     60

accactgtat ccggtgaagg cgtacagaga cgcatagcaa atcatcattc caacctctgg    120

gacgataatt tcatacagtc cctctcaacc ccttatgggg caatttcgta ccatgaaagt    180

gctcagaaac ttattggaga agtaaaagag ataatcaatt caatctcggt taaagatgga    240

gaattaatca ccccctccaa tgatctcctt atgcggctct ctatagtcga tagcattgaa    300

cgtttgggaa ttgataggca tttcaaaagt gaaataaaat cagctctgga ttacgtttac    360

agttattgga acgaaaaagg cattgggtgg ggaagagata gtgttgttgc cgatctcaac    420

tcaactgcct tggggcttcg aactctacga ctacacggat acccggtgtc ttcagatgtg    480

ttacaacact tcaaagaaca aaaagggcag tttgcatgtt cggccattca aacagaggga    540

gagataagaa gtgttctcaa cttatttcgg gcttcccaaa ttgcctttcc gggagagaaa    600

gttatggaag aggcagaagt cttctctaca atatatttaa aagaagccat actaaagctt    660

ccggtctgcg gtctttcacg agagatatcg tacgttctgg aatatggttg gcatataaat    720

ttgccaagat tggaagcaag gaactacatc gacgtatttg gacaggaccc catttatttg    780

acgccaaata tgaagaccca aaaacttcta gaacttgcaa agttggagtt caatatgttt    840

cactctttac aacagcaaga gctaaagctt ctctccagat ggtggaaaga ttcgggtttc    900

tctcaaatga ccttccctcg gcatcgtcac gtggaatatt acactttggc atcttgcatt    960

gatagtgaac ctcaacattc ttcgttcaga cttggatttg ccaaaatctt tcatcttgcc   1020

acggttcttg acgatattta cgacaccttt ggcacgatgg atgagctaga actcttcacg   1080

gcggcagtta agaggtggca tccgtctgcg acggagtggc ttccagaata tatgaaagga   1140

gtatatatgg tgctttacga aaccgttaac gaaatggcag gagaagcaga aaagtctcaa   1200

ggccgagaca cgctcaacta tgcccgaaat gctttggagg cttatattga tgcttctatg   1260

aaagaagcga agtggatttt cagtggtttt ttgccaacat ttgaggagta cctggataac   1320

gggaaagtta gtttcggtta tagcattggc acattgcaac ccattctgac gttgggcatt   1380

ccctttcctc atcacatcct acaagaaata gactttcctt ccaggctcaa tgatgtggca   1440

tgttccattc tccgactaaa aggcgacatt cacacttacc aggctgagag gagccgtgga   1500

gaaaaatctt cgtgtatatc atgttatatg gaagagaatc ccgagtcaac agaggaagat   1560
```

-continued

```
gcaatcaatc atgtcaactc catggtcgac aaattactca aggaactaaa ttgggagtat   1620

ctgagacctg atagcaatgt tccaatcact tccaagaaac atgcatttga cattctgaga   1680

gctttctacc atctctacaa ataccgagat ggcttcagcg ttgcgaacta tgaaataaag   1740

aatttggtca tgacaaccgt cattgagcct gtgcctttat aa                      1782
```

<210> SEQ ID NO 2
<211> LENGTH: 1782
<212> TYPE: DNA
<213> ORGANISM: Pinus cooperi

<400> SEQUENCE: 2

```
tctagcaagg ttaaggttgt ccgcagaacg atctcaactt ccatccgcat gtgtcggata     60

accactgtat ccggtgaagg cgtacagaga cgcatagcaa atcatcattc caacctctgg    120

gacgataatt tcatacagtc cctctcaacg ccttatgggg caatttcgta ccatgaaagt    180

gctcagaaac ttattggaga agtaaaagag atgatcaatt caatctcggt taaagatgga    240

gaattaatca ccccctccaa tgatctcctt atgcggctct ctatagtcga tagcattgaa    300

cgtttgggaa tcgataggca tttcaaaagt gaaataaaat cagctctgga ttatgtttac    360

agttattgga acgaaaaagg cattgggtgg ggaagagata gtgttgttgc cgatctcaac    420

tcaactgcct tggggcttcg aactctacga ctacacggat acccggtgtc ttcagatgtg    480

ttacaacact tcaaagaaca aaaagggcag tttgcatgtt cggccattca aacagaggga    540

gagataagaa gtgttctcaa cttatttcgg gcttcccaaa ttgcctttcc gggagagaaa    600

gttatggaag aggcagaagt cttctctaca atatatttaa aagaagccat actaaagctt    660

ccggtctgcg gtctttcacg agagatatcg tacgttctgg aatatggttg gcatataaat    720

ttgccaagat tggaagcaag gaactacatc gacgtatttg gacaggaccc catttatttg    780

acgccaaata tgaagaccca aaaacttcta gaacttgcaa agttggagtt caatatgttt    840

cactctttac aacagcaaga gctaaagctt ctctccagat ggtggaaaga ttcgggtttc    900

tctcaaatga ccttccctcg gcatcgtcac gtggaatatt acactttggc atcttgcatt    960

gatagtgaac ctcaacattc ttcgttcaga cttggatttg ccaaaatctt tcatcttgcc   1020

acggttcttg acgatattta cgacaccttt ggcacgatgg atgagctaga actcttcacg   1080

gcggcagtta agaggtggca tccgtctgcg acggagtggc ttccagaata tatgaaagga   1140

gtatatatgg tgctttacga aaccgttaac gaaatggcag gagaagcaga aaagtctcaa   1200

ggccgagaca cgctcaacta tgcccgaaat gctttggagg cttatattga tgcttctatg   1260

aaagaagcga agtggatttt cagtggtttt ttgccaacat ttgaggagta cctggataac   1320

gggaaagtta gtttcggtta tagcattggc acattgcaac ccattctgac gttgggcatt   1380

ccctttcctc atcacatcct acaagaaata gactttcctt ccaggctcaa tgatgtggca   1440

tgttccattc tccgactaaa aggcgacatt cacacttacc aggctgagag gagccgtgga   1500

gaaaaatctt cgtgtatatc atgttatatg gaagagaatc ccgagtcaac agaggaagat   1560

gcaatcaatc atatcaactc catggtcgac aaattactca aggaactaaa ttgggagtat   1620

ctgagacctg atagcaatgt tccaatcact tccaagaaac atgcatttga cattctgaca   1680

gctttctacc atctctacaa ataccgagat ggcttcagcg ttgcgaacta tgaaataaag   1740

aatttggtca tgacaaccgt cattgagcct gtgcctttat aa                      1782
```

<210> SEQ ID NO 3
<211> LENGTH: 1782

<212> TYPE: DNA
<213> ORGANISM: Pinus hartwegii

<400> SEQUENCE: 3

```
tctagcaagg ttaaggttgt ccgcagaacg atctcaactt ccatccgcat gtgtcggata     60
accactgtat ccggtgaagg cgtacagaga cgcatagcaa atcatcattc caacctctgg    120
gacgataatt tcatacagtc cctctcaacg ccttatgggg caatttcgta ccatgaaagt    180
gctcagaaac ttattggaga agtaaaagag atgatcaatt caatctcggt taaagatgga    240
gaattaatca ccccctccaa tgatctcctt atgcggctct ctatagtcga tagcattgaa    300
cgtttgggaa tcgataggca tttcaaaagt gaaataaaat cagctctgga ttatgtttac    360
agttattgga acgaaaaagg cattgggtgg ggaagagata gtgttgttgc cgatctcaac    420
tcaactgcct tggggcttcg aactctacga ctacacggat acccggtgtc ttcagatgtg    480
ttacaacact tcaaagaaca aaaagggcag tttgcatgtt cggccattca aacagaggga    540
gagataagaa gtgttctcaa cttatttcgg gcttcccaaa ttgcctttcc gggagagaaa    600
gttatggaag aggcagaagt cttctctaca atatatttaa aagaagccat actaaagctt    660
ccggtctgcg gtctttcacg agagatatcg tacgttctgg aatatggttg gcatataaat    720
ttgccaagat tggaagcaag gaactacatc gacgtatttg gacaggaccc catttatttg    780
acgccaaata tgaagaccca aaaacttcta gaacttgcaa agttggagtt caatatgttt    840
cactctttac aacagcaaga gctaaagctt ctctccagat ggtggaaaga ttcgggtttc    900
tctcaaatga ccttccctcg gcatcgtcac gtggaatatt acactttggc atcttgcatt    960
gatagtgaac ctcaatattc ttcgttcaga cttggatttg ccaaaatctt tcatcttgcc   1020
acggttcttg acgatattta cgacaccttt ggcacgatgg atgagctaga actcttcacg   1080
gcggcagtta agaggtggca tccgtctgcg acggagtggc ttccagaata tatgaaagga   1140
gtatatatgg tgctttacga aaccgttaac gaaatggcag gagaagcaga aaagtctcaa   1200
ggccgagaca cgctcaacta tgcccgaaat gctttggagg cttatattga tgcttctatg   1260
aaagaagcga agtggatttt cagtggtttt ttgccaacat ttgaggagta cctggataac   1320
gggaaagtta gtttcggtta tagcattggc acattgcaac ccattctgac gttgggcatt   1380
ccctttcctc atcacatcct acaagaaata gactttcctt ccaggctcaa tgatgtggca   1440
tgttccattc tccgactaaa aggcgacatt cacacttacc aggctgagag gagccgtgga   1500
gaaaaatctt cgtgtatatc atgttatatg gaagagaatc ccgagtcaac agaggaagat   1560
gcaatcaatc atatcaactc catggtcgac aaattactca aggaactaaa ttgggagtat   1620
ctgagacctg atagcaatgt tccaatcact tccaagaaac atgcatttga cattctgaga   1680
gctttctacc atctctacaa ataccgagat ggcttcagcg ttgcgaacta tgaaataaag   1740
aatttggtca tgacaaccgt cattgagcct gtgcctttat aa                       1782
```

<210> SEQ ID NO 4
<211> LENGTH: 1782
<212> TYPE: DNA
<213> ORGANISM: Pinus ponderosa

<400> SEQUENCE: 4

```
tctagcaagg ttaaggttgt ccgcagaacg atctcaactt ccatccgcat gtgtcggata     60
accactgaat ccggtgaagg cgtacagaga cgcatagcaa atcatcattc caacctctgg    120
gacgataatt tcatacagtc cctctcaacg ccttatgggg caatttcgta ccatgaaagt    180
```

```
gctcagaaac ttattggaga agtaaaagag atgatcaatt caatctcgct taaagatgga    240
gaattaatca ccccctccaa tgatctcctt atgcggctct ctatagttga tagcattgaa    300
cgtttgggaa tcgataggca tttcaaaagt gaaataaaat cagctctgga ttatgtttac    360
agttattgga acgaaaaagg cattgggtgg ggaagagata gtgttgttgc cgatctcaac    420
tcaactgcct tggggcttcg aactctacga ctacacggat acccggtgtc ttcagatgtg    480
ttacaacact tcaaagaaca aaaagggcag tttgcatgtt cggccattca aacagaggga    540
gagataagaa gtgttctcaa cttatttcgg gcttcccaaa ttgcctttcc gggagagaaa    600
gttatggaag aggcagaagt cttctctaca atatatttaa aagaagccat actaaagctt    660
ccggtctgcg gtctttcacg agagatatcg tacgttctgg aatatggttg gcatataaat    720
ttgccaagat tggaagcaag gaactacatc gacgtatttg gacaggaccc atttatattg    780
acgccaaata tgaagaccca aaaacttcta gaacttgcaa agttggagtt caatatgttt    840
cactctttac aacagcaaga gctaaagctt ctctccagat ggtggaaaga ttcgggtttc    900
tctcaaatga ccttccctcg gcatcgtcac gtggaatatt acactttggc atcttgcatt    960
gatagtgaac ctcaacattc ttcgttcaga cttggatttg ccaaaatctt tcatcttgcc   1020
acggttcttg acgatattta cgacaccttt ggcacgatgg atgagctaga actcttcacg   1080
gcggcagtta agaggtggca tccgtctgcg acggagtggc ttccagaata tatgaaagga   1140
gtatatatgg tgctttacga aaccgttaac gaaatggcga gagaagcaga aaagtctcaa   1200
ggccgagaca cgctcaacta tgcccgaaat gctttggagg cttatattga tgcttctatg   1260
aaagaagcga agtggatttt cagtggtttt ttgccaacat ttgaggagta cctggataac   1320
gggaaagtta gtttcggtta tagcattggc acattgcaac ccattctgac gttgggcatt   1380
ccctttcctc atcacatcct acaagaaata gactttcctt ccaggctcaa tgatgtggca   1440
tgttccattc tccgactaaa aggcgacatt cacacttacc aggctgagag gagccgtgga   1500
gaaaaatctt cgtgtatatc atgttatatg gaagagaatc ccgagtcaac agaggaagat   1560
gcaatcaatc atatcaactc catggtcgac aaattactca aggaactaaa ttgggagtat   1620
ctgagacctg atagcaatgt tccaatcact tccaagaaac atgcatttga cattctgaga   1680
actttctacc atctctacaa ataccgagat ggcttcagcg ttgcgaacta tgaaataaag   1740
aatttggtca tgacaaccgt cattgagcct gtgcctttat aa                      1782
```

<210> SEQ ID NO 5
<211> LENGTH: 1782
<212> TYPE: DNA
<213> ORGANISM: Pinus ponderosa

<400> SEQUENCE: 5

```
tctagcaagg ttaaggttgt ccgcagaacg atctcaactt ccatccgcat gtgtcggata     60
accactgaat ccggtgaagg cgtacagaga cgcatagcaa atcatcattc caacctctgg    120
gacgataatt tcatacagtc cctctcaacg ccttatgggg caatttcgta ccatgaaagt    180
gctcagaaac ttattggaga agtaaaagag atgatcaatt caatctcgct taaagatgga    240
gaattaatca ccccctccaa tgatctcctt atgcggctct ctatagttga tagcattgaa    300
cgtttgggaa tcgataggca tttcaaaagt gaaataaaat cagctctgga ttatgtttac    360
agttattgga acgaaaaagg cattgggtgg ggaagagata gtgttgttgc cgatctcaac    420
tcaactgcct tggggcttcg aactctacga ctacacggat acccggtgtc ttcagatgtg    480
ttacaacact tcaaagaaca aaaagggcag tttgcatgtt cggccattca aacagaggga    540
```

```
gagataagaa gtgttctcaa cttatttcgg gcttcccaaa ttgcctttcc gggagagaaa    600

gttatggaag aggcagaagt cttctctaca atatatttaa aagaagccat actaaagctt    660

ccggtctgcg gtctttcacg agagatatcg tacgttctgg aatatggttg gcatataaat    720

ttgccaagat tggaagcaag gaactacatc gacgtatttg gacaggaccc catttatttg    780

acgccaaata tgaagaccca aaaatttcta gaacttgcaa agttggagtt caatatgttt    840

cactctttac aacagcaaga gctaaagctt ctctccagat ggtggaaaga ttcgggtttc    900

tctcaaatga ccttccctcg gcatcgtcac gtggaatatt acactttggc atcttgcatt    960

gatagtgaac ctcaacattc ttcgttcaga cttggatttg ccaaaatctt tcatcttgcc   1020

acggttcttg acgatattta cgacaccttt ggcacgatgg atgagctaga actcttcacg   1080

gcggcagtta agaggtggca tccgtctgcg acggagtggc ttccagaata tatgaaagga   1140

gtatatatgg tgctttacga aaccgttaac gaaatggcga gagaagcaga aaagtctcaa   1200

ggccgagaca cgctcaacta tgcccgaaat gctttggagg cttatattga tgcttctatg   1260

aaagaagcga agtggatttt cagtggtttt ttgccaacat ttgaggagta cctgtataac   1320

gggaaagtta gtttcggtta tagcattggc acattgcaac ccattctgac gttgggcatt   1380

ccctttcctc atcacatcct acaagaaata gactttcctt ccaggctcaa tgatgtggca   1440

tgttccattc tccgactaaa aggcgacatt cacacttacc aggctgagag gagccgtgga   1500

gaaaaatctt cgtgtatatc atgttatatg gaagagaatc ccgagtcaac agaggaagat   1560

gcaatcaatc atatcaactc catggtcgac aaattactca aggaactaaa ttgggagtat   1620

ctgagacctg atagcaatgt tccaatcact tccaagaaac atgcatttga cattctgaga   1680

actttctacc atctctacaa ataccgagat ggcttcagcg ttgcgaacta tgaaataaag   1740

aatttggtca tgacaaccgt cattgagcct gtgcctttat aa                       1782
```

<210> SEQ ID NO 6
<211> LENGTH: 1782
<212> TYPE: DNA
<213> ORGANISM: Pinus jeffreyi

<400> SEQUENCE: 6

```
tctagcaagg ttaaggttgt ccgcagaacg atctcaactt ccatccgcat gtgtcggata     60

accactgaat ccggtgaagg cgtacagaga cgcatagcaa atcatcattc caacctctgg    120

gacgataatt tcatacagtc cctctcaacg ccttatgggg caatttcgta ccatgaaagt    180

gctcagaaac ttattggaga agtaaaagag atgatcaatt caatctcgct taaagatgga    240

gaattaatca ccccctccaa tgatctcctt atgcggctct ctatagttga tagcattgaa    300

cgtttgggaa tcgataggca tttcaaaagt gaaataaaat cagctctgga ttatgtttac    360

agttattgga acgaaaaagg cattgggtgg ggaagagata gtgttgttgc cgatctcaac    420

tcaactgcct tggggcttcg aactctacga ctacacggat acccggtgtc ttcagatgtg    480

ttacaacact tcaaagaaca aaaagggcag tttgcatgtt cggccattca aacagaggga    540

gagataagaa gtgttctcaa cttatttcgg gcttcccaaa ttgcctttcc gggagagaaa    600

gttatggaag aggcagaagt cttctctaca atatatttaa aagaagccat actaaagctt    660

ccggtctgcg gtctttcacg agagatatcg tacgttctgg aatatggttg gcatataaat    720

ttgccaagat tggaagcaag gaactacatc gacgtatttg gacaggaccc catttatttg    780

acgccaaata tgaagaccca aaaacttcta gaacttgcaa agttggagtt caatatgttt    840
```

```
cactctttac aacagcaaga gctaaagctt ctctccagat ggtggaaaga ttcgggtttc     900

tctcaaatga ccttccctcg gcatcgtcac gtggaatatt acactttggc atcttgcatt     960

gatagtgaac ctcaacattc ttcgttcaga cttggatttg ccaaaatctt tcatcttgcc    1020

acggttcttg acgatattta cgacaccttt ggcacgatgg atgagctaga actcttcacg    1080

gcggcagtta agaggtggca tccgtctgcg acggagtggc ttccagaata tatgaaagga    1140

gtatatatgg tgctttacga aaccgttaac gaaatggcag gagaagcaga aaagtctcaa    1200

ggccgagaca cgctcaacta tgcccgaaat gcttcggagg cttatattga tgcttctatg    1260

aaagaagcga agtggatttt cagtggtttt ttgccaacat ttgaggagta cctggataac    1320

gggaaagtta gtttcggtta tagcattggc acattgcaac ccattctgac gttgggcatt    1380

ccctttcctc atcacatcct acaagaaata gactttcctt ccaggctcaa tgatgtggca    1440

tgttccattc tccgactaaa aggcgacatt cacacttacc aggctgagag gagccgtgga    1500

gaaaaatctt cgtgtatatc atgttatatg gaagagaatc ccgagtcaac agaggaagat    1560

gcaatcaatc atatcaactc catggtcgac aaattactca aggaactaaa ttgggagtat    1620

ctgagacctg atagcaatgt tccaatcact tccaagaaac atgcatttga cattctgaga    1680

gctttctacc atctctacaa ataccgagat ggcttcagcg ttgcgaacta tgaaataaag    1740

aatttggtca tgacaaccgt cattgagcct gtgcctttat aa                       1782
```

<210> SEQ ID NO 7
<211> LENGTH: 1771
<212> TYPE: DNA
<213> ORGANISM: Pinus sabiniana

<400> SEQUENCE: 7

```
tctagcaagg ttaaggttgt ccgcagaacg atctcaactt ccatccgcat gtgtcggata      60

accactgaat ccggtgaagg cgtacagaga cgcatagcaa atcatcattc caacctctgg     120

gacgataatt tcatacagtc cctctcaacg ccttatgggg caatttcgta ccatgaaagt     180

gctcagaaac ttattggaga agtaaaagag atgatcaatt caatctcggt taaagatgga     240

gaattaatca ccccctccaa tgatctcctt atgcggctct ctatagttga tagcattgaa     300

cgtttaggaa tcgataggca tttcaaaagt gaaataaaat cagctctgga ttatgtttac     360

agttattgga acgaaaaagg cattgggtgg ggaagagata gtgttgttgc cgatctcaac     420

tcaactgcct tggggcttcg aactctacga ctacacggat acccggtgtc ttcagatgtg     480

ttacaacact tcaaagaaca aaaagggcag tttgcatgtt cggccattca aacagaggga     540

gagataagaa gtgttctcaa cttatttcgg gcttcccaaa ttgcctttcc gggagagaaa     600

gttatggaag aggcagaagt cttctctaca atatatttaa aagaagccat actaaagctt     660

ccggtctgcg gtctttcacg agagatatcg tacgttctgg aatatggttg gcatataaat     720

ttgccaagat tggaagcaag gaactacatc gacgtatttg gagaggaccc catttatttg     780

acgccaaata tgaagaccca aaaacttcta gaacttgcaa agttggagtt caatatgttt     840

cactctttac aacagcaaga gctaaagctt ctctccagat ggtggaaaga ttcgggtttc     900

tctcaaatga ccttccctcg gcatcgtcac gtggaatatt acactttggc atcttgcatt     960

gatagtgaac ctcaacattc ttcgttcaga cttggatttg ccaaaatctt tcatcttgcc    1020

acggttcttg acgatattta cgacaccttt ggcacgatgg atgagctaga actcttcacg    1080

gcggcagtta agaggtggca tccgtctgcg acggagtggc ttccagaata tatgaaagga    1140

gtatatatgg tgctttacga aaccgttaac gaaatggcag gagaagcaga aaagtctcaa    1200
```

```
ggccgagaca cgctcaacta tggccgaaat gctttggagg cttatattga tgcttctatg   1260

gaagaagcga agtggatttt cagtggtttt ttgccaacat ttgaggagta cctggataac   1320

gggaaagtta gtttcggtta tggcattggc acattgcaac ccattctgac gttgggcatt   1380

ccctttcctc atcacatcct acaagaaata gactttcctt ccaggctcaa tgatgtggca   1440

tcttccattc tccgactaaa aggcgacatt cacacttacc aggctgagag gagccgtgga   1500

gaaaaatctt cgtgtatatc atgttatatg gaagagaatc ccgagtcaac agaggaagat   1560

gcaatcaatc atatcaactc catggtcgac aaattactca aggaactaaa ttgggagtat   1620

ctgagacctg atagcaatgt tccaatcact tccaagaaac atgcatttga cattctgaga   1680

gctttctacc atctctacaa ataccgagat ggcttcagcg ttgcgaacta tgaaataaag   1740

aatttggtca tgacaaccgt cattgagcct g                                  1771
```

<210> SEQ ID NO 8
<211> LENGTH: 1783
<212> TYPE: DNA
<213> ORGANISM: Pinus sabiniana

<400> SEQUENCE: 8

```
tctagcaagg ttaaggttgt ccgcagaacg atctcaactt ccatccgcat gtgtcggata     60

accactgaat ccggtgaagg cgtacagaga cgcatagcaa atcatcattc caacctctgg    120

gacgataatt tcatacagtc cctctcaacg ccttatgggg caatttcgta ccatgaaagt    180

gctcagaaac ttattggaga agtaaaagag atgatcaatt caatctcgct taaagatgga    240

gaattaatca ccccctccaa tgatctcctt atgcggctct ctatagtcga tagcattgaa    300

cgtttgggaa tcgataggca tttcaaaagt gaaataaaat cagctctgga ttatgtttac    360

agttattgga acgaaaaagg cattgggtgg ggaagagata gtgttgttgc cgatctcaac    420

tcaactgcct tggggcttcg aactctacga ctacacggat acccggtgtc ttcagatgtg    480

ttacaacact tcaaagaaca aaaagggcag tttgcatgtt cggccattca aacagaggga    540

gagataagaa gtgttctcaa cttatttcgg gcttcccaaa ttgcctttcc gggagagaaa    600

gttatggaag aggcagaagt cttctctaca atatatttaa aagaagccat actaaagctt    660

ccggtctgcg gtctttcacg agagatatcg tacgttctgg aatatggttg gcatataaat    720

ttgccaagat tggaagcaag gaactacatc gacgtatttg gagaggaccc catttatttg    780

acgccaaata tgaagaccca aaaacttcta gaacttgcaa agttggagtt caatatgttt    840

cactctttac aacagcaaga gctaaagctt ctctccagat ggtggaaaga ttcgggtttc    900

tctcaaatga ccttccctcg gcatcgtcac gtggaatatt acactttggc atcttgcatt    960

gatagtgaac ctcaacattc ttcgttcaga cttggatttg ccaaaatctt tcatcttgcc   1020

acggttcttg acgatattta cgacaccttt ggcacgatgg atgagctaga actcttcacg   1080

gcggcagtta agaggtggca tccgtctgcg acggagtggc ttccagaata tatgaaagga   1140

gtatatatgg tgctttacga aaccgttaac gaaatggcag gagaagcaga aaagtctcaa   1200

ggccgagaca cgctcaacta tggccgaaat gctttggagg cttatattga tgcttctatg   1260

gaagaagcga agtggatttt cagtggtttt ttgccaacat ttgaggagta cctggataac   1320

gggaaagtta gtttcggtta tggcattggc acattgcaac ccattctgac gttgggcatt   1380

ccctttcctc atcacatcct acaagaaata gactttcctt ccaggctcaa tgatgtggca   1440

tcttccattc tccgactaaa aggcgacatt cacacttacc aggctgagag gagccgtgga   1500
```

```
gaaaaatctt cgtgtatatc atgttatatg gaagagaatc ccgagtcaac agaggaagat   1560

gcaatcaatc atatcaactc catggtcgac aaattactca aggaactaaa ttgggagtat   1620

ctgagacctg atagcaatgt tccaatcact tccaagaaac atgcatttga cattctgaga   1680

gctttctacc atctctacaa ataccgagat ggcttcagcg ttgcgaacta tgaaataaag   1740

aatttggtca tgacaaccgt cattgagcct gtgcctttat aaa                      1783
```

<210> SEQ ID NO 9
<211> LENGTH: 1782
<212> TYPE: DNA
<213> ORGANISM: Pinus patula

<400> SEQUENCE: 9

```
tctagcaagg ttaaggttgt ccgcagaacg atctcaactt ccatccgcat gtgtcggata     60

actactgtat ccggtgaagg cgtacagaga cgcatagcaa atcatcattc caacctctgg    120

gacgataatt tcatacagtc cctctcaacg ccttatgggg caatttcgta ccatgaaagt    180

gctcagaaac ttattggaga agtaaaagag atgatcaatt caatctcggt taaagatgga    240

gaattaatca ccccctccaa tgatctcctt atgcggctct ctatagtcga tagcattgaa    300

cgtttgggaa tcgataggca tttcaaaagt gaaataaaat cagctctgga ttatgtttac    360

agttattgga acgaaaaagg cattgggtgg ggaagagata gtgttgttgc cgatctcaac    420

tcaactgcct tggggcttcg aactctacga ctacacggat acccggtgtc ttcagatgtg    480

ttacaacact tcaaagaaca aaaagggcag tttgcatgtt cggccattca aacagaggga    540

gagataagaa gtgttctcaa cttatttcgg gcttcccaaa ttgcctttcc gggagagaaa    600

gttatggaag aggcagaagt cttctctaca atatatttaa aagaagccat actaaagctt    660

ccggtctgcg gtctttcacg agagatatcg tacgttctgg aatatggttg gcatataaat    720

ttgccaagat tggaagcaag gaactacatc gacgtatttg gacaggaccc catttatttg    780

acgccaaata tgaagaccca aaaacttcta gaacttgcaa agttggagtt caatatgttt    840

cactctttac aacagcaaga gctaaagctt ctctccagat ggtggaaaga ttcgggtttc    900

tctcaaatga ccttccctcg gcatcgtcac gtggaatatt acactttggc atcttgcatt    960

gatagtgaac ctcaacattc ttcgttcaga cttggatttg ccaaaatatt tcatcttgcc   1020

acggttcttg acgatattta cgacaccttt ggcacgatgg atgagctaga actcttcaca   1080

gcggcagttg agaggtggca tccgtctgcg acggagtggc ttccagaata tatgaaagga   1140

gtatatatgg tgctttacga aaccgttaac gaaatggcag gagaagcaga aaagtctcaa   1200

ggccgagaca cgctcaacta tgcccgaaat gctttggagg cttatattga tgcttctatg   1260

aaagaagcga agtggatttt cagtggtttt ttgccaacat ttgaggagta cctggataac   1320

gggaaagtta gtttcggtta tagcattggc acattgcaac ccattctgac gttgggcatt   1380

ccctttcctc atcacatcct acaagaaata gactttcctt ccaggctcaa tgatgtggca   1440

tgttccattc tccgactaaa aggcgacatt cacacttacc aggctgagag gagccgtgga   1500

gaaaaatctt cgtgtatatc atgttatatg gaagagaatc ccgagtcaac agaggaagat   1560

gcaatcgatc atatcaactc catggtcgac aaattactca aggaactaaa tcgggagtat   1620

ctgagacctg atagcaatgt tccaatcact tccaagaaac atgcatttga cattctgaga   1680

gctttctacc atctctacaa ataccgagat ggcttcagcg ttgcgaacta tgaaataaag   1740

aatttggtca tgacaaccgt cattgagcct gtgcctttat aa                       1782
```

<210> SEQ ID NO 10
<211> LENGTH: 1782
<212> TYPE: DNA
<213> ORGANISM: Pinus montezumae

<400> SEQUENCE: 10

```
tctagcaagg ttaaggttgt ccgcagaacg atctcaactt ccatccgcat gtgtcggata      60

accactgtat ccggtgaagg cgtacagaga cgcatagcaa atcatcattc caacctctgg     120

gacgataatt tcatacagtc cctctcaacg ccttatgggg caatttcgta ccatgaaagt     180

gctcagaaac ttattggaga agtaaaagag atgatcaatt caatctcggt taaagatgga     240

gaattaatca cccccctcaa tgatctcctt atgcggctct ctatagtcga tagcattgaa     300

cgtttgggaa tcgataggca tttcaaaagt gaaataaaat cagctctgga ttatgtttac     360

agttattgga acgaaaaagg cattgggtgg ggaagagata gtgttgttgc cgatctcaac     420

tcaactgcct tggggcttcg aactctacga ctacacggat acccggtgtc ttcagatgtg     480

ttacagcact tcaaagaaca aaaagggcag tttgcatgtt cggccattca aacagaggga     540

gagataagaa gtgttctcaa cttatttcgg gcttcccaaa ttgcctttcc gggagagaaa     600

gttatggaag aggcagaagt cttctctaca atatatttaa aagaagccat actaaagctt     660

ccggtctgcg gtctttcacg agagatatcg tacgttctgg aatatggttg gcatataaat     720

ttgccaagat tggaagcaag gaactacatc gacgtatttg gacaggaccc catttatttg     780

acgccaaata tgaagaccca aaaacttcta gaacttgcaa agttggagtt caatatgttt     840

cactctttac aacagcaaga gctaaagctt ctctccagat ggtggaaaga ttcgggtttc     900

tctcaaatga ccttccctcg gcatcgtcac gtggaatatt acactttggc atcttgcatt     960

gatagtgaac ctcaacattc ttcgttcaga cttggatttg ccaaaatgtt tcatcttgcc    1020

acggttcttg acgatattta cgacaccttt ggcacgatgg atgagctaga actcttcacg    1080

gcggcagtta agaggtggca tccgtctgcg acggagtggc ttccagaata tatgaaagga    1140

gtatatatgg tgctttacga aaccgttaac gaaatggcag gagaagcaga aaagtctcaa    1200

ggccgagaca cgctcaacta tgcccgaaat gctttggagg cttatattga tgcttctatg    1260

aaagaagcga agtggatttt cagtggtttt ttgccaacat ttgaggagta cctggataac    1320

gggaaagtta gtttcggtta tagcattggc acattgcaac ccattctgac gttgggcatt    1380

ccctttcctc atcacatcct acaagaaata gactttcctt ccaggctcaa tgatgtggca    1440

tgttccattc tccgactaaa aggcgacatt cacacttacg aggctgagag gagccgtgga    1500

gaaaaatctt cgtgtatatc atgttatatg gaagagaatc ccgagtcaac agaggaagat    1560

gcaatcaatc atatcaactc catggtcgac aaattactca aggaactaaa ttgggagtat    1620

ctgagacctg atagcaatgt tccaatcact tccaagaaac atgcatttga cattctgaga    1680

gctttctacc atctctacaa ataccgagat ggcttcagcg ttgcgaacta tgaaataaag    1740

aatttggtca tgacaaccgt cattgagcct gtgcctttat aa                       1782
```

<210> SEQ ID NO 11
<211> LENGTH: 1695
<212> TYPE: DNA
<213> ORGANISM: Pinus pseudostrobus

<400> SEQUENCE: 11

```
agacgcakag stgrtywyca ttccaaccty tgggacgata atttcataca gtccctctca      60

acgccttatg gggcaatttc gtaccatgaa agtgctcaga aacttattgg agaagtaaaa     120
```

```
gagatgatca attcaatctc ggttaaagat ggagaattaa tcaccccctc caatgatctc    180
cttatgcggc tctctatagt cgatagcatt gaacgtttgg gaatcgatag gcatttcaaa    240
agtgaaataa aatcagctct ggattatgtt tacagttatt ggaacgaaaa aggcattggg    300
tggggaagag atagtgttgt tgccgatctc aactcaactg ccttggggct tcgaactcta    360
cgactacacg gatacccggt gtcttcagat gtgttacagc acttcaaaga acaaaaaggg    420
cagtttgcat gttcggccat tcaaacagag ggagagataa gaagtgttct caacttattt    480
cgggcttccc aaattgcctt tccgggagag aaagttatgg aagaggcaga agtcttctct    540
acaatatatt taaaagaagc catactaaag cttccggtct gcggtctttc acgagagata    600
tcgtacgttc tggaatatgg ttggcatata aatttgccaa gattggaagc aaggaactac    660
atcgacgtat ttggacagga ccccatttat ttgacgccaa atatgaagac ccaaaaactt    720
ctagaacttg caaagttgga gttcaatatg tttcactctt tacaacagca agagctaaag    780
cttctctcca gatggtggaa agattcgggt ttctctcaaa tgaccttccc tcggcatcgt    840
cacgtggaat attacacttt ggcatcttgc attgatagtg aacctcaaca ttcttcgttc    900
agacttggat ttgccaaaat gtttcatctt gccacggttc ttgacgatat ttacgacacc    960
tttggcacga tggatgagct agaactcttc acggcggcag ttaagaggtg gcatccgtct   1020
gcgacggagt ggcttccaga atatatgaaa ggagtatata tggtgcttta cgaaaccgtt   1080
aacgaaatgg caggagaagc agaaaagtct caaggccgag acacgctcaa ctatgcccga   1140
aatgctttgg aggcttatat tgatgcttct atgaaagaag cgaagtggat tttcagtggt   1200
tttttgccaa catttgagga gtacctggat aacgggaaag ttagtttcgg ttatagcatt   1260
ggcacattgc aacccattct gacgttgggc attccctttc ctcatcacat cctacaagaa   1320
atagactttc cttccaggct caatgatgtg gcatgttcca ttctccgact aaaaggcgac   1380
attcacactt acgaggctga gaggagccgt ggagaaaaat cttcgtgtat atcatgttat   1440
atggaagaga atcccgagtc aacagaggaa gatgcaatca atcatatcaa ctccatggtc   1500
gacaaattac tcaaggaact aaattgggag tatctgagac ctgatagcaa tgttccaatc   1560
acttccaaga aacatgcatt tgacattctg agagctttct accatctcta caaataccga   1620
gatggcttca gcgttgcgaa ctatgaaata aagaatttgg tcatgacaac cgtcattgag   1680
cctgtgcctt tataa                                                    1695
```

```
<210> SEQ ID NO 12
<211> LENGTH: 1695
<212> TYPE: DNA
<213> ORGANISM: Pinus coulteri

<400> SEQUENCE: 12

agacgcatag ctggtcatca ttccaaccty tgggacgatr atttsataca gtccctytca     60
acgccttatg gggcaatttc gtaccatgaa agtgctcaga aacttattgg agaagtaaaa    120
gagatgatca attcaatctc ggttaaagat ggagaattaa tcaccccctc caatgatctc    180
cttatgcggc tctctatagt tgatagcatt gaacgtttgg gaatcgatag gcatttcaaa    240
agtgaaataa aatcagctct ggattatgtt tacagttatt ggaacgaaaa aggcattggg    300
tggggaagag atagtgttgt tgccgatctc aactcaactg ccttggggct tcgaactcta    360
cgactacacg gatacccggt gtcttcagat gtgttacaac acttcaaaga acaaaaaggg    420
cagtttgcat gttcggccat tcaaacagag ggagagataa gaagtgttct caacttattt    480
cgggcttccc aaattgcctt tccgggagag aaagttatgg aagaggcaga agtcttctct    540
```

```
acaatatatt taaaagaagc catactaaag cttccggtct gcggtctttc acgagagata    600
tcgtacgttc tggaatatgg ttggcatata aatttgccaa gattggaagc aaggaactac    660
atcgacgtat ttggagagga ccccatttat ttgacgccaa atatgaagac ccaaaaactt    720
ctagaacttg caaagttgga gttcaatatg tttcactctt tacaacagca agagctaaag    780
cttctctcca gatggtggaa agattcgggt ttctctcaaa tgaccttccc tcggcatcgt    840
cacgtggaat attacacttt ggcatcttgc attgatagtg aacctcaaca ttcttcgttc    900
agacttggat ttgccaaaat ctttcatctt gccacggttc ttgacgatat ttacgacacc    960
tttggcacga tggatgagct agaactcttc acggcggcag ttaagaggtg gcatccgtct   1020
gcgacggagt ggcttccaga atatatgaaa ggagtatata tggtgcttta cgaaaccgtt   1080
aacgaaatgg caggagaagc agaaaagtct caaggccgag acacgctcaa ctatggccga   1140
aatgctttgg aggcttatat tgatgcttct atggaagaag cgaagtggat tttcagtggt   1200
tttttgccaa catttgagga gtacctggat aacgggaaag ttagtttcgg ttatggcatt   1260
ggcacattgc aacccattct gacgttgggc attccctttc ctcatcacat cctacaagaa   1320
atagactttc cttccaggct caatgatgtg gcatcttcca ttctccgact aaaaggcgac   1380
attcacactt accaggctga gaggagccgt ggagaaaaat cttcgtgtat atcatgttat   1440
atggaagaga atcccgagtc aacagaggaa gatgcaatca atcatatcaa ctccatggtc   1500
gacaaattac tcaaggaact aaattgggag tatctgagac ctgatagcaa tgttccaatc   1560
acttccaaga aacatgcatt tgacattctg agagctttct accatctcta caaataccga   1620
gatggcttca gcgttgcgaa ctatgaaata aagaatttgg tcatgacaac cgtcattgag   1680
cctgtgcctt tataa                                                    1695
```

<210> SEQ ID NO 13
<211> LENGTH: 1671
<212> TYPE: DNA
<213> ORGANISM: Pinus torreyana

<400> SEQUENCE: 13

```
aacctctggg acgatgattt gatacagtcc ctttcaacgc cttatggggc aatttcgtac     60
catgaaagtg ctcagaaact tattggagaa gtaaaagaga tgatcaattc aatctcggtt    120
aaagatggag aattaatcac cccctccaat gatctcctta tgcggctctc tatagttgat    180
agcattgaac gtttgggaat cgataggcat ttcaaaagtg aaataaaatc agctctggat    240
tatgtttaca gttattggaa cgaaaaaggc attgggtggg gaagagatag tgttgttgcc    300
gatctcaact caactgcctt ggggcttcga actctacgac tacacggata cccggtgtct    360
tcagatgtgt tacaacactt caaagaacaa aaagggcagt ttgcatgttc ggccattcaa    420
acagagggag agataagaag tgttctcaac ttatttcggg cttcccaaat tgcctttccg    480
ggagagaaag ttatggaaga ggcagaagtc ttctctacaa tgtatttaaa agaagccata    540
ctaaagcttc cggtctgcgg tctttcacga gagatatcgt acgttctgga atatggttgg    600
catataaatt tgccaagatt ggaagcaagg aactacatcg acgtatttgg acaggacccc    660
atttatttga cgccaaatat gaagacccaa aaacttctag aacttgcaaa gttggagttc    720
aatatgtttc actctttaca acagcaagag ctaaagcttc tctccagatg gtggaaagat    780
tcgggtttct ctcaaatgac cttccctcgg catcgtcacg tggaatatta cactttggca    840
tcttgcattg atagtgaacc tcaacattct tcgttcagac ttggatttgc caaaatcttt    900
```

```
catcttgcca cggttcttga cgatatttac gacacctttg gcacgatgga tgagctagaa     960

ctcttcacgg cggcagttaa gaggtggcat ccgtctgcga cggagtggct tccagaatat    1020

atgaaaggag tatatatggt gctttacgaa accgttaacg aaatggcagg agaagcagaa    1080

aagtctcaag gccgagacac gctcaactat gcccgaaatg ctttggaggc ttatattgat    1140

gcttctatgg aagaagcgaa gtggattttc agtggttttt tgccaacatt tgaggagtac    1200

ctggataacg ggaaagttag tttcggttat ggcattggca cattgcaacc cattctgacg    1260

ttgggcattc cctttcctca tcacatccta caagaaatag actttccttc caggctcaat    1320

gatgtggcat cttccattct ccgactaaaa ggcgacattc acacttacca ggctgagagg    1380

agccgtggag aaaaatcttc gtgtatatca tgttatatgg aagagaatcc cgagtcaaca    1440

gaggaagatg caatcaatca tatcaactcc atggtcgaca aattactcaa ggaactaaat    1500

tgggagtatc tgagacctga tagcaatgtt ccaatcactt ccaagaaaca tgcatttgac    1560

attctgagag ctttctacca tctctacaaa taccgagatg gcttcagcgt tgcgaactat    1620

gaaataaaga atttggtcat gacaaccgtc attgagcctg tgcctttata a             1671
```

```
<210> SEQ ID NO 14
<211> LENGTH: 1695
<212> TYPE: DNA
<213> ORGANISM: Pinus attenuata

<400> SEQUENCE: 14

agacgcagag gtgatttcca ttccaacctc tgggacgata atttcataca gtccctctca      60

acgccttatg gggcaatttc gtaccatgaa agtgctcaga aacttattgg agaagtaaaa     120

gagatgatca attcaatctc ggataaagat ggagaattaa tcacccccctc caatgatctc    180

cttatgctgc tctctatagt cgatagcatt gaacgtttgg gaatcgatag gcatttcaaa     240

agtgaaataa aatcagctct ggattatgtt tacagttatt ggaacgaaaa aggcattggg     300

tggggaagag atagtgttgt tgccgatctc aactcaactg ccttggggct tcgaactcta     360

cgactacacg gatacccggt gtcttcagac gtgttacaac acttcaaaga acaaaatggg     420

cagtttgcat gttcggccat tcaaacagag ggagagataa gaagtgttct caacttattt     480

cgggcttccc aaattgcctt tccgggagag aaagttatgg aagaggcaga agtcttctct     540

acaaaatatt taaaagaagc catactaaag cttccggtct gcggtctttc acgagagata     600

tcgtacgttc tggaatatgg ttggcatatg aatttgccaa gattggaagc aaggaactac     660

atcgacgtat ttggacagga ccccatttat ttgacgccaa atatgaagac ccaaaaactt     720

ctagaacttg caaagttgga gttcaatatg tttcactctt tacaacagca agagctaaag     780

cttctctcca gatggtggaa agattcgggt ttctctcaaa tgaccttccc tcggcatcgt     840

cacgtggaat attacacttt ggcatcttgc attgatagtg aacctcaaca ttcttcgttc     900

agacttggat ttgccaaaat atttcatctt gccacggttc ttgacgatat ttacgacacc     960

tttggcacga tggatgagct agaactcttc acagcggcag ttaagaggtg gcatccgtct    1020

gcgacggagt ggcttccaga atatatgaaa ggagtatata tggtgcttta cgaaaccgtt    1080

aacgaaatgg caggagaagc agaaaagtct caaggccgag acacgctcaa ctatgcccga    1140

aatgctttgg aggcttatat tgatgcttct atggaagaag cgaagtggat tttcagtggt    1200

tttttgccaa catttgagga gtacctggat aacgggaaag ttagtttcgg ttataccatt    1260

ggcacattgc aacccattct gacgttgggc attccctttc ctcatcacat cctacaagaa    1320

atagactttc cttccaggct caatgatgtg gcatgttcca ttctccgact aaaaggcgac    1380
```

```
gttcacactt accagcctga gaggagccgt ggagaagaat cttcgtgtat atcatgttat   1440

attgaagaga atcccgagtc aacagaggaa gatgcaatca atcatatcaa ctccatggtc   1500

gacaaattac tcaaggaact aaattgggag tatctgagac ctgatagcaa tgttccaatc   1560

acttccaaga aacatgcatt tgacattctg agagctttgt accatctcta caaataccga   1620

gatggctaca gcgttgcgaa ctatgaaata aagaatttgg tcatgacaac cgtcattgag   1680

cctgtgcctt tataa                                                    1695
```

<210> SEQ ID NO 15
<211> LENGTH: 1671
<212> TYPE: DNA
<213> ORGANISM: Pinus radiata

<400> SEQUENCE: 15

```
aacctctggg acgatgattt gatacagtcc ctttcaacgc cttatggggc aatttcgtac     60

catgaaagtg ctcagaaact tattggagaa gtaaaagaga tgatcaattc aatctcggat    120

aaaaatggag aattaatcac cccctccaat gatctcctta tgcggctctc tatagtcgat    180

agcattgaac gtttgggaat cgataggcat ttcaaaagtg aaataaaatc agctctggat    240

tatgtttaca gttattggaa cgaaaaaggc attgggtggg gaagagatag tgttgttgcc    300

gatctcaact caactgcctt ggggcttcga actctacgac tacacggata cccggtgtct    360

tcagacgtgt tacaacactt caaagaacaa aatgggcagt ttgcatgttc ggccattcaa    420

acagagggag agataagaag tgttctcaac ttatttcggg cttcccaaat tgcctttccg    480

ggagagaaag ttatggaaga ggcagaagtc ttctctacaa aatatttaaa agaagccata    540

ctaaagcttc cggtctgcgg tctttcacga gagatatcgt acgttctgga atatggttgg    600

catatgaatt tgccaagatt ggaagcaagg aactacatcg acgtatttgg acaggacccc    660

atttatttga cgccaaatat gaagacccaa aaacttctag aacttgcaaa gttggagttc    720

aatatgtttc actctttaca acagcaagag ctaaagcttc tctccagatg gtggaaagat    780

tcgggtttct ctcaaatgac cttccctcgg catcgtcacg tggaatatta cactttggca    840

tcttgcattg atagtgaacc tcaacattct tcgttcagac ttggatttgc caaaatattt    900

catcttgcca cggttcttga cgatatttac gacacctttg gcacgatgga tgagctagaa    960

ctcttcacag cggcagttaa gaggtggcat ccgtctgcga cggagtggct tccagaatat   1020

atgaaaggag tatatatggt gctttacgaa accgttaacg aaatggcagg agaagcagaa   1080

aagtctcaag gccgagacac gctcaactat gcccgaaatg ctttggaggc ttatattgat   1140

gcttctatgg aagaagcgaa gtggattttc agtggttttt tgccaacatt tgaggagtac   1200

ctggataacg ggaaagttag tttcggttat accattggca cattgcaacc cattctgacg   1260

ttgggcattc cctttcctca tcacatccta caagaaatag actttccttc caggctcaat   1320

gatgtggcat gttccattct ccgactaaaa ggcgacgttc acacttacca gcctgagagg   1380

agccgtggag aagaatcttc gtgtatatca tgttatatgg aagagaatcc cgagtcaaca   1440

gaggaagatg caatcaatca tatcaactcc atggtcgaca aattactcaa ggaactaaat   1500

tgggagtatc tgagacctga tagcaatgtt ccaatcactt ccaagaaaca tgcatttgac   1560

attctgagag ctttgtacca tctctacaaa taccgagatg gctacagcgt tgcgaactat   1620

gaaataaaga atttggtcat gacaactgtc attgagcctg tgcctttata a            1671
```

<210> SEQ ID NO 16

```
<211> LENGTH: 1782
<212> TYPE: DNA
<213> ORGANISM: Pinus contorta

<400> SEQUENCE: 16

tctagcaagg ttaaggttgt ccgcagaacg atgtcaactt ccatccgcat gtgtcagata     60

accactgtat ccggtgaagg cgtacagaga cgcatagcaa atcatcattc caacctctgg    120

gacgataatt tcatacagtc cctctcaacg ccttatgggg caatttcgta ccatgaaagt    180

gctcagaaac ttattggaga agtaaaagag atgatcaatt caatctcggt taaagatgga    240

gaattaatca ccccctccaa tgatctcctt atgcggctct ctatagtcga tagcattgaa    300

cgtttgggaa tcgataggca tttcaaaagt gaaataaaat cagctctgga ttatgtttac    360

agttattgga acgaaaaagg cattgggtgg ggaagagata gtgttgttgc cgatctcaac    420

tcaactgcct tggggcttcg aactctacga ctacacggat acccggtgtc ttcagacgtg    480

ttacaacact tcaaagaaca aaaagggcag tttgcatgtt cggccattca aacagaggga    540

gagataagaa gtgttctcaa cttatttcgg gcttcccaaa ttgcctttcc gggagagaaa    600

gttatggaag aggcagaagt cttctctaca aaatatttaa aagaagccat actaaagctt    660

ccggtctgcg gtctttcacg agagatatcg tacgttctgg aatatggttg gcatatgaat    720

ttgccaagat tggaagcaag gaactacatc gacgtatttg gacaggaccc catttatttg    780

acgccaaata tgaagaccca aaaacttcta gaacttgcta agttggagtt caatatgttt    840

cactctttac aacagcaaga gctaaagctt ctctccagat ggtggaaaga ttcgggtttc    900

tctcaaatga ccttccctcg gcatcgtcac gtggaatatt acactttggc atcttgcatt    960

gatagtgaac ctcaacattc ttcgttcaga cttggatttg ccaaaatatt tcatcttgcc   1020

acggttcttg acgatattta cgacaccttt ggcacgatgg atgagctaga actcttcaca   1080

gcggcagtta agaggtggca tccgtctgcg acggagtggc ttccagaata tatgaaagga   1140

gtatatatgg tgctttacga aaccgttaac gaaatggcag gagaagcaga aaagtctcaa   1200

ggccgagaca cgctcaacta tgcccgaaat gctttggagg cttatattga tgcttctatg   1260

gaagaagcga agtggatttt cagtggtttt ttgccaacat ttgaggagta cctggataac   1320

gggaaagtta gtttcggtta taccattggc acattgcaac ccattctgac gttgggcatt   1380

ccctttcctc atcacatcct acaagaaata gactttcctt ccaggctcaa tgatgtggca   1440

tgttccattc tccgactaaa aggcgacatt cacacttacc agcctgagag gagccgtgga   1500

gaagaatctt cgtgtatatc atgttatatg gaagataatc ccgagtcaac agaggaagat   1560

gcaatcaatc atatcaactc catggtcgac aaattactca aggaactaaa ttgggagtat   1620

ctgagacctg atagcaatgt tccaatcact tccaagaaac atgcatttga cattctgaga   1680

gctttctacc atctctacaa ataccgagat ggctacagcg ttgcgaacta tgaaataaag   1740

aatttggtca tgacaactgt cattgagcct gtgcctttat aa                      1782


<210> SEQ ID NO 17
<211> LENGTH: 1782
<212> TYPE: DNA
<213> ORGANISM: Pinus contorta

<400> SEQUENCE: 17

tctagcaagg ttaaggttgt ccgcagaacg atgtcaactt ccatccgcat gtgtcagata     60

accactgtat ccggtgaagg cgtacagaga cgcatagcaa atcatcattc caacctctgg    120

gacgataatt tcatacagtc cctctcaacg ccttatgggg caatttcgta ccatgaaagt    180
```

```
gctcagaaac ttattggaga agtaaaagag atgatcaatt caatctcggt taaagatgga    240
gaattaatca ccccgtccaa tgatctcctt atgcggctct ctatagtcga tagcattgaa    300
cgtttgggaa tcgataggca tttcaaaagt gaaataaaat cagctctgga ttatgtttac    360
agttattgga acgaaaaagg cattgggtgg ggaagagata gtgttgttgc cgatctcaac    420
tcaactgcct tggggcttcg aactctacga ctacacggat acccggtgtc ttcagacgtg    480
ttacaacact tcaaagaaca aaaagggcag tttgcatgtt cggccattca aacagaggga    540
gagataagaa gtgttctcaa cttatttcgg gcttcccaaa ttgcctttcc gggagagaaa    600
gttatggaag aggcagaagt cttctctaca aaatatttaa aagaagccat actaaagctt    660
ccggtctgcg gtctttcacg agagatatcg tacgttctgg aatatggttg gcatataaat    720
ttgccaagat tggaagcaag gaactacatc gacgtatttg gacaggaccc catttatttg    780
acgccaaata tgaagaccca aaaacttcta gaacttgcaa agttggagtt caatatgttt    840
cactctttac aacagcaaga gctaaagctt ctctccagat ggtggaaaga ttcgggtttc    900
tctcaaatga ccttccctcg gcatcgtcac gtggaatatt acactttggc atcttgcatt    960
gatagtgaac ctcaacattc ttcgttcaga cttggatttg ccaaaatatt tcatcttgcc   1020
acggttcttg acgatattta cgacaccttt ggcacgatgg atgagctaga actcttcaca   1080
gcggcagtta agaggtggca tccgtctgcg acggagtggc ttccagaata tatgaaagga   1140
gtatatatgg tgctttacga aaccgttaac gaaatggcag gagaagcaga aaagtctcaa   1200
ggccgagaca cgctcaacta tgcccgaaat gctttggagg cttatattga tgcttctatg   1260
gaagaagcga agtggatttt cagtggtttt ttgccaacat ttgaggagta cctggataac   1320
gggaaagtta gtttcggtta taccattggc acattgcaac ccattctgac gttgggcatt   1380
ccctttcctc atcacatcct acaagaaata gactttcctt ccaggctcaa tgatgtggca   1440
tgttccattc tccgactaaa aggcgacgtt cacacttacc aggctgagag gagccgtgga   1500
gaagaatctt cgtgtatatc atgttatatg gaagataatc ccgagtcaac agaggaagat   1560
gcaatcaatc atatcaactc catggtcgac aaattactca aggaactaaa ttgggagtat   1620
ctgagacctg atagcaatgt tccaatcact tccaagaaac atgcatttga cattctgaga   1680
gctttctacc atctctacaa ataccgagat ggctacagcg ttgcgaacta tgaaataaag   1740
aatttggtca tgacaactgt cattgagcct gtgcctttat aa                      1782
```

```
<210> SEQ ID NO 18
<211> LENGTH: 593
<212> TYPE: PRT
<213> ORGANISM: Pinus patula

<400> SEQUENCE: 18

Ser Ser Lys Val Lys Val Val Arg Arg Thr Ile Ser Thr Ser Ile Arg
 1               5                  10                  15

Met Cys Arg Ile Thr Thr Val Ser Gly Glu Gly Val Gln Arg Arg Ile
            20                  25                  30

Ala Asn His His Ser Asn Leu Trp Asp Asp Asn Phe Ile Gln Ser Leu
        35                  40                  45

Ser Thr Pro Tyr Gly Ala Ile Ser Tyr His Glu Ser Ala Gln Lys Leu
    50                  55                  60

Ile Gly Glu Val Lys Glu Met Ile Asn Ser Ile Ser Val Lys Asp Gly
65                  70                  75                  80

Glu Leu Ile Thr Pro Ser Asn Asp Leu Leu Met Arg Leu Ser Ile Val
```

```
                85                  90                  95

Asp Ser Ile Glu Arg Leu Gly Ile Asp Arg His Phe Lys Ser Glu Ile
            100                 105                 110

Lys Ser Ala Leu Asp Tyr Val Tyr Ser Tyr Trp Asn Glu Lys Gly Ile
        115                 120                 125

Gly Trp Gly Arg Asp Ser Val Val Ala Asp Leu Asn Ser Thr Ala Leu
    130                 135                 140

Gly Leu Arg Thr Leu Arg Leu His Gly Tyr Pro Val Ser Ser Asp Val
145                 150                 155                 160

Leu Gln His Phe Lys Glu Gln Lys Gly Gln Phe Ala Cys Ser Ala Ile
                165                 170                 175

Gln Thr Glu Gly Glu Ile Arg Ser Val Leu Asn Leu Phe Arg Ala Ser
            180                 185                 190

Gln Ile Ala Phe Pro Gly Glu Lys Val Met Glu Glu Ala Glu Val Phe
        195                 200                 205

Ser Thr Ile Tyr Leu Lys Glu Ala Ile Leu Lys Leu Pro Val Cys Gly
    210                 215                 220

Leu Ser Arg Glu Ile Ser Tyr Val Leu Glu Tyr Gly Trp His Ile Asn
225                 230                 235                 240

Leu Pro Arg Leu Glu Ala Arg Asn Tyr Ile Asp Val Phe Gly Gln Asp
                245                 250                 255

Pro Ile Tyr Leu Thr Pro Asn Met Lys Thr Gln Lys Leu Leu Glu Leu
            260                 265                 270

Ala Lys Leu Glu Phe Asn Met Phe His Ser Leu Gln Gln Gln Glu Leu
        275                 280                 285

Lys Leu Leu Ser Arg Trp Trp Lys Asp Ser Gly Phe Ser Gln Met Thr
    290                 295                 300

Phe Pro Arg His Arg His Val Glu Tyr Tyr Thr Leu Ala Ser Cys Ile
305                 310                 315                 320

Asp Ser Glu Pro Gln His Ser Ser Phe Arg Leu Gly Phe Ala Lys Ile
                325                 330                 335

Phe His Leu Ala Thr Val Leu Asp Asp Ile Tyr Asp Thr Phe Gly Thr
            340                 345                 350

Met Asp Glu Leu Glu Leu Phe Thr Ala Ala Val Glu Arg Trp His Pro
        355                 360                 365

Ser Ala Thr Glu Trp Leu Pro Glu Tyr Met Lys Gly Val Tyr Met Val
    370                 375                 380

Leu Tyr Glu Thr Val Asn Glu Met Ala Gly Glu Ala Glu Lys Ser Gln
385                 390                 395                 400

Gly Arg Asp Thr Leu Asn Tyr Ala Arg Asn Ala Leu Glu Ala Tyr Ile
                405                 410                 415

Asp Ala Ser Met Lys Glu Ala Lys Trp Ile Phe Ser Gly Phe Leu Pro
            420                 425                 430

Thr Phe Glu Glu Tyr Leu Asp Asn Gly Lys Val Ser Phe Gly Tyr Ser
        435                 440                 445

Ile Gly Thr Leu Gln Pro Ile Leu Thr Leu Gly Ile Pro Phe Pro His
    450                 455                 460

His Ile Leu Gln Glu Ile Asp Phe Pro Ser Arg Leu Asn Asp Val Ala
465                 470                 475                 480

Cys Ser Ile Leu Arg Leu Lys Gly Asp Ile His Thr Tyr Gln Ala Glu
                485                 490                 495

Arg Ser Arg Gly Glu Lys Ser Ser Cys Ile Ser Cys Tyr Met Glu Glu
            500                 505                 510
```

```
Asn Pro Glu Ser Thr Glu Glu Asp Ala Ile Asp His Ile Asn Ser Met
        515                 520                 525

Val Asp Lys Leu Leu Lys Glu Leu Asn Arg Glu Tyr Leu Arg Pro Asp
    530                 535                 540

Ser Asn Val Pro Ile Thr Ser Lys Lys His Ala Phe Asp Ile Leu Arg
545                 550                 555                 560

Ala Phe Tyr His Leu Tyr Lys Tyr Arg Asp Gly Phe Ser Val Ala Asn
                565                 570                 575

Tyr Glu Ile Lys Asn Leu Val Met Thr Thr Val Ile Glu Pro Val Pro
            580                 585                 590

Leu


<210> SEQ ID NO 19
<211> LENGTH: 593
<212> TYPE: PRT
<213> ORGANISM: Pinus pseudostrobus

<400> SEQUENCE: 19

Ser Ser Lys Val Lys Val Val Arg Arg Thr Ile Ser Thr Ser Ile Arg
 1               5                  10                  15

Met Cys Arg Ile Thr Thr Val Ser Gly Glu Gly Val Gln Arg Arg Ile
            20                  25                  30

Ala Asn His His Ser Asn Leu Trp Asp Asp Asn Phe Ile Gln Ser Leu
        35                  40                  45

Ser Thr Pro Tyr Gly Ala Ile Ser Tyr His Glu Ser Ala Gln Lys Leu
    50                  55                  60

Ile Gly Glu Val Lys Glu Ile Ile Asn Ser Ile Ser Val Lys Asp Gly
65                  70                  75                  80

Glu Leu Ile Thr Pro Ser Asn Asp Leu Leu Met Arg Leu Ser Ile Val
                85                  90                  95

Asp Ser Ile Glu Arg Leu Gly Ile Asp Arg His Phe Lys Ser Glu Ile
            100                 105                 110

Lys Ser Ala Leu Asp Tyr Val Tyr Ser Tyr Trp Asn Glu Lys Gly Ile
        115                 120                 125

Gly Trp Gly Arg Asp Ser Val Val Ala Asp Leu Asn Ser Thr Ala Leu
    130                 135                 140

Gly Leu Arg Thr Leu Arg Leu His Gly Tyr Pro Val Ser Ser Asp Val
145                 150                 155                 160

Leu Gln His Phe Lys Glu Gln Lys Gly Gln Phe Ala Cys Ser Ala Ile
                165                 170                 175

Gln Thr Glu Gly Glu Ile Arg Ser Val Leu Asn Leu Phe Arg Ala Ser
            180                 185                 190

Gln Ile Ala Phe Pro Gly Glu Lys Val Met Glu Glu Ala Glu Val Phe
        195                 200                 205

Ser Thr Ile Tyr Leu Lys Glu Ala Ile Leu Lys Leu Pro Val Cys Gly
    210                 215                 220

Leu Ser Arg Glu Ile Ser Tyr Val Leu Glu Tyr Gly Trp His Ile Asn
225                 230                 235                 240

Leu Pro Arg Leu Glu Ala Arg Asn Tyr Ile Asp Val Phe Gly Gln Asp
                245                 250                 255

Pro Ile Tyr Leu Thr Pro Asn Met Lys Thr Gln Lys Leu Leu Glu Leu
            260                 265                 270

Ala Lys Leu Glu Phe Asn Met Phe His Ser Leu Gln Gln Gln Glu Leu
        275                 280                 285
```

```
Lys Leu Leu Ser Arg Trp Trp Lys Asp Ser Gly Phe Ser Gln Met Thr
    290                 295                 300

Phe Pro Arg His Arg His Val Glu Tyr Tyr Thr Leu Ala Ser Cys Ile
305                 310                 315                 320

Asp Ser Glu Pro Gln His Ser Ser Phe Arg Leu Gly Phe Ala Lys Ile
                325                 330                 335

Phe His Leu Ala Thr Val Leu Asp Asp Ile Tyr Asp Thr Phe Gly Thr
            340                 345                 350

Met Asp Glu Leu Glu Leu Phe Thr Ala Ala Val Lys Arg Trp His Pro
        355                 360                 365

Ser Ala Thr Glu Trp Leu Pro Glu Tyr Met Lys Gly Val Tyr Met Val
    370                 375                 380

Leu Tyr Glu Thr Val Asn Glu Met Ala Gly Glu Ala Glu Lys Ser Gln
385                 390                 395                 400

Gly Arg Asp Thr Leu Asn Tyr Ala Arg Asn Ala Leu Glu Ala Tyr Ile
                405                 410                 415

Asp Ala Ser Met Lys Glu Ala Lys Trp Ile Phe Ser Gly Phe Leu Pro
            420                 425                 430

Thr Phe Glu Glu Tyr Leu Asp Asn Gly Lys Val Ser Phe Gly Tyr Ser
        435                 440                 445

Ile Gly Thr Leu Gln Pro Ile Leu Thr Leu Gly Ile Pro Phe Pro His
    450                 455                 460

His Ile Leu Gln Glu Ile Asp Phe Pro Ser Arg Leu Asn Asp Val Ala
465                 470                 475                 480

Cys Ser Ile Leu Arg Leu Lys Gly Asp Ile His Thr Tyr Gln Ala Glu
                485                 490                 495

Arg Ser Arg Gly Glu Lys Ser Ser Cys Ile Ser Cys Tyr Met Glu Glu
            500                 505                 510

Asn Pro Glu Ser Thr Glu Glu Asp Ala Ile Asn His Val Asn Ser Met
        515                 520                 525

Val Asp Lys Leu Leu Lys Glu Leu Asn Trp Glu Tyr Leu Arg Pro Asp
    530                 535                 540

Ser Asn Val Pro Ile Thr Ser Lys Lys His Ala Phe Asp Ile Leu Arg
545                 550                 555                 560

Ala Phe Tyr His Leu Tyr Lys Tyr Arg Asp Gly Phe Ser Val Ala Asn
                565                 570                 575

Tyr Glu Ile Lys Asn Leu Val Met Thr Thr Val Ile Glu Pro Val Pro
            580                 585                 590

Leu


<210> SEQ ID NO 20
<211> LENGTH: 593
<212> TYPE: PRT
<213> ORGANISM: Pinus cooperi

<400> SEQUENCE: 20

Ser Ser Lys Val Lys Val Val Arg Arg Thr Ile Ser Thr Ser Ile Arg
 1               5                  10                  15

Met Cys Arg Ile Thr Thr Val Ser Gly Glu Gly Val Gln Arg Arg Ile
            20                  25                  30

Ala Asn His His Ser Asn Leu Trp Asp Asp Asn Phe Ile Gln Ser Leu
        35                  40                  45

Ser Thr Pro Tyr Gly Ala Ile Ser Tyr His Glu Ser Ala Gln Lys Leu
    50                  55                  60
```

```
Ile Gly Glu Val Lys Glu Met Ile Asn Ser Ile Ser Val Lys Asp Gly
65                  70                  75                  80

Glu Leu Ile Thr Pro Ser Asn Asp Leu Leu Met Arg Leu Ser Ile Val
                85                  90                  95

Asp Ser Ile Glu Arg Leu Gly Ile Asp Arg His Phe Lys Ser Glu Ile
            100                 105                 110

Lys Ser Ala Leu Asp Tyr Val Tyr Ser Tyr Trp Asn Glu Lys Gly Ile
        115                 120                 125

Gly Trp Gly Arg Asp Ser Val Val Ala Asp Leu Asn Ser Thr Ala Leu
    130                 135                 140

Gly Leu Arg Thr Leu Arg Leu His Gly Tyr Pro Val Ser Ser Asp Val
145                 150                 155                 160

Leu Gln His Phe Lys Glu Gln Lys Gly Gln Phe Ala Cys Ser Ala Ile
                165                 170                 175

Gln Thr Glu Gly Glu Ile Arg Ser Val Leu Asn Leu Phe Arg Ala Ser
            180                 185                 190

Gln Ile Ala Phe Pro Gly Glu Lys Val Met Glu Glu Ala Glu Val Phe
        195                 200                 205

Ser Thr Ile Tyr Leu Lys Glu Ala Ile Leu Lys Leu Pro Val Cys Gly
    210                 215                 220

Leu Ser Arg Glu Ile Ser Tyr Val Leu Glu Tyr Gly Trp His Ile Asn
225                 230                 235                 240

Leu Pro Arg Leu Glu Ala Arg Asn Tyr Ile Asp Val Phe Gly Gln Asp
                245                 250                 255

Pro Ile Tyr Leu Thr Pro Asn Met Lys Thr Gln Lys Leu Leu Glu Leu
            260                 265                 270

Ala Lys Leu Glu Phe Asn Met Phe His Ser Leu Gln Gln Gln Glu Leu
        275                 280                 285

Lys Leu Leu Ser Arg Trp Trp Lys Asp Ser Gly Phe Ser Gln Met Thr
    290                 295                 300

Phe Pro Arg His Arg His Val Glu Tyr Tyr Thr Leu Ala Ser Cys Ile
305                 310                 315                 320

Asp Ser Glu Pro Gln His Ser Ser Phe Arg Leu Gly Phe Ala Lys Ile
                325                 330                 335

Phe His Leu Ala Thr Val Leu Asp Asp Ile Tyr Asp Thr Phe Gly Thr
            340                 345                 350

Met Asp Glu Leu Glu Leu Phe Thr Ala Ala Val Lys Arg Trp His Pro
        355                 360                 365

Ser Ala Thr Glu Trp Leu Pro Glu Tyr Met Lys Gly Val Tyr Met Val
    370                 375                 380

Leu Tyr Glu Thr Val Asn Glu Met Ala Gly Glu Ala Glu Lys Ser Gln
385                 390                 395                 400

Gly Arg Asp Thr Leu Asn Tyr Ala Arg Asn Ala Leu Glu Ala Tyr Ile
                405                 410                 415

Asp Ala Ser Met Lys Glu Ala Lys Trp Ile Phe Ser Gly Phe Leu Pro
            420                 425                 430

Thr Phe Glu Glu Tyr Leu Asp Asn Gly Lys Val Ser Phe Gly Tyr Ser
        435                 440                 445

Ile Gly Thr Leu Gln Pro Ile Leu Thr Leu Gly Ile Pro Phe Pro His
    450                 455                 460

His Ile Leu Gln Glu Ile Asp Phe Pro Ser Arg Leu Asn Asp Val Ala
465                 470                 475                 480
```

```
Cys Ser Ile Leu Arg Leu Lys Gly Asp Ile His Thr Tyr Gln Ala Glu
                485                 490                 495

Arg Ser Arg Gly Glu Lys Ser Ser Cys Ile Ser Cys Tyr Met Glu Glu
            500                 505                 510

Asn Pro Glu Ser Thr Glu Glu Asp Ala Ile Asn His Ile Asn Ser Met
        515                 520                 525

Val Asp Lys Leu Leu Lys Glu Leu Asn Trp Glu Tyr Leu Arg Pro Asp
    530                 535                 540

Ser Asn Val Pro Ile Thr Ser Lys Lys His Ala Phe Asp Ile Leu Thr
545                 550                 555                 560

Ala Phe Tyr His Leu Tyr Lys Tyr Arg Asp Gly Phe Ser Val Ala Asn
                565                 570                 575

Tyr Glu Ile Lys Asn Leu Val Met Thr Thr Val Ile Glu Pro Val Pro
            580                 585                 590

Leu


<210> SEQ ID NO 21
<211> LENGTH: 593
<212> TYPE: PRT
<213> ORGANISM: Pinus hartwegii

<400> SEQUENCE: 21

Ser Ser Lys Val Lys Val Val Arg Arg Thr Ile Ser Thr Ser Ile Arg
 1               5                  10                  15

Met Cys Arg Ile Thr Thr Val Ser Gly Glu Gly Val Gln Arg Arg Ile
            20                  25                  30

Ala Asn His His Ser Asn Leu Trp Asp Asp Asn Phe Ile Gln Ser Leu
        35                  40                  45

Ser Thr Pro Tyr Gly Ala Ile Ser Tyr His Glu Ser Ala Gln Lys Leu
    50                  55                  60

Ile Gly Glu Val Lys Glu Met Ile Asn Ser Ile Ser Val Lys Asp Gly
65                  70                  75                  80

Glu Leu Ile Thr Pro Ser Asn Asp Leu Leu Met Arg Leu Ser Ile Val
                85                  90                  95

Asp Ser Ile Glu Arg Leu Gly Ile Asp Arg His Phe Lys Ser Glu Ile
            100                 105                 110

Lys Ser Ala Leu Asp Tyr Val Tyr Ser Tyr Trp Asn Glu Lys Gly Ile
        115                 120                 125

Gly Trp Gly Arg Asp Ser Val Val Ala Asp Leu Asn Ser Thr Ala Leu
    130                 135                 140

Gly Leu Arg Thr Leu Arg Leu His Gly Tyr Pro Val Ser Ser Asp Val
145                 150                 155                 160

Leu Gln His Phe Lys Glu Gln Lys Gly Gln Phe Ala Cys Ser Ala Ile
                165                 170                 175

Gln Thr Glu Gly Glu Ile Arg Ser Val Leu Asn Leu Phe Arg Ala Ser
            180                 185                 190

Gln Ile Ala Phe Pro Gly Glu Lys Val Met Glu Glu Ala Glu Val Phe
        195                 200                 205

Ser Thr Ile Tyr Leu Lys Glu Ala Ile Leu Lys Leu Pro Val Cys Gly
    210                 215                 220

Leu Ser Arg Glu Ile Ser Tyr Val Leu Glu Tyr Gly Trp His Ile Asn
225                 230                 235                 240

Leu Pro Arg Leu Glu Ala Arg Asn Tyr Ile Asp Val Phe Gly Gln Asp
                245                 250                 255
```

```
Pro Ile Tyr Leu Thr Pro Asn Met Lys Thr Gln Lys Leu Leu Glu Leu
            260                 265                 270

Ala Lys Leu Glu Phe Asn Met Phe His Ser Leu Gln Gln Gln Glu Leu
        275                 280                 285

Lys Leu Leu Ser Arg Trp Trp Lys Asp Ser Gly Phe Ser Gln Met Thr
    290                 295                 300

Phe Pro Arg His Arg His Val Glu Tyr Tyr Thr Leu Ala Ser Cys Ile
305                 310                 315                 320

Asp Ser Glu Pro Gln Tyr Ser Ser Phe Arg Leu Gly Phe Ala Lys Ile
                325                 330                 335

Phe His Leu Ala Thr Val Leu Asp Asp Ile Tyr Asp Thr Phe Gly Thr
            340                 345                 350

Met Asp Glu Leu Glu Leu Phe Thr Ala Ala Val Lys Arg Trp His Pro
        355                 360                 365

Ser Ala Thr Glu Trp Leu Pro Glu Tyr Met Lys Gly Val Tyr Met Val
    370                 375                 380

Leu Tyr Glu Thr Val Asn Glu Met Ala Gly Glu Ala Glu Lys Ser Gln
385                 390                 395                 400

Gly Arg Asp Thr Leu Asn Tyr Ala Arg Asn Ala Leu Glu Ala Tyr Ile
                405                 410                 415

Asp Ala Ser Met Lys Glu Ala Lys Trp Ile Phe Ser Gly Phe Leu Pro
            420                 425                 430

Thr Phe Glu Glu Tyr Leu Asp Asn Gly Lys Val Ser Phe Gly Tyr Ser
        435                 440                 445

Ile Gly Thr Leu Gln Pro Ile Leu Thr Leu Gly Ile Pro Phe Pro His
    450                 455                 460

His Ile Leu Gln Glu Ile Asp Phe Pro Ser Arg Leu Asn Asp Val Ala
465                 470                 475                 480

Cys Ser Ile Leu Arg Leu Lys Gly Asp Ile His Thr Tyr Gln Ala Glu
                485                 490                 495

Arg Ser Arg Gly Glu Lys Ser Ser Cys Ile Ser Cys Tyr Met Glu Glu
            500                 505                 510

Asn Pro Glu Ser Thr Glu Glu Asp Ala Ile Asn His Ile Asn Ser Met
        515                 520                 525

Val Asp Lys Leu Leu Lys Glu Leu Asn Trp Glu Tyr Leu Arg Pro Asp
    530                 535                 540

Ser Asn Val Pro Ile Thr Ser Lys Lys His Ala Phe Asp Ile Leu Arg
545                 550                 555                 560

Ala Phe Tyr His Leu Tyr Lys Tyr Arg Asp Gly Phe Ser Val Ala Asn
                565                 570                 575

Tyr Glu Ile Lys Asn Leu Val Met Thr Thr Val Ile Glu Pro Val Pro
            580                 585                 590

Leu


<210> SEQ ID NO 22
<211> LENGTH: 593
<212> TYPE: PRT
<213> ORGANISM: Pinus ponderosa

<400> SEQUENCE: 22

Ser Ser Lys Val Lys Val Val Arg Arg Thr Ile Ser Thr Ser Ile Arg
 1               5                  10                  15

Met Cys Arg Ile Thr Thr Glu Ser Gly Glu Gly Val Gln Arg Arg Ile
            20                  25                  30
```

```
Ala Asn His His Ser Asn Leu Trp Asp Asp Asn Phe Ile Gln Ser Leu
        35                  40                  45

Ser Thr Pro Tyr Gly Ala Ile Ser Tyr His Glu Ser Ala Gln Lys Leu
    50                  55                  60

Ile Gly Glu Val Lys Glu Met Ile Asn Ser Ile Ser Leu Lys Asp Gly
65                  70                  75                  80

Glu Leu Ile Thr Pro Ser Asn Asp Leu Leu Met Arg Leu Ser Ile Val
                85                  90                  95

Asp Ser Ile Glu Arg Leu Gly Ile Asp Arg His Phe Lys Ser Glu Ile
            100                 105                 110

Lys Ser Ala Leu Asp Tyr Val Tyr Ser Tyr Trp Asn Glu Lys Gly Ile
        115                 120                 125

Gly Trp Gly Arg Asp Ser Val Val Ala Asp Leu Asn Ser Thr Ala Leu
    130                 135                 140

Gly Leu Arg Thr Leu Arg Leu His Gly Tyr Pro Val Ser Ser Asp Val
145                 150                 155                 160

Leu Gln His Phe Lys Glu Gln Lys Gly Gln Phe Ala Cys Ser Ala Ile
                165                 170                 175

Gln Thr Glu Gly Glu Ile Arg Ser Val Leu Asn Leu Phe Arg Ala Ser
            180                 185                 190

Gln Ile Ala Phe Pro Gly Glu Lys Val Met Glu Glu Ala Glu Val Phe
        195                 200                 205

Ser Thr Ile Tyr Leu Lys Glu Ala Ile Leu Lys Leu Pro Val Cys Gly
    210                 215                 220

Leu Ser Arg Glu Ile Ser Tyr Val Leu Glu Tyr Gly Trp His Ile Asn
225                 230                 235                 240

Leu Pro Arg Leu Glu Ala Arg Asn Tyr Ile Asp Val Phe Gly Gln Asp
                245                 250                 255

Pro Ile Tyr Leu Thr Pro Asn Met Lys Thr Gln Lys Leu Leu Glu Leu
            260                 265                 270

Ala Lys Leu Glu Phe Asn Met Phe His Ser Leu Gln Gln Gln Glu Leu
        275                 280                 285

Lys Leu Leu Ser Arg Trp Trp Lys Asp Ser Gly Phe Ser Gln Met Thr
    290                 295                 300

Phe Pro Arg His Arg His Val Glu Tyr Tyr Thr Leu Ala Ser Cys Ile
305                 310                 315                 320

Asp Ser Glu Pro Gln His Ser Ser Phe Arg Leu Gly Phe Ala Lys Ile
                325                 330                 335

Phe His Leu Ala Thr Val Leu Asp Asp Ile Tyr Asp Thr Phe Gly Thr
            340                 345                 350

Met Asp Glu Leu Glu Leu Phe Thr Ala Ala Val Lys Arg Trp His Pro
        355                 360                 365

Ser Ala Thr Glu Trp Leu Pro Glu Tyr Met Lys Gly Val Tyr Met Val
    370                 375                 380

Leu Tyr Glu Thr Val Asn Glu Met Ala Arg Glu Ala Glu Lys Ser Gln
385                 390                 395                 400

Gly Arg Asp Thr Leu Asn Tyr Ala Arg Asn Ala Leu Glu Ala Tyr Ile
                405                 410                 415

Asp Ala Ser Met Lys Glu Ala Lys Trp Ile Phe Ser Gly Phe Leu Pro
            420                 425                 430

Thr Phe Glu Glu Tyr Leu Asp Asn Gly Lys Val Ser Phe Gly Tyr Ser
        435                 440                 445

Ile Gly Thr Leu Gln Pro Ile Leu Thr Leu Gly Ile Pro Phe Pro His
```

```
    450                 455                 460

His Ile Leu Gln Glu Ile Asp Phe Pro Ser Arg Leu Asn Asp Val Ala
465                 470                 475                 480

Cys Ser Ile Leu Arg Leu Lys Gly Asp Ile His Thr Tyr Gln Ala Glu
                485                 490                 495

Arg Ser Arg Gly Glu Lys Ser Ser Cys Ile Ser Cys Tyr Met Glu Glu
            500                 505                 510

Asn Pro Glu Ser Thr Glu Glu Asp Ala Ile Asn His Ile Asn Ser Met
        515                 520                 525

Val Asp Lys Leu Leu Lys Glu Leu Asn Trp Glu Tyr Leu Arg Pro Asp
    530                 535                 540

Ser Asn Val Pro Ile Thr Ser Lys Lys His Ala Phe Asp Ile Leu Arg
545                 550                 555                 560

Thr Phe Tyr His Leu Tyr Lys Tyr Arg Asp Gly Phe Ser Val Ala Asn
                565                 570                 575

Tyr Glu Ile Lys Asn Leu Val Met Thr Thr Val Ile Glu Pro Val Pro
            580                 585                 590

Leu


<210> SEQ ID NO 23
<211> LENGTH: 593
<212> TYPE: PRT
<213> ORGANISM: Pinus ponderosa

<400> SEQUENCE: 23

Ser Ser Lys Val Lys Val Val Arg Arg Thr Ile Ser Thr Ser Ile Arg
 1               5                  10                  15

Met Cys Arg Ile Thr Thr Glu Ser Gly Glu Gly Val Gln Arg Arg Ile
            20                  25                  30

Ala Asn His His Ser Asn Leu Trp Asp Asp Asn Phe Ile Gln Ser Leu
        35                  40                  45

Ser Thr Pro Tyr Gly Ala Ile Ser Tyr His Glu Ser Ala Gln Lys Leu
    50                  55                  60

Ile Gly Glu Val Lys Glu Met Ile Asn Ser Ile Ser Leu Lys Asp Gly
65                  70                  75                  80

Glu Leu Ile Thr Pro Ser Asn Asp Leu Leu Met Arg Leu Ser Ile Val
                85                  90                  95

Asp Ser Ile Glu Arg Leu Gly Ile Asp Arg His Phe Lys Ser Glu Ile
            100                 105                 110

Lys Ser Ala Leu Asp Tyr Val Tyr Ser Tyr Trp Asn Glu Lys Gly Ile
        115                 120                 125

Gly Trp Gly Arg Asp Ser Val Val Ala Asp Leu Asn Ser Thr Ala Leu
    130                 135                 140

Gly Leu Arg Thr Leu Arg Leu His Gly Tyr Pro Val Ser Ser Asp Val
145                 150                 155                 160

Leu Gln His Phe Lys Glu Gln Lys Gly Gln Phe Ala Cys Ser Ala Ile
                165                 170                 175

Gln Thr Glu Gly Glu Ile Arg Ser Val Leu Asn Leu Phe Arg Ala Ser
            180                 185                 190

Gln Ile Ala Phe Pro Gly Glu Lys Val Met Glu Glu Ala Glu Val Phe
        195                 200                 205

Ser Thr Ile Tyr Leu Lys Glu Ala Ile Leu Lys Leu Pro Val Cys Gly
    210                 215                 220

Leu Ser Arg Glu Ile Ser Tyr Val Leu Glu Tyr Gly Trp His Ile Asn
```

```
225                 230                 235                 240

Leu Pro Arg Leu Glu Ala Arg Asn Tyr Ile Asp Val Phe Gly Gln Asp
                245                 250                 255

Pro Ile Tyr Leu Thr Pro Asn Met Lys Thr Gln Lys Phe Leu Glu Leu
            260                 265                 270

Ala Lys Leu Glu Phe Asn Met Phe His Ser Leu Gln Gln Gln Glu Leu
        275                 280                 285

Lys Leu Leu Ser Arg Trp Trp Lys Asp Ser Gly Phe Ser Gln Met Thr
    290                 295                 300

Phe Pro Arg His Arg His Val Glu Tyr Tyr Thr Leu Ala Ser Cys Ile
305                 310                 315                 320

Asp Ser Glu Pro Gln His Ser Ser Phe Arg Leu Gly Phe Ala Lys Ile
                325                 330                 335

Phe His Leu Ala Thr Val Leu Asp Asp Ile Tyr Asp Thr Phe Gly Thr
            340                 345                 350

Met Asp Glu Leu Glu Leu Phe Thr Ala Ala Val Lys Arg Trp His Pro
        355                 360                 365

Ser Ala Thr Glu Trp Leu Pro Glu Tyr Met Lys Gly Val Tyr Met Val
    370                 375                 380

Leu Tyr Glu Thr Val Asn Glu Met Ala Arg Glu Ala Glu Lys Ser Gln
385                 390                 395                 400

Gly Arg Asp Thr Leu Asn Tyr Ala Arg Asn Ala Leu Glu Ala Tyr Ile
                405                 410                 415

Asp Ala Ser Met Lys Glu Ala Lys Trp Ile Phe Ser Gly Phe Leu Pro
            420                 425                 430

Thr Phe Glu Glu Tyr Leu Tyr Asn Gly Lys Val Ser Phe Gly Tyr Ser
        435                 440                 445

Ile Gly Thr Leu Gln Pro Ile Leu Thr Leu Gly Ile Pro Phe Pro His
    450                 455                 460

His Ile Leu Gln Glu Ile Asp Phe Pro Ser Arg Leu Asn Asp Val Ala
465                 470                 475                 480

Cys Ser Ile Leu Arg Leu Lys Gly Asp Ile His Thr Tyr Gln Ala Glu
                485                 490                 495

Arg Ser Arg Gly Glu Lys Ser Ser Cys Ile Ser Cys Tyr Met Glu Glu
            500                 505                 510

Asn Pro Glu Ser Thr Glu Glu Asp Ala Ile Asn His Ile Asn Ser Met
        515                 520                 525

Val Asp Lys Leu Leu Lys Glu Leu Asn Trp Glu Tyr Leu Arg Pro Asp
    530                 535                 540

Ser Asn Val Pro Ile Thr Ser Lys Lys His Ala Phe Asp Ile Leu Arg
545                 550                 555                 560

Thr Phe Tyr His Leu Tyr Lys Tyr Arg Asp Gly Phe Ser Val Ala Asn
                565                 570                 575

Tyr Glu Ile Lys Asn Leu Val Met Thr Thr Val Ile Glu Pro Val Pro
            580                 585                 590

Leu


<210> SEQ ID NO 24
<211> LENGTH: 593
<212> TYPE: PRT
<213> ORGANISM: Pinus jeffreyi

<400> SEQUENCE: 24

Ser Ser Lys Val Lys Val Val Arg Arg Thr Ile Ser Thr Ser Ile Arg
```

-continued

```
1               5                   10                  15

Met Cys Arg Ile Thr Thr Glu Ser Gly Glu Gly Val Gln Arg Arg Ile
            20                  25                  30

Ala Asn His His Ser Asn Leu Trp Asp Asp Asn Phe Ile Gln Ser Leu
        35                  40                  45

Ser Thr Pro Tyr Gly Ala Ile Ser Tyr His Glu Ser Ala Gln Lys Leu
    50                  55                  60

Ile Gly Glu Val Lys Glu Met Ile Asn Ser Ile Ser Leu Lys Asp Gly
65                  70                  75                  80

Glu Leu Ile Thr Pro Ser Asn Asp Leu Leu Met Arg Leu Ser Ile Val
                85                  90                  95

Asp Ser Ile Glu Arg Leu Gly Ile Asp Arg His Phe Lys Ser Glu Ile
            100                 105                 110

Lys Ser Ala Leu Asp Tyr Val Tyr Ser Tyr Trp Asn Glu Lys Gly Ile
        115                 120                 125

Gly Trp Gly Arg Asp Ser Val Val Ala Asp Leu Asn Ser Thr Ala Leu
    130                 135                 140

Gly Leu Arg Thr Leu Arg Leu His Gly Tyr Pro Val Ser Ser Asp Val
145                 150                 155                 160

Leu Gln His Phe Lys Glu Gln Lys Gly Gln Phe Ala Cys Ser Ala Ile
                165                 170                 175

Gln Thr Glu Gly Glu Ile Arg Ser Val Leu Asn Leu Phe Arg Ala Ser
            180                 185                 190

Gln Ile Ala Phe Pro Gly Glu Lys Val Met Glu Glu Ala Glu Val Phe
        195                 200                 205

Ser Thr Ile Tyr Leu Lys Glu Ala Ile Leu Lys Leu Pro Val Cys Gly
    210                 215                 220

Leu Ser Arg Glu Ile Ser Tyr Val Leu Glu Tyr Gly Trp His Ile Asn
225                 230                 235                 240

Leu Pro Arg Leu Glu Ala Arg Asn Tyr Ile Asp Val Phe Gly Gln Asp
                245                 250                 255

Pro Ile Tyr Leu Thr Pro Asn Met Lys Thr Gln Lys Leu Leu Glu Leu
            260                 265                 270

Ala Lys Leu Glu Phe Asn Met Phe His Ser Leu Gln Gln Gln Glu Leu
        275                 280                 285

Lys Leu Leu Ser Arg Trp Trp Lys Asp Ser Gly Phe Ser Gln Met Thr
    290                 295                 300

Phe Pro Arg His Arg His Val Glu Tyr Tyr Thr Leu Ala Ser Cys Ile
305                 310                 315                 320

Asp Ser Glu Pro Gln His Ser Ser Phe Arg Leu Gly Phe Ala Lys Ile
                325                 330                 335

Phe His Leu Ala Thr Val Leu Asp Asp Ile Tyr Asp Thr Phe Gly Thr
            340                 345                 350

Met Asp Glu Leu Glu Leu Phe Thr Ala Ala Val Lys Arg Trp His Pro
        355                 360                 365

Ser Ala Thr Glu Trp Leu Pro Glu Tyr Met Lys Gly Val Tyr Met Val
    370                 375                 380

Leu Tyr Glu Thr Val Asn Glu Met Ala Gly Glu Ala Glu Lys Ser Gln
385                 390                 395                 400

Gly Arg Asp Thr Leu Asn Tyr Ala Arg Asn Ala Ser Glu Ala Tyr Ile
                405                 410                 415

Asp Ala Ser Met Lys Glu Ala Lys Trp Ile Phe Ser Gly Phe Leu Pro
            420                 425                 430
```

```
Thr Phe Glu Glu Tyr Leu Asp Asn Gly Lys Val Ser Phe Gly Tyr Ser
        435                 440                 445

Ile Gly Thr Leu Gln Pro Ile Leu Thr Leu Gly Ile Pro Phe Pro His
    450                 455                 460

His Ile Leu Gln Glu Ile Asp Phe Pro Ser Arg Leu Asn Asp Val Ala
465                 470                 475                 480

Cys Ser Ile Leu Arg Leu Lys Gly Asp Ile His Thr Tyr Gln Ala Glu
                485                 490                 495

Arg Ser Arg Gly Glu Lys Ser Ser Cys Ile Ser Cys Tyr Met Glu Glu
            500                 505                 510

Asn Pro Glu Ser Thr Glu Glu Asp Ala Ile Asn His Ile Asn Ser Met
        515                 520                 525

Val Asp Lys Leu Leu Lys Glu Leu Asn Trp Glu Tyr Leu Arg Pro Asp
    530                 535                 540

Ser Asn Val Pro Ile Thr Ser Lys Lys His Ala Phe Asp Ile Leu Arg
545                 550                 555                 560

Ala Phe Tyr His Leu Tyr Lys Tyr Arg Asp Gly Phe Ser Val Ala Asn
                565                 570                 575

Tyr Glu Ile Lys Asn Leu Val Met Thr Thr Val Ile Glu Pro Val Pro
            580                 585                 590

Leu


<210> SEQ ID NO 25
<211> LENGTH: 593
<212> TYPE: PRT
<213> ORGANISM: Pinus montezumae

<400> SEQUENCE: 25

Ser Ser Lys Val Lys Val Val Arg Arg Thr Ile Ser Thr Ser Ile Arg
 1               5                  10                  15

Met Cys Arg Ile Thr Thr Val Ser Gly Glu Gly Val Gln Arg Arg Ile
            20                  25                  30

Ala Asn His His Ser Asn Leu Trp Asp Asp Asn Phe Ile Gln Ser Leu
        35                  40                  45

Ser Thr Pro Tyr Gly Ala Ile Ser Tyr His Glu Ser Ala Gln Lys Leu
    50                  55                  60

Ile Gly Glu Val Lys Glu Met Ile Asn Ser Ile Ser Val Lys Asp Gly
65                  70                  75                  80

Glu Leu Ile Thr Pro Ser Asn Asp Leu Leu Met Arg Leu Ser Ile Val
                85                  90                  95

Asp Ser Ile Glu Arg Leu Gly Ile Asp Arg His Phe Lys Ser Glu Ile
            100                 105                 110

Lys Ser Ala Leu Asp Tyr Val Tyr Ser Tyr Trp Asn Glu Lys Gly Ile
        115                 120                 125

Gly Trp Gly Arg Asp Ser Val Val Ala Asp Leu Asn Ser Thr Ala Leu
    130                 135                 140

Gly Leu Arg Thr Leu Arg Leu His Gly Tyr Pro Val Ser Ser Asp Val
145                 150                 155                 160

Leu Gln His Phe Lys Glu Gln Lys Gly Gln Phe Ala Cys Ser Ala Ile
                165                 170                 175

Gln Thr Glu Gly Glu Ile Arg Ser Val Leu Asn Leu Phe Arg Ala Ser
            180                 185                 190

Gln Ile Ala Phe Pro Gly Glu Lys Val Met Glu Glu Ala Glu Val Phe
        195                 200                 205
```

```
Ser Thr Ile Tyr Leu Lys Glu Ala Ile Leu Lys Leu Pro Val Cys Gly
    210                 215                 220

Leu Ser Arg Glu Ile Ser Tyr Val Leu Glu Tyr Gly Trp His Ile Asn
225                 230                 235                 240

Leu Pro Arg Leu Glu Ala Arg Asn Tyr Ile Asp Val Phe Gly Gln Asp
                245                 250                 255

Pro Ile Tyr Leu Thr Pro Asn Met Lys Thr Gln Lys Leu Leu Glu Leu
            260                 265                 270

Ala Lys Leu Glu Phe Asn Met Phe His Ser Leu Gln Gln Gln Glu Leu
        275                 280                 285

Lys Leu Leu Ser Arg Trp Trp Lys Asp Ser Gly Phe Ser Gln Met Thr
    290                 295                 300

Phe Pro Arg His Arg His Val Glu Tyr Tyr Thr Leu Ala Ser Cys Ile
305                 310                 315                 320

Asp Ser Glu Pro Gln His Ser Ser Phe Arg Leu Gly Phe Ala Lys Met
                325                 330                 335

Phe His Leu Ala Thr Val Leu Asp Asp Ile Tyr Asp Thr Phe Gly Thr
            340                 345                 350

Met Asp Glu Leu Glu Leu Phe Thr Ala Ala Val Lys Arg Trp His Pro
        355                 360                 365

Ser Ala Thr Glu Trp Leu Pro Glu Tyr Met Lys Gly Val Tyr Met Val
    370                 375                 380

Leu Tyr Glu Thr Val Asn Glu Met Ala Gly Glu Ala Glu Lys Ser Gln
385                 390                 395                 400

Gly Arg Asp Thr Leu Asn Tyr Ala Arg Asn Ala Leu Glu Ala Tyr Ile
                405                 410                 415

Asp Ala Ser Met Lys Glu Ala Lys Trp Ile Phe Ser Gly Phe Leu Pro
            420                 425                 430

Thr Phe Glu Glu Tyr Leu Asp Asn Gly Lys Val Ser Phe Gly Tyr Ser
        435                 440                 445

Ile Gly Thr Leu Gln Pro Ile Leu Thr Leu Gly Ile Pro Phe Pro His
    450                 455                 460

His Ile Leu Gln Glu Ile Asp Phe Pro Ser Arg Leu Asn Asp Val Ala
465                 470                 475                 480

Cys Ser Ile Leu Arg Leu Lys Gly Asp Ile His Thr Tyr Glu Ala Glu
                485                 490                 495

Arg Ser Arg Gly Glu Lys Ser Ser Cys Ile Ser Cys Tyr Met Glu Glu
            500                 505                 510

Asn Pro Glu Ser Thr Glu Glu Asp Ala Ile Asn His Ile Asn Ser Met
        515                 520                 525

Val Asp Lys Leu Leu Lys Glu Leu Asn Trp Glu Tyr Leu Arg Pro Asp
    530                 535                 540

Ser Asn Val Pro Ile Thr Ser Lys Lys His Ala Phe Asp Ile Leu Arg
545                 550                 555                 560

Ala Phe Tyr His Leu Tyr Lys Tyr Arg Asp Gly Phe Ser Val Ala Asn
                565                 570                 575

Tyr Glu Ile Lys Asn Leu Val Met Thr Thr Val Ile Glu Pro Val Pro
            580                 585                 590

Leu
```

<210> SEQ ID NO 26
<211> LENGTH: 564
<212> TYPE: PRT

```
<213> ORGANISM: Pinus pseudostrobus
<220> FEATURE:
<221> NAME/KEY: VARIANT
<222> LOCATION: (1)...(564)
<223> OTHER INFORMATION: Xaa = any amino acid

<400> SEQUENCE: 26

Arg Arg Xaa Xaa Xaa Xaa His Ser Asn Leu Trp Asp Asp Asn Phe Ile
 1               5                  10                  15

Gln Ser Leu Ser Thr Pro Tyr Gly Ala Ile Ser Tyr His Glu Ser Ala
            20                  25                  30

Gln Lys Leu Ile Gly Glu Val Lys Glu Met Ile Asn Ser Ile Ser Val
        35                  40                  45

Lys Asp Gly Glu Leu Ile Thr Pro Ser Asn Asp Leu Leu Met Arg Leu
    50                  55                  60

Ser Ile Val Asp Ser Ile Glu Arg Leu Gly Ile Asp Arg His Phe Lys
65                  70                  75                  80

Ser Glu Ile Lys Ser Ala Leu Asp Tyr Val Tyr Ser Tyr Trp Asn Glu
                85                  90                  95

Lys Gly Ile Gly Trp Gly Arg Asp Ser Val Val Ala Asp Leu Asn Ser
            100                 105                 110

Thr Ala Leu Gly Leu Arg Thr Leu Arg Leu His Gly Tyr Pro Val Ser
        115                 120                 125

Ser Asp Val Leu Gln His Phe Lys Glu Gln Lys Gly Gln Phe Ala Cys
    130                 135                 140

Ser Ala Ile Gln Thr Glu Gly Glu Ile Arg Ser Val Leu Asn Leu Phe
145                 150                 155                 160

Arg Ala Ser Gln Ile Ala Phe Pro Gly Glu Lys Val Met Glu Glu Ala
                165                 170                 175

Glu Val Phe Ser Thr Ile Tyr Leu Lys Glu Ala Ile Leu Lys Leu Pro
            180                 185                 190

Val Cys Gly Leu Ser Arg Glu Ile Ser Tyr Val Leu Glu Tyr Gly Trp
        195                 200                 205

His Ile Asn Leu Pro Arg Leu Glu Ala Arg Asn Tyr Ile Asp Val Phe
    210                 215                 220

Gly Gln Asp Pro Ile Tyr Leu Thr Pro Asn Met Lys Thr Gln Lys Leu
225                 230                 235                 240

Leu Glu Leu Ala Lys Leu Glu Phe Asn Met Phe His Ser Leu Gln Gln
                245                 250                 255

Gln Glu Leu Lys Leu Leu Ser Arg Trp Trp Lys Asp Ser Gly Phe Ser
            260                 265                 270

Gln Met Thr Phe Pro Arg His Arg His Val Glu Tyr Tyr Thr Leu Ala
        275                 280                 285

Ser Cys Ile Asp Ser Glu Pro Gln His Ser Ser Phe Arg Leu Gly Phe
    290                 295                 300

Ala Lys Met Phe His Leu Ala Thr Val Leu Asp Asp Ile Tyr Asp Thr
305                 310                 315                 320

Phe Gly Thr Met Asp Glu Leu Glu Leu Phe Thr Ala Ala Val Lys Arg
                325                 330                 335

Trp His Pro Ser Ala Thr Glu Trp Leu Pro Glu Tyr Met Lys Gly Val
            340                 345                 350

Tyr Met Val Leu Tyr Glu Thr Val Asn Glu Met Ala Gly Glu Ala Glu
        355                 360                 365

Lys Ser Gln Gly Arg Asp Thr Leu Asn Tyr Ala Arg Asn Ala Leu Glu
    370                 375                 380
```

```
Ala Tyr Ile Asp Ala Ser Met Lys Glu Ala Lys Trp Ile Phe Ser Gly
385                 390                 395                 400

Phe Leu Pro Thr Phe Glu Glu Tyr Leu Asp Asn Gly Lys Val Ser Phe
                405                 410                 415

Gly Tyr Ser Ile Gly Thr Leu Gln Pro Ile Leu Thr Leu Gly Ile Pro
            420                 425                 430

Phe Pro His His Ile Leu Gln Glu Ile Asp Phe Pro Ser Arg Leu Asn
        435                 440                 445

Asp Val Ala Cys Ser Ile Leu Arg Leu Lys Gly Asp Ile His Thr Tyr
    450                 455                 460

Glu Ala Glu Arg Ser Arg Gly Glu Lys Ser Ser Cys Ile Ser Cys Tyr
465                 470                 475                 480

Met Glu Glu Asn Pro Glu Ser Thr Glu Glu Asp Ala Ile Asn His Ile
                485                 490                 495

Asn Ser Met Val Asp Lys Leu Leu Lys Glu Leu Asn Trp Glu Tyr Leu
            500                 505                 510

Arg Pro Asp Ser Asn Val Pro Ile Thr Ser Lys Lys His Ala Phe Asp
        515                 520                 525

Ile Leu Arg Ala Phe Tyr His Leu Tyr Lys Tyr Arg Asp Gly Phe Ser
    530                 535                 540

Val Ala Asn Tyr Glu Ile Lys Asn Leu Val Met Thr Thr Val Ile Glu
545                 550                 555                 560

Pro Val Pro Leu


<210> SEQ ID NO 27
<211> LENGTH: 590
<212> TYPE: PRT
<213> ORGANISM: Pinus sabiniana

<400> SEQUENCE: 27

Ser Ser Lys Val Lys Val Val Arg Arg Thr Ile Ser Thr Ser Ile Arg
 1               5                  10                  15

Met Cys Arg Ile Thr Thr Glu Ser Gly Glu Gly Val Gln Arg Arg Ile
            20                  25                  30

Ala Asn His His Ser Asn Leu Trp Asp Asp Asn Phe Ile Gln Ser Leu
        35                  40                  45

Ser Thr Pro Tyr Gly Ala Ile Ser Tyr His Glu Ser Ala Gln Lys Leu
    50                  55                  60

Ile Gly Glu Val Lys Glu Met Ile Asn Ser Ile Ser Val Lys Asp Gly
65                  70                  75                  80

Glu Leu Ile Thr Pro Ser Asn Asp Leu Leu Met Arg Leu Ser Ile Val
                85                  90                  95

Asp Ser Ile Glu Arg Leu Gly Ile Asp Arg His Phe Lys Ser Glu Ile
            100                 105                 110

Lys Ser Ala Leu Asp Tyr Val Tyr Ser Tyr Trp Asn Glu Lys Gly Ile
        115                 120                 125

Gly Trp Gly Arg Asp Ser Val Val Ala Asp Leu Asn Ser Thr Ala Leu
    130                 135                 140

Gly Leu Arg Thr Leu Arg Leu His Gly Tyr Pro Val Ser Ser Asp Val
145                 150                 155                 160

Leu Gln His Phe Lys Glu Gln Lys Gly Gln Phe Ala Cys Ser Ala Ile
                165                 170                 175

Gln Thr Glu Gly Glu Ile Arg Ser Val Leu Asn Leu Phe Arg Ala Ser
            180                 185                 190
```

```
Gln Ile Ala Phe Pro Gly Glu Lys Val Met Glu Glu Ala Glu Val Phe
        195                 200                 205

Ser Thr Ile Tyr Leu Lys Glu Ala Ile Leu Lys Leu Pro Val Cys Gly
    210                 215                 220

Leu Ser Arg Glu Ile Ser Tyr Val Leu Glu Tyr Gly Trp His Ile Asn
225                 230                 235                 240

Leu Pro Arg Leu Glu Ala Arg Asn Tyr Ile Asp Val Phe Gly Glu Asp
                245                 250                 255

Pro Ile Tyr Leu Thr Pro Asn Met Lys Thr Gln Lys Leu Leu Glu Leu
            260                 265                 270

Ala Lys Leu Glu Phe Asn Met Phe His Ser Leu Gln Gln Gln Glu Leu
        275                 280                 285

Lys Leu Leu Ser Arg Trp Trp Lys Asp Ser Gly Phe Ser Gln Met Thr
    290                 295                 300

Phe Pro Arg His Arg His Val Glu Tyr Tyr Thr Leu Ala Ser Cys Ile
305                 310                 315                 320

Asp Ser Glu Pro Gln His Ser Ser Phe Arg Leu Gly Phe Ala Lys Ile
                325                 330                 335

Phe His Leu Ala Thr Val Leu Asp Asp Ile Tyr Asp Thr Phe Gly Thr
            340                 345                 350

Met Asp Glu Leu Glu Leu Phe Thr Ala Ala Val Lys Arg Trp His Pro
        355                 360                 365

Ser Ala Thr Glu Trp Leu Pro Glu Tyr Met Lys Gly Val Tyr Met Val
    370                 375                 380

Leu Tyr Glu Thr Val Asn Glu Met Ala Gly Glu Ala Glu Lys Ser Gln
385                 390                 395                 400

Gly Arg Asp Thr Leu Asn Tyr Gly Arg Asn Ala Leu Glu Ala Tyr Ile
                405                 410                 415

Asp Ala Ser Met Glu Glu Ala Lys Trp Ile Phe Ser Gly Phe Leu Pro
            420                 425                 430

Thr Phe Glu Glu Tyr Leu Asp Asn Gly Lys Val Ser Phe Gly Tyr Gly
        435                 440                 445

Ile Gly Thr Leu Gln Pro Ile Leu Thr Leu Gly Ile Pro Phe Pro His
    450                 455                 460

His Ile Leu Gln Glu Ile Asp Phe Pro Ser Arg Leu Asn Asp Val Ala
465                 470                 475                 480

Ser Ser Ile Leu Arg Leu Lys Gly Asp Ile His Thr Tyr Gln Ala Glu
                485                 490                 495

Arg Ser Arg Gly Glu Lys Ser Ser Cys Ile Ser Cys Tyr Met Glu Glu
            500                 505                 510

Asn Pro Glu Ser Thr Glu Glu Asp Ala Ile Asn His Ile Asn Ser Met
        515                 520                 525

Val Asp Lys Leu Leu Lys Glu Leu Asn Trp Glu Tyr Leu Arg Pro Asp
    530                 535                 540

Ser Asn Val Pro Ile Thr Ser Lys Lys His Ala Phe Asp Ile Leu Arg
545                 550                 555                 560

Ala Phe Tyr His Leu Tyr Lys Tyr Arg Asp Gly Phe Ser Val Ala Asn
                565                 570                 575

Tyr Glu Ile Lys Asn Leu Val Met Thr Thr Val Ile Glu Pro
            580                 585                 590
```

<210> SEQ ID NO 28
<211> LENGTH: 593

```
<212> TYPE: PRT
<213> ORGANISM: Pinus sabiniana

<400> SEQUENCE: 28

Ser Ser Lys Val Lys Val Val Arg Arg Thr Ile Ser Thr Ser Ile Arg
 1               5                  10                  15

Met Cys Arg Ile Thr Thr Glu Ser Gly Glu Gly Val Gln Arg Arg Ile
            20                  25                  30

Ala Asn His His Ser Asn Leu Trp Asp Asp Asn Phe Ile Gln Ser Leu
        35                  40                  45

Ser Thr Pro Tyr Gly Ala Ile Ser Tyr His Glu Ser Ala Gln Lys Leu
    50                  55                  60

Ile Gly Glu Val Lys Glu Met Ile Asn Ser Ile Ser Leu Lys Asp Gly
65                  70                  75                  80

Glu Leu Ile Thr Pro Ser Asn Asp Leu Leu Met Arg Leu Ser Ile Val
                85                  90                  95

Asp Ser Ile Glu Arg Leu Gly Ile Asp Arg His Phe Lys Ser Glu Ile
            100                 105                 110

Lys Ser Ala Leu Asp Tyr Val Tyr Ser Tyr Trp Asn Glu Lys Gly Ile
        115                 120                 125

Gly Trp Gly Arg Asp Ser Val Val Ala Asp Leu Asn Ser Thr Ala Leu
    130                 135                 140

Gly Leu Arg Thr Leu Arg Leu His Gly Tyr Pro Val Ser Ser Asp Val
145                 150                 155                 160

Leu Gln His Phe Lys Glu Gln Lys Gly Gln Phe Ala Cys Ser Ala Ile
                165                 170                 175

Gln Thr Glu Gly Glu Ile Arg Ser Val Leu Asn Leu Phe Arg Ala Ser
            180                 185                 190

Gln Ile Ala Phe Pro Gly Glu Lys Val Met Glu Glu Ala Glu Val Phe
        195                 200                 205

Ser Thr Ile Tyr Leu Lys Glu Ala Ile Leu Lys Leu Pro Val Cys Gly
    210                 215                 220

Leu Ser Arg Glu Ile Ser Tyr Val Leu Glu Tyr Gly Trp His Ile Asn
225                 230                 235                 240

Leu Pro Arg Leu Glu Ala Arg Asn Tyr Ile Asp Val Phe Gly Glu Asp
                245                 250                 255

Pro Ile Tyr Leu Thr Pro Asn Met Lys Thr Gln Lys Leu Leu Glu Leu
            260                 265                 270

Ala Lys Leu Glu Phe Asn Met Phe His Ser Leu Gln Gln Gln Glu Leu
        275                 280                 285

Lys Leu Leu Ser Arg Trp Trp Lys Asp Ser Gly Phe Ser Gln Met Thr
    290                 295                 300

Phe Pro Arg His Arg His Val Glu Tyr Tyr Thr Leu Ala Ser Cys Ile
305                 310                 315                 320

Asp Ser Glu Pro Gln His Ser Ser Phe Arg Leu Gly Phe Ala Lys Ile
                325                 330                 335

Phe His Leu Ala Thr Val Leu Asp Asp Ile Tyr Asp Thr Phe Gly Thr
            340                 345                 350

Met Asp Glu Leu Glu Leu Phe Thr Ala Ala Val Lys Arg Trp His Pro
        355                 360                 365

Ser Ala Thr Glu Trp Leu Pro Glu Tyr Met Lys Gly Val Tyr Met Val
    370                 375                 380

Leu Tyr Glu Thr Val Asn Glu Met Ala Gly Glu Ala Glu Lys Ser Gln
385                 390                 395                 400
```

```
Gly Arg Asp Thr Leu Asn Tyr Gly Arg Asn Ala Leu Glu Ala Tyr Ile
                405                 410                 415

Asp Ala Ser Met Glu Glu Ala Lys Trp Ile Phe Ser Gly Phe Leu Pro
            420                 425                 430

Thr Phe Glu Glu Tyr Leu Asp Asn Gly Lys Val Ser Phe Gly Tyr Gly
        435                 440                 445

Ile Gly Thr Leu Gln Pro Ile Leu Thr Leu Gly Ile Pro Phe Pro His
    450                 455                 460

His Ile Leu Gln Glu Ile Asp Phe Pro Ser Arg Leu Asn Asp Val Ala
465                 470                 475                 480

Ser Ser Ile Leu Arg Leu Lys Gly Asp Ile His Thr Tyr Gln Ala Glu
                485                 490                 495

Arg Ser Arg Gly Glu Lys Ser Ser Cys Ile Ser Cys Tyr Met Glu Glu
            500                 505                 510

Asn Pro Glu Ser Thr Glu Glu Asp Ala Ile Asn His Ile Asn Ser Met
        515                 520                 525

Val Asp Lys Leu Leu Lys Glu Leu Asn Trp Glu Tyr Leu Arg Pro Asp
    530                 535                 540

Ser Asn Val Pro Ile Thr Ser Lys Lys His Ala Phe Asp Ile Leu Arg
545                 550                 555                 560

Ala Phe Tyr His Leu Tyr Lys Tyr Arg Asp Gly Phe Ser Val Ala Asn
                565                 570                 575

Tyr Glu Ile Lys Asn Leu Val Met Thr Thr Val Ile Glu Pro Val Pro
            580                 585                 590

Leu


<210> SEQ ID NO 29
<211> LENGTH: 564
<212> TYPE: PRT
<213> ORGANISM: Pinus coulteri
<220> FEATURE:
<221> NAME/KEY: VARIANT
<222> LOCATION: (1)...(564)
<223> OTHER INFORMATION: Xaa = Any Amino Acid

<400> SEQUENCE: 29

Arg Arg Ile Ala Gly His His Ser Asn Leu Trp Asp Asp Asx Xaa Ile
 1               5                  10                  15

Gln Ser Leu Ser Thr Pro Tyr Gly Ala Ile Ser Tyr His Glu Ser Ala
            20                  25                  30

Gln Lys Leu Ile Gly Glu Val Lys Glu Met Ile Asn Ser Ile Ser Val
        35                  40                  45

Lys Asp Gly Glu Leu Ile Thr Pro Ser Asn Asp Leu Leu Met Arg Leu
    50                  55                  60

Ser Ile Val Asp Ser Ile Glu Arg Leu Gly Ile Asp Arg His Phe Lys
65                  70                  75                  80

Ser Glu Ile Lys Ser Ala Leu Asp Tyr Val Tyr Ser Tyr Trp Asn Glu
                85                  90                  95

Lys Gly Ile Gly Trp Gly Arg Asp Ser Val Val Ala Asp Leu Asn Ser
            100                 105                 110

Thr Ala Leu Gly Leu Arg Thr Leu Arg Leu His Gly Tyr Pro Val Ser
        115                 120                 125

Ser Asp Val Leu Gln His Phe Lys Glu Gln Lys Gly Gln Phe Ala Cys
    130                 135                 140

Ser Ala Ile Gln Thr Glu Gly Glu Ile Arg Ser Val Leu Asn Leu Phe
```

```
145                 150                 155                 160

Arg Ala Ser Gln Ile Ala Phe Pro Gly Glu Lys Val Met Glu Glu Ala
                165                 170                 175

Glu Val Phe Ser Thr Ile Tyr Leu Lys Glu Ala Ile Leu Lys Leu Pro
            180                 185                 190

Val Cys Gly Leu Ser Arg Glu Ile Ser Tyr Val Leu Glu Tyr Gly Trp
        195                 200                 205

His Ile Asn Leu Pro Arg Leu Glu Ala Arg Asn Tyr Ile Asp Val Phe
    210                 215                 220

Gly Glu Asp Pro Ile Tyr Leu Thr Pro Asn Met Lys Thr Gln Lys Leu
225                 230                 235                 240

Leu Glu Leu Ala Lys Leu Glu Phe Asn Met Phe His Ser Leu Gln Gln
                245                 250                 255

Gln Glu Leu Lys Leu Leu Ser Arg Trp Trp Lys Asp Ser Gly Phe Ser
            260                 265                 270

Gln Met Thr Phe Pro Arg His Arg His Val Glu Tyr Tyr Thr Leu Ala
        275                 280                 285

Ser Cys Ile Asp Ser Glu Pro Gln His Ser Ser Phe Arg Leu Gly Phe
    290                 295                 300

Ala Lys Ile Phe His Leu Ala Thr Val Leu Asp Asp Ile Tyr Asp Thr
305                 310                 315                 320

Phe Gly Thr Met Asp Glu Leu Glu Leu Phe Thr Ala Ala Val Lys Arg
                325                 330                 335

Trp His Pro Ser Ala Thr Glu Trp Leu Pro Glu Tyr Met Lys Gly Val
            340                 345                 350

Tyr Met Val Leu Tyr Glu Thr Val Asn Glu Met Ala Gly Glu Ala Glu
        355                 360                 365

Lys Ser Gln Gly Arg Asp Thr Leu Asn Tyr Gly Arg Asn Ala Leu Glu
    370                 375                 380

Ala Tyr Ile Asp Ala Ser Met Glu Glu Ala Lys Trp Ile Phe Ser Gly
385                 390                 395                 400

Phe Leu Pro Thr Phe Glu Glu Tyr Leu Asp Asn Gly Lys Val Ser Phe
                405                 410                 415

Gly Tyr Gly Ile Gly Thr Leu Gln Pro Ile Leu Thr Leu Gly Ile Pro
            420                 425                 430

Phe Pro His His Ile Leu Gln Glu Ile Asp Phe Pro Ser Arg Leu Asn
        435                 440                 445

Asp Val Ala Ser Ser Ile Leu Arg Leu Lys Gly Asp Ile His Thr Tyr
    450                 455                 460

Gln Ala Glu Arg Ser Arg Gly Glu Lys Ser Ser Cys Ile Ser Cys Tyr
465                 470                 475                 480

Met Glu Glu Asn Pro Glu Ser Thr Glu Glu Asp Ala Ile Asn His Ile
                485                 490                 495

Asn Ser Met Val Asp Lys Leu Leu Lys Glu Leu Asn Trp Glu Tyr Leu
            500                 505                 510

Arg Pro Asp Ser Asn Val Pro Ile Thr Ser Lys Lys His Ala Phe Asp
        515                 520                 525

Ile Leu Arg Ala Phe Tyr His Leu Tyr Lys Tyr Arg Asp Gly Phe Ser
    530                 535                 540

Val Ala Asn Tyr Glu Ile Lys Asn Leu Val Met Thr Thr Val Ile Glu
545                 550                 555                 560

Pro Val Pro Leu
```

<210> SEQ ID NO 30
<211> LENGTH: 556
<212> TYPE: PRT
<213> ORGANISM: Pinus torreyana

<400> SEQUENCE: 30

```
Asn Leu Trp Asp Asp Asp Leu Ile Gln Ser Leu Ser Thr Pro Tyr Gly
 1               5                  10                  15

Ala Ile Ser Tyr His Glu Ser Ala Gln Lys Leu Ile Gly Glu Val Lys
            20                  25                  30

Glu Met Ile Asn Ser Ile Ser Val Lys Asp Gly Glu Leu Ile Thr Pro
        35                  40                  45

Ser Asn Asp Leu Leu Met Arg Leu Ser Ile Val Asp Ser Ile Glu Arg
    50                  55                  60

Leu Gly Ile Asp Arg His Phe Lys Ser Glu Ile Lys Ser Ala Leu Asp
65                  70                  75                  80

Tyr Val Tyr Ser Tyr Trp Asn Glu Lys Gly Ile Gly Trp Gly Arg Asp
                85                  90                  95

Ser Val Val Ala Asp Leu Asn Ser Thr Ala Leu Gly Leu Arg Thr Leu
            100                 105                 110

Arg Leu His Gly Tyr Pro Val Ser Ser Asp Val Leu Gln His Phe Lys
        115                 120                 125

Glu Gln Lys Gly Gln Phe Ala Cys Ser Ala Ile Gln Thr Glu Gly Glu
    130                 135                 140

Ile Arg Ser Val Leu Asn Leu Phe Arg Ala Ser Gln Ile Ala Phe Pro
145                 150                 155                 160

Gly Glu Lys Val Met Glu Glu Ala Glu Val Phe Ser Thr Met Tyr Leu
                165                 170                 175

Lys Glu Ala Ile Leu Lys Leu Pro Val Cys Gly Leu Ser Arg Glu Ile
            180                 185                 190

Ser Tyr Val Leu Glu Tyr Gly Trp His Ile Asn Leu Pro Arg Leu Glu
        195                 200                 205

Ala Arg Asn Tyr Ile Asp Val Phe Gly Gln Asp Pro Ile Tyr Leu Thr
    210                 215                 220

Pro Asn Met Lys Thr Gln Lys Leu Leu Glu Leu Ala Lys Leu Glu Phe
225                 230                 235                 240

Asn Met Phe His Ser Leu Gln Gln Gln Glu Leu Lys Leu Leu Ser Arg
                245                 250                 255

Trp Trp Lys Asp Ser Gly Phe Ser Gln Met Thr Phe Pro Arg His Arg
            260                 265                 270

His Val Glu Tyr Tyr Thr Leu Ala Ser Cys Ile Asp Ser Glu Pro Gln
        275                 280                 285

His Ser Ser Phe Arg Leu Gly Phe Ala Lys Ile Phe His Leu Ala Thr
    290                 295                 300

Val Leu Asp Asp Ile Tyr Asp Thr Phe Gly Thr Met Asp Glu Leu Glu
305                 310                 315                 320

Leu Phe Thr Ala Ala Val Lys Arg Trp His Pro Ser Ala Thr Glu Trp
                325                 330                 335

Leu Pro Glu Tyr Met Lys Gly Val Tyr Met Val Leu Tyr Glu Thr Val
            340                 345                 350

Asn Glu Met Ala Gly Glu Ala Glu Lys Ser Gln Gly Arg Asp Thr Leu
        355                 360                 365

Asn Tyr Ala Arg Asn Ala Leu Glu Ala Tyr Ile Asp Ala Ser Met Glu
    370                 375                 380
```

```
Glu Ala Lys Trp Ile Phe Ser Gly Phe Leu Pro Thr Phe Glu Glu Tyr
385                 390                 395                 400

Leu Asp Asn Gly Lys Val Ser Phe Gly Tyr Gly Ile Gly Thr Leu Gln
                405                 410                 415

Pro Ile Leu Thr Leu Gly Ile Pro Phe Pro His His Ile Leu Gln Glu
            420                 425                 430

Ile Asp Phe Pro Ser Arg Leu Asn Asp Val Ala Ser Ser Ile Leu Arg
        435                 440                 445

Leu Lys Gly Asp Ile His Thr Tyr Gln Ala Glu Arg Ser Arg Gly Glu
    450                 455                 460

Lys Ser Ser Cys Ile Ser Cys Tyr Met Glu Glu Asn Pro Glu Ser Thr
465                 470                 475                 480

Glu Glu Asp Ala Ile Asn His Ile Asn Ser Met Val Asp Lys Leu Leu
                485                 490                 495

Lys Glu Leu Asn Trp Glu Tyr Leu Arg Pro Asp Ser Asn Val Pro Ile
            500                 505                 510

Thr Ser Lys Lys His Ala Phe Asp Ile Leu Arg Ala Phe Tyr His Leu
        515                 520                 525

Tyr Lys Tyr Arg Asp Gly Phe Ser Val Ala Asn Tyr Glu Ile Lys Asn
    530                 535                 540

Leu Val Met Thr Thr Val Ile Glu Pro Val Pro Leu
545                 550                 555


<210> SEQ ID NO 31
<211> LENGTH: 564
<212> TYPE: PRT
<213> ORGANISM: Pinus attenuata

<400> SEQUENCE: 31

Arg Arg Arg Gly Asp Phe His Ser Asn Leu Trp Asp Asp Asn Phe Ile
 1               5                  10                  15

Gln Ser Leu Ser Thr Pro Tyr Gly Ala Ile Ser Tyr His Glu Ser Ala
            20                  25                  30

Gln Lys Leu Ile Gly Glu Val Lys Glu Met Ile Asn Ser Ile Ser Asp
        35                  40                  45

Lys Asp Gly Glu Leu Ile Thr Pro Ser Asn Asp Leu Leu Met Leu Leu
    50                  55                  60

Ser Ile Val Asp Ser Ile Glu Arg Leu Gly Ile Asp Arg His Phe Lys
65                  70                  75                  80

Ser Glu Ile Lys Ser Ala Leu Asp Tyr Val Tyr Ser Tyr Trp Asn Glu
                85                  90                  95

Lys Gly Ile Gly Trp Gly Arg Asp Ser Val Val Ala Asp Leu Asn Ser
            100                 105                 110

Thr Ala Leu Gly Leu Arg Thr Leu Arg Leu His Gly Tyr Pro Val Ser
        115                 120                 125

Ser Asp Val Leu Gln His Phe Lys Glu Gln Asn Gly Gln Phe Ala Cys
    130                 135                 140

Ser Ala Ile Gln Thr Glu Gly Glu Ile Arg Ser Val Leu Asn Leu Phe
145                 150                 155                 160

Arg Ala Ser Gln Ile Ala Phe Pro Gly Glu Lys Val Met Glu Glu Ala
                165                 170                 175

Glu Val Phe Ser Thr Lys Tyr Leu Lys Glu Ala Ile Leu Lys Leu Pro
            180                 185                 190

Val Cys Gly Leu Ser Arg Glu Ile Ser Tyr Val Leu Glu Tyr Gly Trp
```

```
        195                 200                 205

His Met Asn Leu Pro Arg Leu Glu Ala Arg Asn Tyr Ile Asp Val Phe
    210                 215                 220

Gly Gln Asp Pro Ile Tyr Leu Thr Pro Asn Met Lys Thr Gln Lys Leu
225                 230                 235                 240

Leu Glu Leu Ala Lys Leu Glu Phe Asn Met Phe His Ser Leu Gln Gln
                245                 250                 255

Gln Glu Leu Lys Leu Leu Ser Arg Trp Trp Lys Asp Ser Gly Phe Ser
            260                 265                 270

Gln Met Thr Phe Pro Arg His Arg His Val Glu Tyr Tyr Thr Leu Ala
        275                 280                 285

Ser Cys Ile Asp Ser Glu Pro Gln His Ser Ser Phe Arg Leu Gly Phe
    290                 295                 300

Ala Lys Ile Phe His Leu Ala Thr Val Leu Asp Asp Ile Tyr Asp Thr
305                 310                 315                 320

Phe Gly Thr Met Asp Glu Leu Glu Leu Phe Thr Ala Ala Val Lys Arg
                325                 330                 335

Trp His Pro Ser Ala Thr Glu Trp Leu Pro Glu Tyr Met Lys Gly Val
            340                 345                 350

Tyr Met Val Leu Tyr Glu Thr Val Asn Glu Met Ala Gly Glu Ala Glu
        355                 360                 365

Lys Ser Gln Gly Arg Asp Thr Leu Asn Tyr Ala Arg Asn Ala Leu Glu
    370                 375                 380

Ala Tyr Ile Asp Ala Ser Met Glu Glu Ala Lys Trp Ile Phe Ser Gly
385                 390                 395                 400

Phe Leu Pro Thr Phe Glu Glu Tyr Leu Asp Asn Gly Lys Val Ser Phe
                405                 410                 415

Gly Tyr Thr Ile Gly Thr Leu Gln Pro Ile Leu Thr Leu Gly Ile Pro
            420                 425                 430

Phe Pro His His Ile Leu Gln Glu Ile Asp Phe Pro Ser Arg Leu Asn
        435                 440                 445

Asp Val Ala Cys Ser Ile Leu Arg Leu Lys Gly Asp Val His Thr Tyr
    450                 455                 460

Gln Pro Glu Arg Ser Arg Gly Glu Glu Ser Ser Cys Ile Ser Cys Tyr
465                 470                 475                 480

Ile Glu Glu Asn Pro Glu Ser Thr Glu Glu Asp Ala Ile Asn His Ile
                485                 490                 495

Asn Ser Met Val Asp Lys Leu Leu Lys Glu Leu Asn Trp Glu Tyr Leu
            500                 505                 510

Arg Pro Asp Ser Asn Val Pro Ile Thr Ser Lys Lys His Ala Phe Asp
        515                 520                 525

Ile Leu Arg Ala Leu Tyr His Leu Tyr Lys Tyr Arg Asp Gly Tyr Ser
    530                 535                 540

Val Ala Asn Tyr Glu Ile Lys Asn Leu Val Met Thr Thr Val Ile Glu
545                 550                 555                 560

Pro Val Pro Leu


<210> SEQ ID NO 32
<211> LENGTH: 556
<212> TYPE: PRT
<213> ORGANISM: Pinus radiata

<400> SEQUENCE: 32

Asn Leu Trp Asp Asp Asp Leu Ile Gln Ser Leu Ser Thr Pro Tyr Gly
```

-continued

```
1               5                   10                  15

Ala Ile Ser Tyr His Glu Ser Ala Gln Lys Leu Ile Gly Glu Val Lys
            20                  25                  30

Glu Met Ile Asn Ser Ile Ser Asp Lys Asn Gly Glu Leu Ile Thr Pro
        35                  40                  45

Ser Asn Asp Leu Leu Met Arg Leu Ser Ile Val Asp Ser Ile Glu Arg
    50                  55                  60

Leu Gly Ile Asp Arg His Phe Lys Ser Glu Ile Lys Ser Ala Leu Asp
65                  70                  75                  80

Tyr Val Tyr Ser Tyr Trp Asn Glu Lys Gly Ile Gly Trp Gly Arg Asp
                85                  90                  95

Ser Val Val Ala Asp Leu Asn Ser Thr Ala Leu Gly Leu Arg Thr Leu
            100                 105                 110

Arg Leu His Gly Tyr Pro Val Ser Ser Asp Val Leu Gln His Phe Lys
        115                 120                 125

Glu Gln Asn Gly Gln Phe Ala Cys Ser Ala Ile Gln Thr Glu Gly Glu
    130                 135                 140

Ile Arg Ser Val Leu Asn Leu Phe Arg Ala Ser Gln Ile Ala Phe Pro
145                 150                 155                 160

Gly Glu Lys Val Met Glu Glu Ala Glu Val Phe Ser Thr Lys Tyr Leu
                165                 170                 175

Lys Glu Ala Ile Leu Lys Leu Pro Val Cys Gly Leu Ser Arg Glu Ile
            180                 185                 190

Ser Tyr Val Leu Glu Tyr Gly Trp His Met Asn Leu Pro Arg Leu Glu
        195                 200                 205

Ala Arg Asn Tyr Ile Asp Val Phe Gly Gln Asp Pro Ile Tyr Leu Thr
    210                 215                 220

Pro Asn Met Lys Thr Gln Lys Leu Leu Glu Leu Ala Lys Leu Glu Phe
225                 230                 235                 240

Asn Met Phe His Ser Leu Gln Gln Gln Glu Leu Lys Leu Leu Ser Arg
                245                 250                 255

Trp Trp Lys Asp Ser Gly Phe Ser Gln Met Thr Phe Pro Arg His Arg
            260                 265                 270

His Val Glu Tyr Tyr Thr Leu Ala Ser Cys Ile Asp Ser Glu Pro Gln
        275                 280                 285

His Ser Ser Phe Arg Leu Gly Phe Ala Lys Ile Phe His Leu Ala Thr
    290                 295                 300

Val Leu Asp Asp Ile Tyr Asp Thr Phe Gly Thr Met Asp Glu Leu Glu
305                 310                 315                 320

Leu Phe Thr Ala Ala Val Lys Arg Trp His Pro Ser Ala Thr Glu Trp
                325                 330                 335

Leu Pro Glu Tyr Met Lys Gly Val Tyr Met Val Leu Tyr Glu Thr Val
            340                 345                 350

Asn Glu Met Ala Gly Glu Ala Glu Lys Ser Gln Gly Arg Asp Thr Leu
        355                 360                 365

Asn Tyr Ala Arg Asn Ala Leu Glu Ala Tyr Ile Asp Ala Ser Met Glu
    370                 375                 380

Glu Ala Lys Trp Ile Phe Ser Gly Phe Leu Pro Thr Phe Glu Glu Tyr
385                 390                 395                 400

Leu Asp Asn Gly Lys Val Ser Phe Gly Tyr Thr Ile Gly Thr Leu Gln
                405                 410                 415

Pro Ile Leu Thr Leu Gly Ile Pro Phe Pro His His Ile Leu Gln Glu
            420                 425                 430
```

```
Ile Asp Phe Pro Ser Arg Leu Asn Asp Val Ala Cys Ser Ile Leu Arg
        435                 440                 445

Leu Lys Gly Asp Val His Thr Tyr Gln Pro Glu Arg Ser Arg Gly Glu
    450                 455                 460

Glu Ser Ser Cys Ile Ser Cys Tyr Met Glu Glu Asn Pro Glu Ser Thr
465                 470                 475                 480

Glu Glu Asp Ala Ile Asn His Ile Asn Ser Met Val Asp Lys Leu Leu
                485                 490                 495

Lys Glu Leu Asn Trp Glu Tyr Leu Arg Pro Asp Ser Asn Val Pro Ile
            500                 505                 510

Thr Ser Lys Lys His Ala Phe Asp Ile Leu Arg Ala Leu Tyr His Leu
        515                 520                 525

Tyr Lys Tyr Arg Asp Gly Tyr Ser Val Ala Asn Tyr Glu Ile Lys Asn
    530                 535                 540

Leu Val Met Thr Thr Val Ile Glu Pro Val Pro Leu
545                 550                 555


<210> SEQ ID NO 33
<211> LENGTH: 593
<212> TYPE: PRT
<213> ORGANISM: Pinus contorta

<400> SEQUENCE: 33

Ser Ser Lys Val Lys Val Val Arg Arg Thr Met Ser Thr Ser Ile Arg
 1               5                  10                  15

Met Cys Gln Ile Thr Thr Val Ser Gly Glu Gly Val Gln Arg Arg Ile
            20                  25                  30

Ala Asn His His Ser Asn Leu Trp Asp Asp Asn Phe Ile Gln Ser Leu
        35                  40                  45

Ser Thr Pro Tyr Gly Ala Ile Ser Tyr His Glu Ser Ala Gln Lys Leu
    50                  55                  60

Ile Gly Glu Val Lys Glu Met Ile Asn Ser Ile Ser Val Lys Asp Gly
65                  70                  75                  80

Glu Leu Ile Thr Pro Ser Asn Asp Leu Leu Met Arg Leu Ser Ile Val
                85                  90                  95

Asp Ser Ile Glu Arg Leu Gly Ile Asp Arg His Phe Lys Ser Glu Ile
            100                 105                 110

Lys Ser Ala Leu Asp Tyr Val Tyr Ser Tyr Trp Asn Glu Lys Gly Ile
        115                 120                 125

Gly Trp Gly Arg Asp Ser Val Val Ala Asp Leu Asn Ser Thr Ala Leu
    130                 135                 140

Gly Leu Arg Thr Leu Arg Leu His Gly Tyr Pro Val Ser Ser Asp Val
145                 150                 155                 160

Leu Gln His Phe Lys Glu Gln Lys Gly Gln Phe Ala Cys Ser Ala Ile
                165                 170                 175

Gln Thr Glu Gly Glu Ile Arg Ser Val Leu Asn Leu Phe Arg Ala Ser
            180                 185                 190

Gln Ile Ala Phe Pro Gly Glu Lys Val Met Glu Glu Ala Glu Val Phe
        195                 200                 205

Ser Thr Lys Tyr Leu Lys Glu Ala Ile Leu Lys Leu Pro Val Cys Gly
    210                 215                 220

Leu Ser Arg Glu Ile Ser Tyr Val Leu Glu Tyr Gly Trp His Met Asn
225                 230                 235                 240

Leu Pro Arg Leu Glu Ala Arg Asn Tyr Ile Asp Val Phe Gly Gln Asp
```

```
                245                 250                 255

Pro Ile Tyr Leu Thr Pro Asn Met Lys Thr Gln Lys Leu Leu Glu Leu
            260                 265                 270

Ala Lys Leu Glu Phe Asn Met Phe His Ser Leu Gln Gln Gln Glu Leu
        275                 280                 285

Lys Leu Leu Ser Arg Trp Trp Lys Asp Ser Gly Phe Ser Gln Met Thr
    290                 295                 300

Phe Pro Arg His Arg His Val Glu Tyr Tyr Thr Leu Ala Ser Cys Ile
305                 310                 315                 320

Asp Ser Glu Pro Gln His Ser Ser Phe Arg Leu Gly Phe Ala Lys Ile
                325                 330                 335

Phe His Leu Ala Thr Val Leu Asp Asp Ile Tyr Asp Thr Phe Gly Thr
            340                 345                 350

Met Asp Glu Leu Glu Leu Phe Thr Ala Ala Val Lys Arg Trp His Pro
        355                 360                 365

Ser Ala Thr Glu Trp Leu Pro Glu Tyr Met Lys Gly Val Tyr Met Val
    370                 375                 380

Leu Tyr Glu Thr Val Asn Glu Met Ala Gly Glu Ala Glu Lys Ser Gln
385                 390                 395                 400

Gly Arg Asp Thr Leu Asn Tyr Ala Arg Asn Ala Leu Glu Ala Tyr Ile
                405                 410                 415

Asp Ala Ser Met Glu Glu Ala Lys Trp Ile Phe Ser Gly Phe Leu Pro
            420                 425                 430

Thr Phe Glu Glu Tyr Leu Asp Asn Gly Lys Val Ser Phe Gly Tyr Thr
        435                 440                 445

Ile Gly Thr Leu Gln Pro Ile Leu Thr Leu Gly Ile Pro Phe Pro His
    450                 455                 460

His Ile Leu Gln Glu Ile Asp Phe Pro Ser Arg Leu Asn Asp Val Ala
465                 470                 475                 480

Cys Ser Ile Leu Arg Leu Lys Gly Asp Ile His Thr Tyr Gln Pro Glu
                485                 490                 495

Arg Ser Arg Gly Glu Glu Ser Ser Cys Ile Ser Cys Tyr Met Glu Asp
            500                 505                 510

Asn Pro Glu Ser Thr Glu Glu Asp Ala Ile Asn His Ile Asn Ser Met
        515                 520                 525

Val Asp Lys Leu Leu Lys Glu Leu Asn Trp Glu Tyr Leu Arg Pro Asp
    530                 535                 540

Ser Asn Val Pro Ile Thr Ser Lys Lys His Ala Phe Asp Ile Leu Arg
545                 550                 555                 560

Ala Phe Tyr His Leu Tyr Lys Tyr Arg Asp Gly Tyr Ser Val Ala Asn
                565                 570                 575

Tyr Glu Ile Lys Asn Leu Val Met Thr Thr Val Ile Glu Pro Val Pro
            580                 585                 590

Leu


<210> SEQ ID NO 34
<211> LENGTH: 593
<212> TYPE: PRT
<213> ORGANISM: Pinus contorta

<400> SEQUENCE: 34

Ser Ser Lys Val Lys Val Val Arg Arg Thr Met Ser Thr Ser Ile Arg
 1               5                  10                  15

Met Cys Gln Ile Thr Thr Val Ser Gly Glu Gly Val Gln Arg Arg Ile
```

```
            20                  25                  30

Ala Asn His His Ser Asn Leu Trp Asp Asp Asn Phe Ile Gln Ser Leu
        35                  40                  45

Ser Thr Pro Tyr Gly Ala Ile Ser Tyr His Glu Ser Ala Gln Lys Leu
    50                  55                  60

Ile Gly Glu Val Lys Glu Met Ile Asn Ser Ile Ser Val Lys Asp Gly
65                  70                  75                  80

Glu Leu Ile Thr Pro Ser Asn Asp Leu Leu Met Arg Leu Ser Ile Val
                85                  90                  95

Asp Ser Ile Glu Arg Leu Gly Ile Asp Arg His Phe Lys Ser Glu Ile
            100                 105                 110

Lys Ser Ala Leu Asp Tyr Val Tyr Ser Tyr Trp Asn Glu Lys Gly Ile
        115                 120                 125

Gly Trp Gly Arg Asp Ser Val Val Ala Asp Leu Asn Ser Thr Ala Leu
    130                 135                 140

Gly Leu Arg Thr Leu Arg Leu His Gly Tyr Pro Val Ser Ser Asp Val
145                 150                 155                 160

Leu Gln His Phe Lys Glu Gln Lys Gly Gln Phe Ala Cys Ser Ala Ile
                165                 170                 175

Gln Thr Glu Gly Glu Ile Arg Ser Val Leu Asn Leu Phe Arg Ala Ser
            180                 185                 190

Gln Ile Ala Phe Pro Gly Glu Lys Val Met Glu Glu Ala Glu Val Phe
        195                 200                 205

Ser Thr Lys Tyr Leu Lys Glu Ala Ile Leu Lys Leu Pro Val Cys Gly
    210                 215                 220

Leu Ser Arg Glu Ile Ser Tyr Val Leu Glu Tyr Gly Trp His Ile Asn
225                 230                 235                 240

Leu Pro Arg Leu Glu Ala Arg Asn Tyr Ile Asp Val Phe Gly Gln Asp
                245                 250                 255

Pro Ile Tyr Leu Thr Pro Asn Met Lys Thr Gln Lys Leu Leu Glu Leu
            260                 265                 270

Ala Lys Leu Glu Phe Asn Met Phe His Ser Leu Gln Gln Gln Glu Leu
        275                 280                 285

Lys Leu Leu Ser Arg Trp Trp Lys Asp Ser Gly Phe Ser Gln Met Thr
    290                 295                 300

Phe Pro Arg His Arg His Val Glu Tyr Tyr Thr Leu Ala Ser Cys Ile
305                 310                 315                 320

Asp Ser Glu Pro Gln His Ser Ser Phe Arg Leu Gly Phe Ala Lys Ile
                325                 330                 335

Phe His Leu Ala Thr Val Leu Asp Asp Ile Tyr Asp Thr Phe Gly Thr
            340                 345                 350

Met Asp Glu Leu Glu Leu Phe Thr Ala Ala Val Lys Arg Trp His Pro
        355                 360                 365

Ser Ala Thr Glu Trp Leu Pro Glu Tyr Met Lys Gly Val Tyr Met Val
    370                 375                 380

Leu Tyr Glu Thr Val Asn Glu Met Ala Gly Glu Ala Glu Lys Ser Gln
385                 390                 395                 400

Gly Arg Asp Thr Leu Asn Tyr Ala Arg Asn Ala Leu Glu Ala Tyr Ile
                405                 410                 415

Asp Ala Ser Met Glu Glu Ala Lys Trp Ile Phe Ser Gly Phe Leu Pro
            420                 425                 430

Thr Phe Glu Glu Tyr Leu Asp Asn Gly Lys Val Ser Phe Gly Tyr Thr
        435                 440                 445
```

```
Ile Gly Thr Leu Gln Pro Ile Leu Thr Leu Gly Ile Pro Phe Pro His
    450                 455                 460

His Ile Leu Gln Glu Ile Asp Phe Pro Ser Arg Leu Asn Asp Val Ala
465                 470                 475                 480

Cys Ser Ile Leu Arg Leu Lys Gly Asp Val His Thr Tyr Gln Ala Glu
                485                 490                 495

Arg Ser Arg Gly Glu Glu Ser Ser Cys Ile Ser Cys Tyr Met Glu Asp
            500                 505                 510

Asn Pro Glu Ser Thr Glu Glu Asp Ala Ile Asn His Ile Asn Ser Met
        515                 520                 525

Val Asp Lys Leu Leu Lys Glu Leu Asn Trp Glu Tyr Leu Arg Pro Asp
    530                 535                 540

Ser Asn Val Pro Ile Thr Ser Lys Lys His Ala Phe Asp Ile Leu Arg
545                 550                 555                 560

Ala Phe Tyr His Leu Tyr Lys Tyr Arg Asp Gly Tyr Ser Val Ala Asn
                565                 570                 575

Tyr Glu Ile Lys Asn Leu Val Met Thr Thr Val Ile Glu Pro Val Pro
            580                 585                 590

Leu
```

METHYL BUTENOL SYNTHASE

RELATED APPLICATION

This application is a divisional of and claims the benefit of priority under 35 U.S.C. § 120 to U.S. patent application Ser. No. 15/058,746, filed Mar. 2, 2016, which is a divisional of U.S. patent application Ser. No. 14/174,694, filed on Feb. 6, 2014, which is a divisional of Ser. No. 13/321,458, filed on Mar. 5, 2012, which is a U.S. National Stage Filing under 35 U.S.C. 371 from International Application No. PCT/US2010/035820, filed May 21, 2010 and published in English as WO 2010/135674 on Nov. 25, 2010, and claims priority from U.S. Provisional Application Ser. No. 61/180,757 filed May 22, 2009, which applications are herein incorporated by reference in their entireties.

STATEMENT OF GOVERNMENT RIGHTS

This invention was made with government support under Grant number IOS0830225 awarded by the National Science Foundation. The government has certain rights in the invention.

BACKGROUND OF THE INVENTION

In 2007, there were 1.8 million alternative fuel vehicles sold in the United States, indicating an increasing popularity of alternative fuels. There is growing perceived economic and political need for the development of alternative fuel sources due to general environmental, economic, and geopolitical concerns of sustainability.

The major environmental concern is that most of the observed increase in globally averaged temperatures since the mid-20th century is due to the observed increase in greenhouse gas concentrations. Since burning fossil fuels is known to increase greenhouse gas concentrations in the atmosphere, it is believed that they are a likely contributor to global warming.

Although fossil fuels have become the dominant energy resource for the modern world, alcohol has been used as a fuel throughout history. The first four aliphatic alcohols (methanol, ethanol, propanol, and butanol) are of interest as fuels because they can be synthesized and they have characteristics which allow them to be used in current engines. Biobutanol has an energy density that is closer to gasoline than the other alcohols; however, this advantage is outweighed by disadvantages (compared to ethanol and methanol) concerning, for example, production.

SUMMARY OF THE INVENTION

The present invention provides for the first time genes encoding methyl butenol (MBO) synthase and its use in methyl butenol production. Thus, one embodiment provides an isolated and purified methyl butenol (MBO) synthase nucleic acid molecule, wherein the MBO synthase nucleic acid molecule comprises any one of SEQ ID NOs:1-17 or a nucleic acid molecule having at least about 80% sequence identity thereof.

Another embodiment provides an expression vector comprising a MBO synthase nucleic acid molecule. One embodiment provides a prokaryotic or eukaryotic host cell transformed with a MBO synthase nucleic acid molecule (e.g., in an expression vector). In one embodiment the transformed host cells express the exogenous MBO synthase (mRNA or protein). In one embodiment, the host cells express MBO synthase and yield MBO.

One embodiment provides an isolated and purified methyl butenol (MBO) synthase polypeptide, wherein the MBO synthase polypeptide comprises any one of SEQ ID NOs: 18-34 or a bioactive polypeptide having at least about 80% sequence identity thereof.

Another embodiment provides a method to produce methyl butenol comprising transforming a host cell with a nucleic acid molecule coding for a methyl butenol synthase and expressing said molecule in a host cell so as to yield methyl butenol. In one embodiment, the hose cells are fermentative organisms, such as a bacteria, cyanobacteria or yeast (e.g., a bacteria or yeast that can break down sugar into alcohol) or eukaryotic micro algae. In one embodiment the fermentative organism is *Saccharomyces cerevisiae, Klebsiella oxytoca, Synechococcus* sp., *Synechocystis* sp., *Anabaena* sp., *Chlorella* sp. *Scenedesmus* sp., *Bracteococcus* sp. *Chlamydomonus* sp., C5- or C6-fermentative organisms (including *Zymomonas* (e.g., *Zymomonas mobilis*)) or a combination thereof. In one embodiment, the transformed host cell is used in fermentation with a carbohydrate to yield MBO (similar to bioethanol production).

In one embodiment, the MBO synthase (in a purified or unpurified form) is used in combination with a carbohydrate to yield MBO. In one embodiment, the fermentative organism is bacteria, cyanobacteria or yeast (e.g., a bacteria or yeast that can break down sugar into alcohol) or eukaryotic micro algae. In one embodiment the fermentative organism is *Saccharomyces cerevisiae, Klebsiella oxytoca, Synechococcus* sp., *Synechocystis* sp., *Anabaena* sp., *Chlorella* sp. *Scenedesmus* sp., *Bracteococcus* sp. *Chlamydomonus* sp., C5- or C6-fermentative organisms (including *Zymomonas* (e.g., *Zymomonas mobilis*)) or combinations thereof.

BRIEF DESCRIPTION OF THE DRAWINGS

FIGS. 1A-M provide nucleic acid molecules coding for a methyl butenol synthase (SEQ ID NOs:1-17).

FIGS. 2A-E provide the sequence of several methyl butenol synthases. (SEQ ID NO:18-34).

DETAILED DESCRIPTION OF THE INVENTION

Figure 3A:
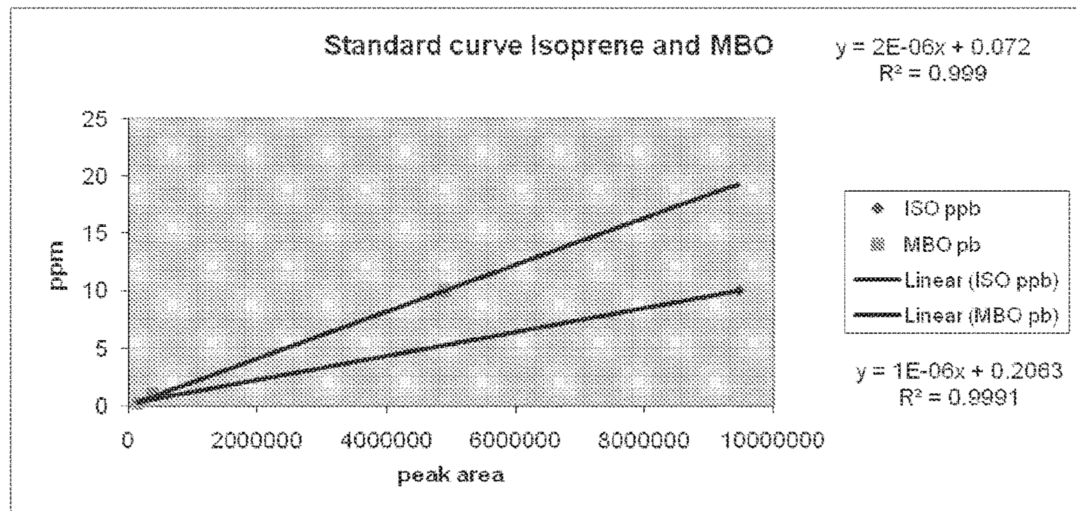
FIGS. 3A-B demonstrate the methylbutenol and isoprene production from soluble and insoluble extract fractions.

The present invention provides for the first time genes encoding methyl butenol (MBO) synthase and its use in methyl butenol production. In particular, the methyl butenol synthase gene was isolated from several species of pine. The gene is useful for the enzymatic production of methyl butenol, which can be used as an alternative fuel (e.g., a biofuel or gasoline replacement). Thus, the methods provided herein provide a practical, non-polluting technology for producing methyl butenol using methyl butenol synthase proteins and genes. Exemplary cDNA sequences coding for methyl butenol synthases are provided in SEQ ID NOs:1-17, while exemplary amino acids sequences are provided in SEQ ID NOs:18-34 (see FIGS. 1 and 2).

Definitions

Certain terms used in the specification are defined and presented as follows:

2-methyl-3-buten-2-ol (molecular formula of $C_5H_{10}O$; also known as methyl butenol or methylbutenol (MBO)) is a natural 5-carbon alcohol that is produced and emitted from the foliage by several species of pine, e.g., species in the genus *Pinus,* with the following structure

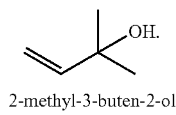

2-methyl-3-buten-2-ol

Biosynthesis of MBO occurs in the chloroplast through the action of the enzyme MBO synthase, which uses DMADP derived from the MEP pathway as a substrate.

"Associated with/operably linked" refers to two DNA sequences that are related physically or functionally. For example, a promoter or regulatory DNA sequence is said to be "associated with" a DNA sequence that codes for an RNA or a protein if the two sequences are operably linked, or situated such that the regulator DNA sequence will affect the expression level of the coding or structural DNA sequence.

"Coding DNA sequence:" refers to a DNA sequence that is translated in an organism to produce a protein. "Expression" of a sequence includes the production of mRNA and/or protein.

"Isolated," in the context of the present invention, an isolated nucleic acid molecule or an isolated polypeptide is a nucleic acid molecule or polypeptide that, by the hand of man, exists apart from its native environment and is therefore not a product of nature. Thus, the term isolated refers to a molecule (e.g., nucleic acid or protein) which is not associated with one or more nucleic acid molecules, proteins or one or more cellular components that are associated with the nucleic acid molecule or protein in vivo. An isolated nucleic acid molecule or an isolated protein may exist in a purified form (e.g., ranges of purity in samples comprising isolated nucleic acid molecules or an isolated protein are 50-55%, 55-60%, 60-65% and 60-70%; ranges of purity also include 70-75%, 75-80%, 80-85%; 85-90%, 90-95%, and 95-100%; however, samples with lower purity can also be useful, such as about <25%, 25-30%, 30-35%, 35-40%, 40-45% and 45-50%.) or may exist in a non-native environment such as, for example, a transgenic host cell.

A "cell" or "host cell" is a prokaryotic or eukaryotic cell.

Alternative fuels, also known as non-conventional fuels, are any materials or substances that can be used as fuels, other than conventional fuels. Conventional fuels include: fossil fuels (petroleum (oil), coal, propane, and natural gas), and nuclear materials such as uranium. Some well known alternative fuels include biodiesel, bioalcohol (methanol, ethanol, butanol), chemically stored electricity (batteries and fuel cells), hydrogen, non-fossil methane, non-fossil natural gas, vegetable oil and other biomass sources. For example, one alternative is alcohol fuel.

Alcohol fuels are usually of biological ather than petroleum sources. When obtained from biological sources, they are known as bioalcohols (e.g. bioethanol). As described herein 2-methyl-3-butene-2-ol (methyl butenol) can be manufactured in organisms carrying a synthase gene of the invention or by fermentative organisms in contact with a synthase protein of the invention and a carbohydrate source. It is a sustainable energy resource that can provide a more environmentally and economically friendly alternative to fossil fuels such as diesel and gasoline. It can be combined with gasoline at different percentages, or can be used in its pure form. Generally, methyl butanol is more advantageous than ethanol as a fuel due to its increased density and relatively little or no water absorption as with ethanol. Unlike butanol, the presence of a branched carbon chain increases its octane rating and the presence of a double carbon-carbon bond can reduce toxicity.

The terms "comprises," "comprising," and the like can have the meaning ascribed to them in U.S. Patent Law and can mean "includes," "including" and the like. As used herein, "including" or "includes" or the like means including, without limitation.

Methyl Butenol Synthase Genes/Proteins

Provided herein are methyl butenol synthase genes including those of SEQ ID NOs: 1-17 or a nucleic acid molecule which comprises a sequence that has at least about 50%, at least about 60%, at least about 70%, about 71%, about 72%, about 73%, about 74%, about 75%, about 76%, about 77%, about 78%, or about 79%, or at least about 80%, about 81%, about 82%, about 83%, about 84%, about 85%, about 86%, about 87%, about 88%, or about 89%, or at least about 90%, about 91%, about 92%, about 93%, or about 94%, or at least about 95%, about 96%, about 97%, about 98%, about 99%, or about 100% sequence identity compared to any one of SEQ ID NOs:1-17 using one of the alignment programs available in the art using standard parameters.

Also provided herein are methyl butenol synthase proteins including those of SEQ ID NOs:18-34 or a polypeptide which comprises a sequence that has at least about 50%, at least about 60%, at least about 70%, about 71%, about 72%, about 73%, about 74%, about 75%, about 76%, about 77%, about 78%, or about 79%, or at least about 80%, about 81%, about 82%, about 83%, about 84%, about 85%, about 86%, about 87%, about 88%, or about 89%, or at least about 90%, about 91%, about 92%, about 93%, or about 94%, or at least about 95%, about 96%, about 97%, about 98%, about 99%, or about 100% sequence identity compared to any one of SEQ ID NOs:18-34 using one of the alignment programs available in the art using standard parameters. In one embodiment, the differences in sequence are due to conservative amino acid changes. In one erribodiment, the functional properties of the enzyme are improved through the useof molecular evolution and design studies.

Methods of alignment of sequences for comparison are available in the art. Thus, the determination of percent identity between any two sequences can be accomplished using a mathematical algorithm. Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Expression of Methyl Butenol Synthase and Production of Methyl Butenol (MBO)

Methyl butenol synthase can be introduced into any number of organisms to cause them to produce methyl butenol synthase and/or methyl butenol. For example, the genes can be cloned into appropriate expression vectors and expressed in bacteria or yeast. The creation of expression vectors comprising the nucleic acid molecules of the invention and bacterial and yeast transformation techniques are described in detail in the literature and available to an art worker. Typically an expression. vector contains (1) prokaryotic DNA elements coding for a bacterial replication origin and an antibiotic resistance gene to provide for the amplification and selection of the expression vector in a bacterial host or DNA elements to allow expression in a eukaryotic host cell (e.g., yeast); (2) regulatory elements that control initiation of transcription such as a promoter; and (3) DNA elements that control the processing of transcripts such as introns, transcription termination/polyadenylation sequence.

Methods to introduce a nucleic acid molecule into a vector are well known in the art (Sambrook et al., 1989). As an example, a vector into which the nucleic acid segment is to be inserted is treated with one or more restriction enzymes (restriction endonuclease) to produce a linearized vector having a blunt end, a "sticky" end with a 5' or a 3' overhang, or any combination thereof. The vector may also be treated with a restriction enzyme and subsequently treated with another modifying enzyme, such as a polymerase, an exonuclease, a phosphatase or a kinase, to create a linearized vector that has characteristics useful for ligation of a nucleic acid molecule into the vector. The nucleic acid molecule that is to be inserted into the vector is treated with one or more restriction enzymes to create a linearized segment having a blunt end, a "sticky" end with a 5' or a 3' overhang, or any combination thereof. The nucleic acid molecule may also be treated with a restriction enzyme and subsequently treated with another DNA modifying enzyme. Such DNA modifying enzymes include, but are not limited to, polymerase, exonuclease, phosphatase or a kinase, to create a polynucleic acid segment that has characteristics useful for ligation of a nucleic acid molecule into the vector.

The treated vector and nucleic acid molecule are then ligated together to form a construct containing a nucleic acid segment according to methods known in the art (Sambrook, 2002). Briefly, the treated nucleic acid molecule and the treated vector are combined in the presence of a suitable buffer and ligase. The mixture is then incubated under appropriate conditions to allow the ligase to ligate the nucleic acid molecule into the vector.

An example of the preparation of an expression vector and expression of MBO synthase in an organism is described in the examples below. However, any expression vector and organism combination for expression available to an art worker may be acceptable for use in the methods of the invention. It will be clear to one of ordinary skill in the art which vector should be used depending on which cell type is used for a host cell.

Alternatively, the methyl butenol synthases of the invention can also be chemically synthesized through peptide synthesis procedures available to the art. The free enzyme can be contacted with an appropriate substrate (a source of carbohydrate) to produced methyl butenol (with our without the use of a host cell).

After preparation of the expression vector and introduction into an appropriate host cell, the cells can be grown in culture to produce methyl butenol synthase and/or methyl butenol, which can be collected (and optionally distilled or condensed).

Alternatively, the culture can be used to produce the free enzyme which is then used to produce MBO. For example, a source of carbohydrate (e.g., sugars (e.g., $C_nH_{2n}O_n$ (n is between 3 and 7), including a monosaccharide (e.g., glucose, dextrose or fructose) or a disaccharide (e.g., sucrose), starches (e.g., a carbohydrate consisting of a large number of glucose units joined together by glycosidic bonds, such as amylase or amylopectin) and/or cellulose (e.g., an organic compound with the formula $(C_6H_{10}O_5)_n$, a polysaccharide consisting of a linear chain of several hundred to over ten thousand β(1→4) linked D-glucose units)) and a methyl butenol (MBO) synthase of the invention can be combined to yield MBO, which can be purified further (e.g., distilled or condensed from the head space).

The MBO produced by the methods of the invention can be used as an alternative fuel source.

EXAMPLES

The following examples are provided in order to demonstrate and further illustrate certain embodiments and aspects of the present invention and is not to be construed as limiting the scope thereof.

Example 1

Preparation of Methyl Butanol Synthase Vectors and Assay for Activity

Materials and Methods

RNA Extraction

Total RNA was extracted from frozen pine needle tissue from *Pinus sabiniana* using a modified CTAB procedure adapted from (Chang et al. (1993) *Plant Molecular Biology Reporter,* 11(2):113-116.). Needle samples (250 mg) were ground under liquid nitrogen, and extracted for 45 minutes at 70° C. in 800 ul volumes of extraction buffer containing 2% CTAB, 2% PVP-40, 100 mM Tris pH8.0, 25 mM EDTA, 2.0M NaCl, and 0.5 g/L Spermidine with 4% β-mercaptoethanol, 4% PVPP, and an additional 4% PVP40 was added just before use. Following incubation at 70° C. for 45 minutes, samples were extracted twice with 500 μl volumes of 24:1 (v:v) chloroform:isoamyl alcohol solution. RNA was then precipitated by adding ¼ volume of 10M LiCl to the aqueous phase, gently mixing, and storing the mixture overnight at 4° C. Following centrifugation to collect the RNA pellet, the supernatant was discarded and the pellet was re-suspended in 500 μl of SSTE Buffer containing 1.0M NaCl, 0.5% SDS, 10 mM Tris pH8.0, and 1 mM EDTA. This solution was then extracted once with equal volumes of phenol, once with phenol:chloroform:IAA (24:24:1 v/v), and once with chloroform:IAA (24:1 v/v). To precipitate the RNA pellet, 2 volumes of cold (−20° C.) ethanol were added to the supernatant followed by incubation for 2 hours at −20° C. Following centrifugation to collect the pellet, the RNA was air dried, re-suspended in distilled water, and stored at −20 C until further use.

cDNA Synthesis

First strand cDNA synthesis was performed using M-MLV reverse transcriptase obtained from Invitrogen (Carlsbad, Calif.) following the manufacturers instructions. Total RNA (2 μg), and 1 μg oligo-dT(17) primer were denatured by incubation at 70° C. for 5 minutes, and then placed on ice for 5 min to anneal the oligo-dT primer to the mRNA polyA tail. Reagents were added to this mixture to achieve a 50 μL volume containing 1× concentration M-MLV buffer, 0.5 mM dNTPs, 0.1M DTT and 2.5 units of RNasin (Promega, Madison Wis.). The first strand synthesis reactions were performed by incubating for 60 min at 37° C., followed by incubating for 10 min at 42° C., and heat inactivation of the enzyme by incubating at 70° C. for 15 min. Reactions were cooled on ice and stored at −20° C. until further use.

Primer Design.

Initially, degenerate PCR primers were designed to correspond to highly conserved regions of known pine monoterpene synthases. Sequencing of the PCR amplified products revealed 3 distinct sequences which showed high similarity to known pine monoterpene synthases. One sequence contained a phenylalanine residue 7 amino acids upstream of the highly conserved DDXXD motif of terpene synthases. Since this position corresponds to the location of a phenylalanine residue in isoprene synthases and is believed to limit the size of the substrate that can fit into the enzymes active site, this phenylalanine containing sequence was selected for further exploration. To obtain the 5' and 3' ends of this sequence 5' and 3' rapid amplification of cDNA ends (RACE) was employed. For these procedures gene specific forward and reverse primers were designed from the previously selected partial MBO synthase sequence.

PCR Reactions.

Initial PCR reactions were run using 1.25 units of Gotaq DNA polymerase in 30 μl reaction volumes containing 1× Gotaq buffer, 20 μM dNTPs, 1 μM concentrations of each primer, and 0.2 μg template cDNA. In preparation for cloning, full length cDNAs were amplified using either Pfu turbo (Stratagene, La Jolla Calif.) or Platinum Pfx (Invitrogen, Carlsbad Calif.) DNA polymerases according to the manufacturer instructions. To amplify full length cDNAs PCR reactions were run using an initial denaturation of 2 min at 95° C., followed by 35 repetitions of denaturation at 95° C. for 30 sec, annealing at 52° C. for 45 sec, and extension at 72° C. for 3 min, followed by a final extension at 72° C. for 9 min.

Rapid Amplification of cDNA Ends (RACE)

Rapid amplification of cDNA ends (RACE) procedures were employed to amplify the 5' and 3' ends of the partial MBO sequence obtained using degenerate primers. RACE reactions were run using 1.25 units of Gotaq DNA polymerase in 30 μl reaction volumes containing 1× Gotaq buffer, 20 μM dNTPs, 1 μM concentrations of each primer (gene specific, adapter, oligo dt-adapter), and 0.2 μg template cDNA.

Cloning into the Expression Vector

The full length amino acid sequence of the MBO synthase gene contains an N-terminal region similar to the plastid transport sequences found in known conifer monoterpene synthases. These transport sequences have been found to interfere with protein expression in *E. coli* (Williams et al. (1998) *Biochemistry*, (37):12213-12220), hence primers were designed to amplify a fragment of the putative MBO synthase gene lacking this chloroplast transport sequence. Hereafter this will be referred to as an expression length sequence.

Expression length sequences were first ligated into the vector p-GEMT easy (Promega, Madison Wis.) and transformed into the *E. coli* host strain DH5α. pGEMT-easy plasmids containing the MBO synthase gene (pGEMT-MBO) were extracted from the DH5α host and digested with the restriction enzymes SphI and PstI to release an ~1800 bp fragment containing the MBO synthase gene with a 5' SphI and 3' PstI splice site. This fragment was then gel purified and ligated into the expression vector pQE-31 (Qiagen) following digestion of pQE-31 vector with the restriction enzymes SphI and PstI and gel purification of the 3.4 kb digested product. Gel purification of restriction digests was done using a Qiagen gel purification kit (Qiagen). Following ligation of the expression length MBO sequence into the expression vector pQE-31, pQE-31-MBO was transformed into *E. coli* strain BL21-CodonPlus(DE3)-RIL (Stratagene, La Jolla Calif.). This strain of *E. coli* has been modified to correct for codon bias by increasing the expression of several t-RNAs that match codons that are common in plant terpene synthases, but rare in *E. coli.* The MBO synthase gene contains several codons for which t-RNAs in *E. coli* are rare.

Functional Expression and Assay for Methyl Butenol Production.

*E. coli* BL21-Codon Plus(DE3)-RIL containing expression plasmid pQE-31-MBO were grown overnight at 37° C. with shaking at 200 rpm in 5 ml Luri Broth supplemented with 200 μg/ml ampicillin and 34 μg/ml chloramphenicol. Aliquots of bacterial culture (0.5 ml) were placed into 5 ml vials and protein expression induced by adding 0.5 mM IPTG. Vials were capped with a septum and incubated at 30° C. with shaking at 200 rpm for 2 hours before analysis of headspace volatiles by gas chromatography.

To measure methyl butenol in vial headspace, 3 ml aliquots of headspace were withdrawn from the vial and cryofocused by injection into a stainless steel sample loop immersed in liquid nitrogen. The cryofocused sample was then flash vaporized by immersing the sample loop in warm water and flushed onto a widebore capillary DB-1 GC column, 30 m length, 0.32 mm ID, 5 micron film (JW Scientific, Folsom, Calif.) using flow of Helium carrier gas, and analyzed using a Photoionization detector. Component separation was achieved using a temperature program of 30° C. for 10 minutes, followed by a temperature ramp of 2° C. per minute and a hold at 60° C. for 5 minutes. The identity of methylbutenol measured in vial headspace was assessed by comparison of GC peak retention times with those obtained from authentic MBO standards, and by GC-mass spectrometry.

Example II

Assays of Activity of MBO Synthase from *P. Sabiniana*

The below assays were run at pH 8.0 in a 50 mM Hepes buffer with 10% glycerol, 100 mM KCl, 20 mM $MgCl_2$, 5 mM $MnCl_2$, and 10 mM DMAPP. Assays were incubated for 2 hours at 37° C., and vial headspace was run on GC. Products were identified by comparing retention times with authentic standards.

Figure 3B:
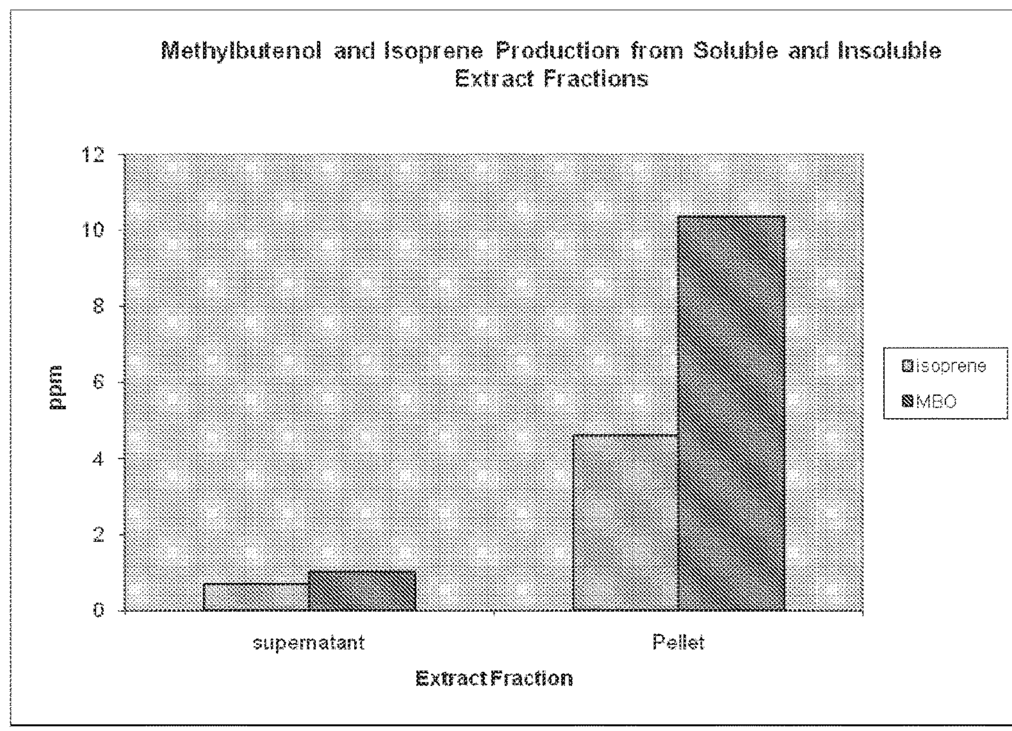

A) Methylbutenol and Isoprene Production from Soluble and Insoluble Extract Fractions FIG. 3 demonstrates that expressed enzyme (with both N and C-terminal His tags (for purification) possess dual catalytic activity and can form both isoprene and methylbutenal from the substrate DMAPP (dimethylallyl pyrophosphate (or -diphosphate)). The enzyme partitions to the insoluble fraction during the extraction process.

B) Effect of Boiling and EDTA on Enzyme Activity

Figure 4:
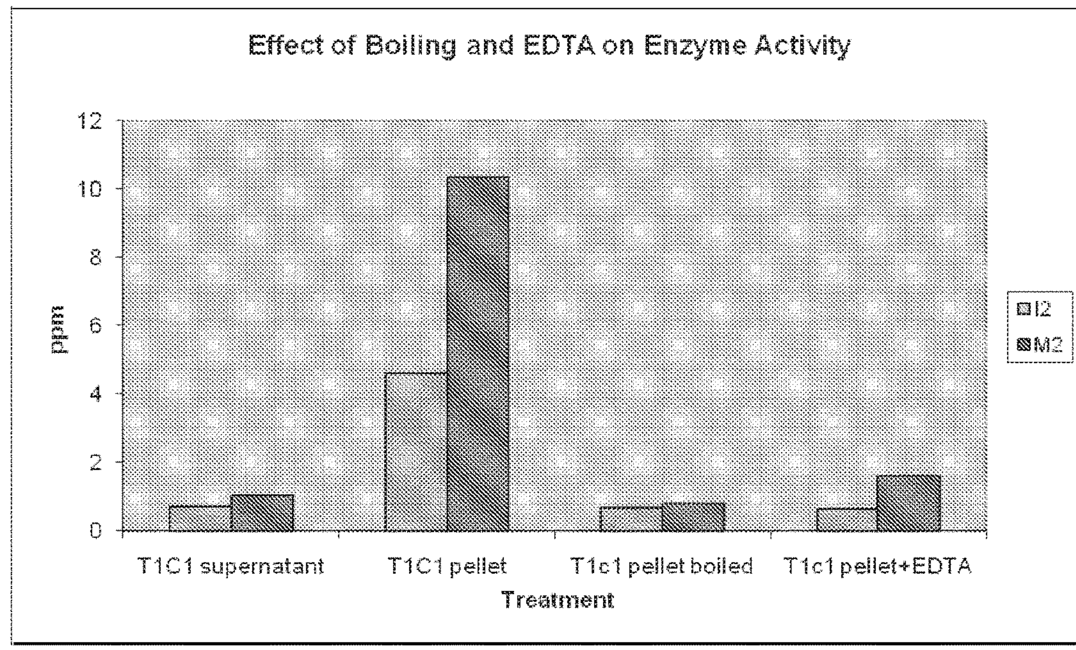
FIG. 4 demonstrates the effect of boiling and EDTA on enzyme activity.

FIG. 4 demonstrates that most of the activity is in the insoluble fraction. Furthermore, experiments determined that the conversion of DMAPP to isoprene and MBO is the result of the MBO synthase. For example, assays run with a boiled pellet (the most active extract) show little or no production of isoprene or MBO. Thus, boiling the extract inactivated the enzyme responsible for DMAPP conversion. Also, assays run with active enzyme in the presence of EDTA show little conversion of DMAPP to isoprene or MBO. This is significant because MBO synthase requires a divalent cation to function. EDTA chelates these cations and thus eliminated, enzyme function.

C) Effect of Co-Factor Replacement on MBO Synthase Activity

Figure 5:
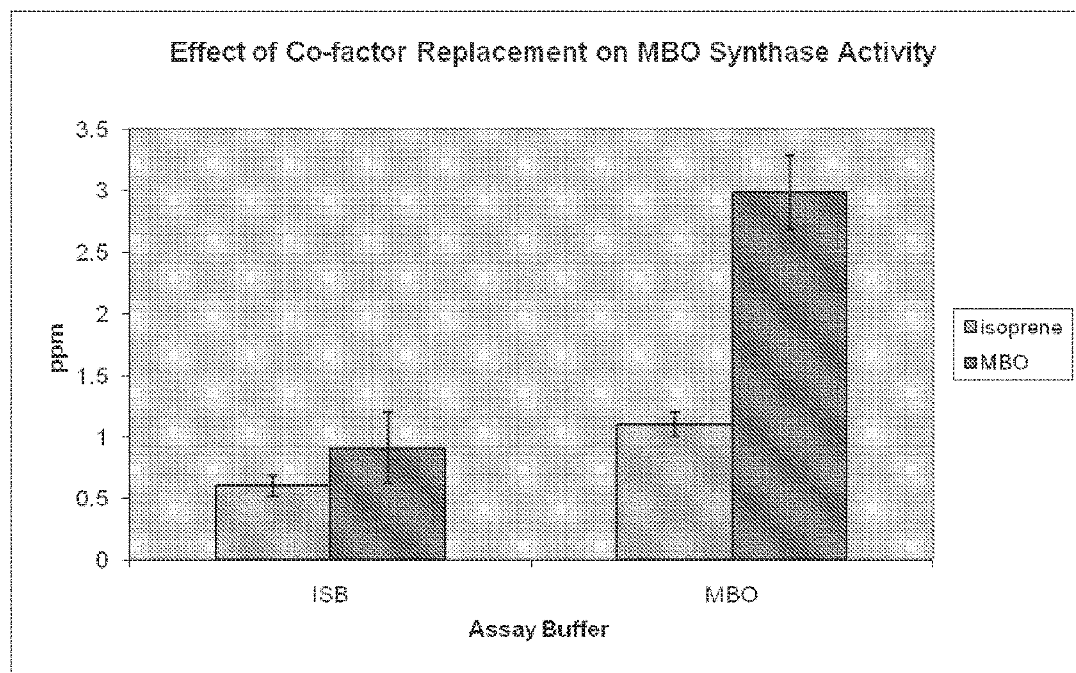
FIG. 5 demonstrates the effect of co-factor replacement on MBO synthase activity.

FIG. 5 demonstrates the effect of selectively removing the cation co-factors for MBO synthase function. The plant extract MBO synthase uses both $Mn^{2+}$ and $K^+$ as co-factors. Angiosperm isoprene synthases uses $Mg^{2+}$. By washing the pellet containing the recombinant MBO synthase protein extracted from *E. coli*, the $Mn^{2+}$ and $K^+$ ions were removed. The pellets were then resuspended in isoprene synthase buffer containing $Mg^{2+}$ or MBO synthase buffer containing $Mn^{2+}$ and $K^+$. Assays run in isoprene synthase buffer (without $Mn^{2+}$ and $K^+$ cofactors) show little activity. Assays run in MBO synthase buffer (with both $Mn^{2+}$ and $K^+$) show activity producing isoprene and MBO with about 3 fold preference for forming MBO. Thus, the catalytic activity observed is from an MBO synthase (e.g., the cloned gene).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An isolated and purified methyl butenol (MBO) synthase cDNA molecule, wherein the MBO synthase cDNA molecule comprising any one of SEQ ID NOs: 12-17 or at least 95% identity thereto, or a cDNA molecule encoding MBO synthase polypeptide comprising any one of SEQ ID NOs: 29-34.

2. An expression vector comprising a MBO synthase cDNA molecule of claim 1.

3. An isolated prokaryotic or eukaryotic host cell transformed with a MBO synthase cDNA molecule of claim 1.

4. A prokaryotic or eukaryotic host cell transformed with the vector of claim 2.

5. The host cell of claim 3, wherein the transformed cell expresses MBO synthase.

6. An isolated and purified methyl butenol (MBO) synthase cDNA, wherein the MBO synthase cDNA comprising any one of SEQ ID NOs: 12-17 or a MBO synthase cDNA molecule encoding MBO synthase polypeptide comprising any one of SEQ ID NOs: 29-34.

7. A method to produce methyl butenol comprising transforming a host cell with a cDNA molecule of claim 1 and expressing said molecule in a host cell so as to yield methyl butenol.

8. The method of claim 7, wherein said host cell is a strain of yeast, bacteria, cyanobacteria, eukaryotic micro algae or a combination thereof.

9. The method of claim 8, wherein said yeast is *Saccharomyces cerevisiae*.

10. The method of claim 8, wherein said bacteria is a C5- or C6-fermentative organism.

11. The method of claim 10, wherein said C5-fermenative organism is a species of Zymomonas.

12. The method of claim 8, wherein said bacteria is *Klebsiella oxytoca*.

13. The method of claim 8, wherein said cyanobacteria is *Synechococcus*sp., *Synechocystis* sp., or *Anabaena* sp.

14. The method of claim 8, wherein said eukaryotic micro algae is *Chlorella* sp., *Scenedesnius* sp., *Bracteococcus* sp. or *Chlamydomonus* sp.

* * * * *

UNITED STATES PATENT AND TRADEMARK OFFICE
CERTIFICATE OF CORRECTION

PATENT NO. : 10,246,695 B2
APPLICATION NO. : 15/797632
DATED : April 2, 2019
INVENTOR(S) : Gray et al.

It is certified that error appears in the above-identified patent and that said Letters Patent is hereby corrected as shown below:

In the Claims

In Column 90, Line 39, in Claim 11, delete "C5-fermenative" and insert --C5-fermentative-- therefor In Column 90, Line 44, in Claim 13, delete "Synechococcussp.," and insert --Synechococcus sp.,-- therefor In Column 90, Line 46, in Claim 14, delete "Scenedesnius" and insert --Scenedesmus-- therefor Signed and Sealed this
Twenty-eighth Day of April, 2020

Andrei Iancu
*Director of the United States Patent and Trademark Office*